US012774270B2

(12) United States Patent
Abdu-Allah et al.

(10) Patent No.: US 12,774,270 B2
(45) Date of Patent: Oct. 27, 2026

(54) DESIGN, SYNTHESIS AND MECHANISMS OF ANTICANCER ACTIVITY OF NEW ACETYLATED 5-AMINOSALICYLATE-THIAZOLINONE HYBRID DERIVATIVES

(71) Applicant: University of Sharjah, Sharjah (AE)

(72) Inventors: Hajjaj H.M. Abdu-Allah, Sharjah (AE); Wafaa S. Ramadan, Sharjah (AE); Maha Mohamed Saber-Ayad, Sharjah (AE); Rifat Hamoudi, Sharjah (AE); Samrein Ahmed, Sharjah (AE); Thenmozhi Venkatachalam, Sharjah (AE); Shirin Hafezi, Sharjah (AE); Abdel-Nasser El-Shorbagi, Sharjah (AE); Hamadeh Tarazi, Sharjah (AE); Nelson da Cruz Soares, Sharjah (AE); Moahammed Harb Semreen, Sharjah (AE); Rafat El-Awady, Sharjah (AE)

(73) Assignee: University of Sharjah, Sharjah (AE)

( * ) Notice: Subject to any disclaimer, the term of this patent is extended or adjusted under 35 U.S.C. 154(b) by 433 days.

(21) Appl. No.: 18/214,215

(22) Filed: Jun. 26, 2023

(65) Prior Publication Data

US 2025/0002467 A1 Jan. 2, 2025

(51) Int. Cl.

*C07D 277/54* (2006.01)
*A61K 31/426* (2006.01)
*A61P 35/00* (2006.01)

(52) U.S. Cl.

CPC .......... *C07D 277/54* (2013.01); *A61K 31/426* (2013.01); *A61P 35/00* (2018.01)

(58) Field of Classification Search

CPC ............................ C07D 277/54; A61K 31/426
See application file for complete search history.

(56) References Cited

PUBLICATIONS

Abdu-Allah et al. (Bioorganic Chemistry (2020); 94: 103378) (Year: 2020).*

* cited by examiner

*Primary Examiner* — Brandon J Fetterolf
(74) *Attorney, Agent, or Firm* — DLA Piper LLP (US)

(57) ABSTRACT

Novel 5-Aminosalicylate-4-thiazolinone derivatives for therapeutic formulations and methods for treating cancer. There are provided novel compounds as development of new anti-cancer agents with multicellular targets and with higher selectivity to cancer cells to enhance the outcome of cancer therapy. In a preferred aspect, there is provided a pharmaceutical composition, including a therapeutically effective amount of compound I.A, or a pharmaceutically acceptable salt thereof, and one or more pharmaceutical excipients.

13 Claims, 36 Drawing Sheets a b

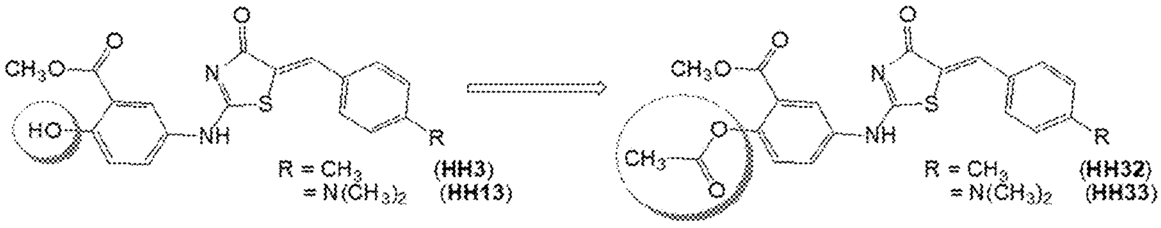

a

R = $CH_3$ (HH3)
= $N(CH_3)_2$ (HH13)

b

R = $CH_3$ (HH32)
= $N(CH_3)_2$ (HH33)

FIG. 1

| Species | Reference body weight (kg) | Working weight range (kg) | Body surface area (m²) | To convert dose in mg/kg to dose in mg/m², multiply by $K_m$ | To convert animal dose in mg/kg to HED in mg/kg, either | |
|---|---|---|---|---|---|---|
| | | | | | Divide animal dose by | Multiply animal dose by |
| Human | 60 | - | 1.62 | 37 | - | - |
| Mouse | 0.02 | 0.011-0.034 | 0.007 | 3 | 12.3 | 0.081 |
| Hamster | 0.08 | 0.047-0.157 | 0.016 | 5 | 7.4 | 0.135 |
| Rat | 0.15 | 0.08-0.27 | 0.025 | 6 | 6.2 | 0.162 |
| Ferret | 0.30 | 0.16-0.54 | 0.043 | 7 | 5.3 | 0.189 |
| Guinea pig | 0.40 | 0.208-0.700 | 0.05 | 8 | 4.6 | 0.216 |
| Rabbit | 1.8 | 0.90-3.0 | 0.15 | 12 | 3.1 | 0.324 |
| Dog | 10 | 5-17 | 0.50 | 20 | 1.8 | 0.541 |
| Monkeys (rhesus) | 3 | 1.4-4.9 | 0.25 | 12 | 3.1 | 0.324 |
| Marmoset | 0.35 | 0.14-0.72 | 0.06 | 6 | 6.2 | 0.162 |
| Squirrel monkey | 0.60 | 0.29-0.97 | 0.09 | 7 | 5.3 | 0.189 |
| Baboon | 12 | 7-23 | 0.60 | 20 | 1.8 | 0.541 |
| Micro pig | 20 | 10-33 | 0.74 | 27 | 1.4 | 0.730 |
| Mini pig | 40 | 25-64 | 1.14 | 35 | 1.1 | 0.946 |

FIG. 2

R = $CH_3$ [HH32]
R = $N(CH_3)_2$ [HH33]

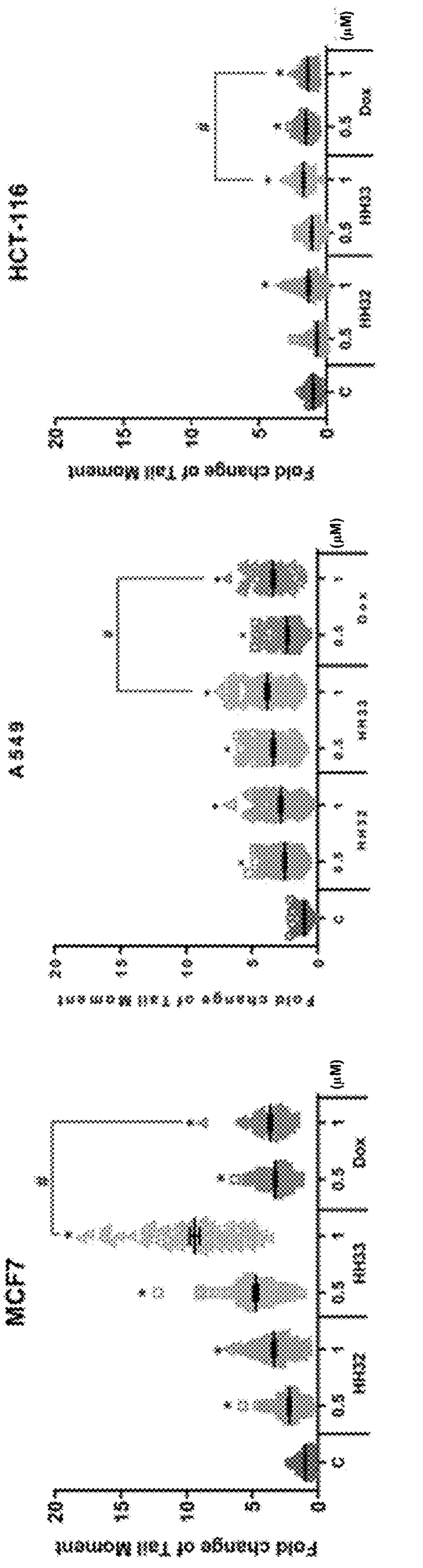
FIG. 9B
FIG. 9C
FIG. 9D
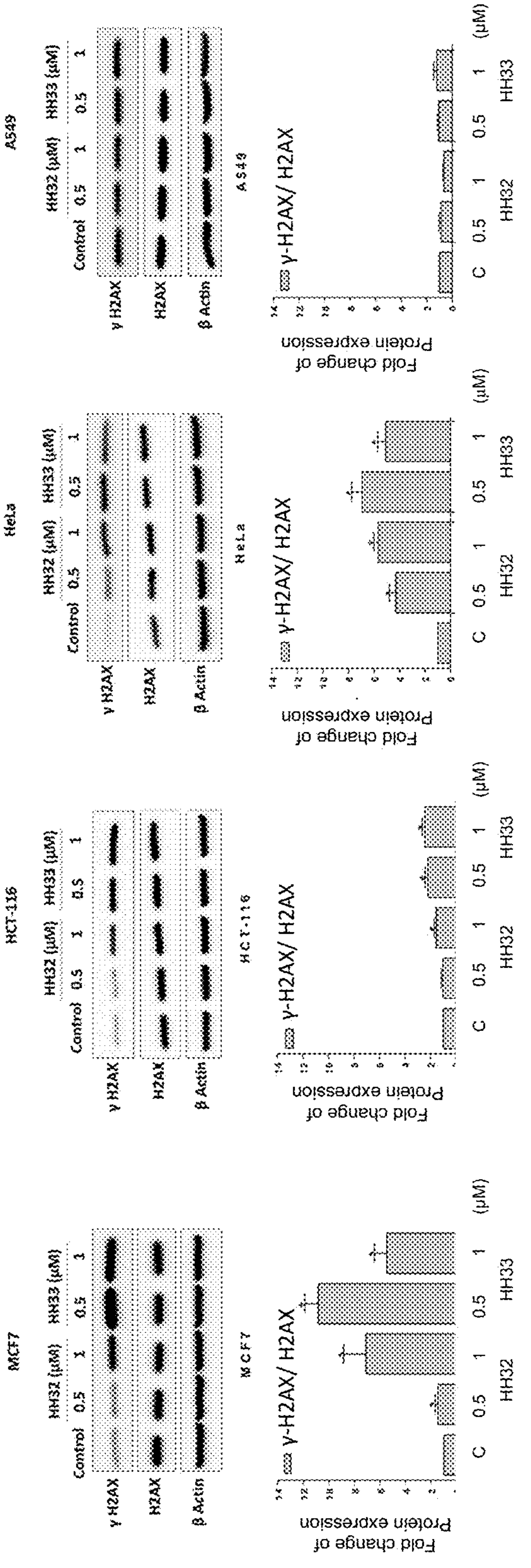
FIG. 10A
FIG.10B
FIG.10C
FIG. 10D

FIG. 11E
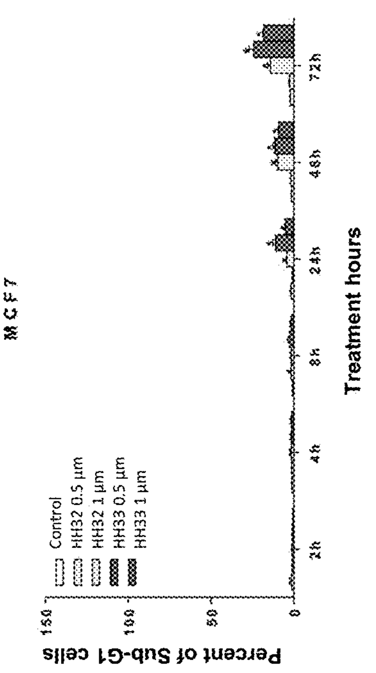
FIG. 11F
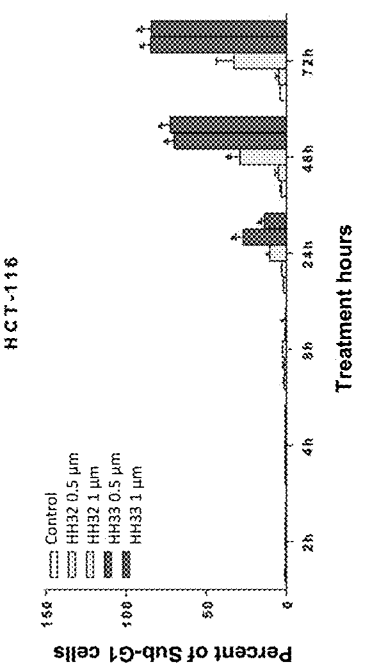
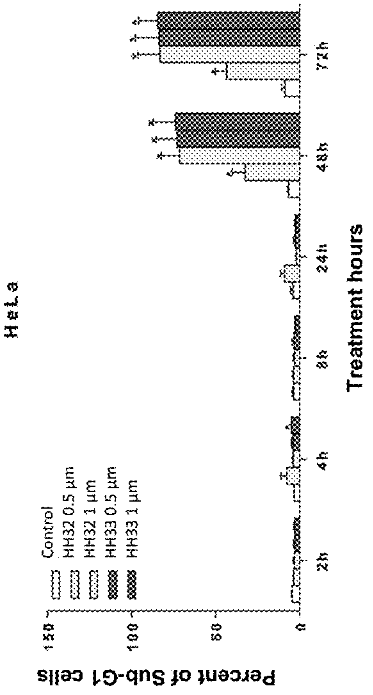
FIG. 11G
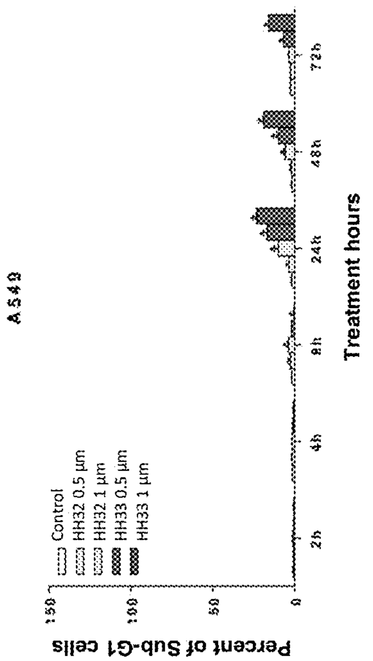
FIG. 11H

FIG. 11M
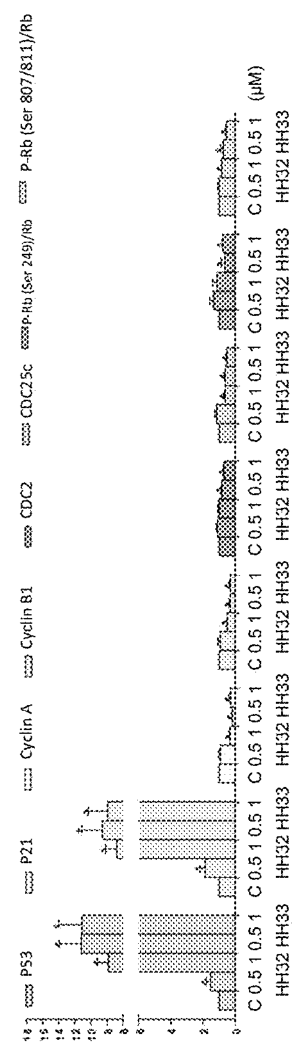
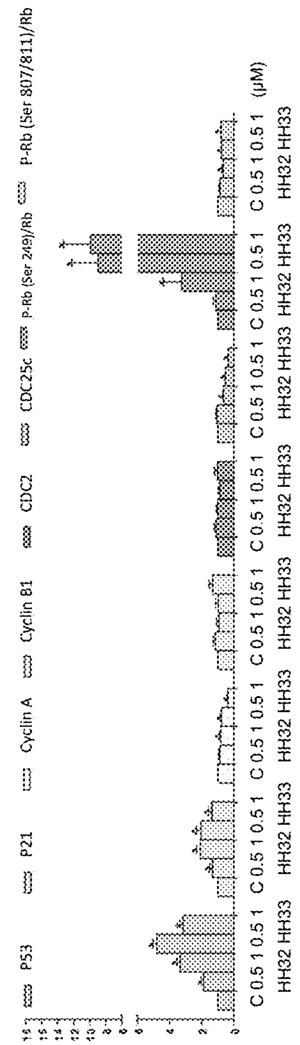
FIG. 11N
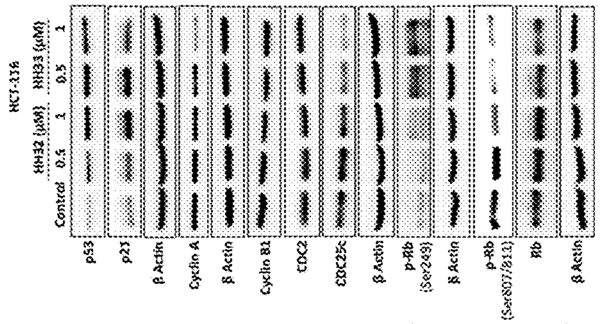
FIG. 11J
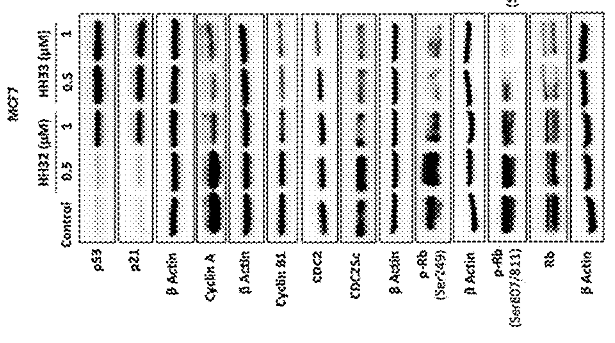
FIG. 11I

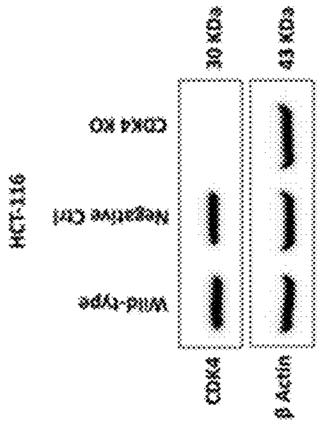
FIG. 14A
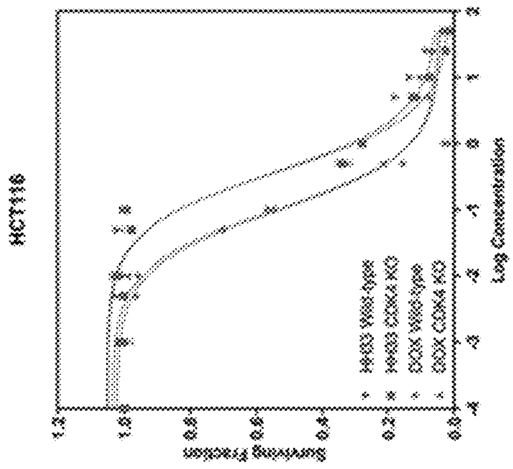
FIG.14B
| | IC50 (μM) | |
|---|---|---|
| | HH33 | DOX |
| HCT-116 Wild type | 0.44 | 0.11 |
| HCT-116 CDK4 KO | 0.43 | 0.12 |
FIG. 14C CDC25c CDK1/cyclin-B

| | DMSO vs HH32 | | | | DMSO vs HH33 | | |
|---|---|---|---|---|---|---|---|
| | fold change | p-value | FDR | | fold change | p-value | FDR |
| 2-Butenedioic Acid | -0.17 | 2.08E-01 | 8.71E-01 | | -0.06 | 7.76E-01 | 8.55E-01 |
| 3-Aminoisobutyric Acid | 0.36 | 1.04E-01 | 8.71E-01 | | 0.54 | 3.18E-01 | 8.42E-01 |
| 9H-Purin-6-Ol | -0.67 | 4.10E-01 | 8.71E-01 | | -0.74 | 3.77E-01 | 8.43E-01 |
| Decanoic Acid | -0.61 | 6.99E-02 | 8.71E-01 | | -1.07 | 2.40E-02 | 4.23E-01 |
| Hydroxylamine | 0.17 | 6.28E-01 | 8.95E-01 | | 0.27 | 1.79E-01 | 8.42E-01 |
| Inosine | 0.77 | 2.22E-01 | 8.71E-01 | | 0.80 | 1.29E-01 | 8.26E-01 |
| Lactic Acid | -0.19 | 4.95E-01 | 8.71E-01 | | -0.17 | 5.61E-01 | 8.50E-01 |
| Phosphoric acid | 0.19 | 2.76E-01 | 8.71E-01 | | 0.10 | 5.09E-01 | 8.43E-01 |
| Stearic Acid | 1.13 | 4.66E-01 | 8.71E-01 | | 0.54 | 4.82E-01 | 8.43E-01 |
| Uracil | 0.03 | 9.48E-01 | 9.88E-01 | | 0.50 | 3.20E-01 | 8.43E-01 |
| Butanedioic Acid | 0.23 | 5.54E-01 | 8.71E-01 | | -0.18 | 6.61E-01 | 8.55E-01 |
| D-Arabinose | -0.24 | 3.03E-01 | 8.71E-01 | | -0.21 | 3.73E-01 | 8.43E-01 |
| L-5-Oxoproline | 0.36 | 5.58E-01 | 8.71E-01 | | 0.32 | 4.51E-01 | 8.43E-01 |
| L-Aspartic Acid | 0.27 | 7.32E-01 | 9.05E-01 | | -0.05 | 9.61E-01 | 9.61E-01 |
| Palmitic Acid | 0.30 | 7.24E-01 | 9.05E-01 | | 0.21 | 7.30E-01 | 8.55E-01 |
| Spermine | 0.03 | 9.42E-01 | 9.88E-01 | | -0.29 | 5.08E-01 | 8.43E-01 |
| Dodecanoic Acid | -0.35 | 5.33E-01 | 8.71E-01 | | -0.44 | 4.46E-01 | 8.43E-01 |
| L-Lysine | 0.52 | 4.06E-01 | 8.71E-01 | | -0.21 | 4.59E-01 | 8.43E-01 |
| L-Threonine | -1.01 | 2.52E-01 | 8.71E-01 | | -0.55 | 4.55E-01 | 8.43E-01 |
| L-Tyrosine | -0.02 | 9.08E-01 | 9.88E-01 | | 0.18 | 4.93E-01 | 8.43E-01 |
| 2-Propenoic acid | -0.12 | 8.30E-01 | 9.78E-01 | | 0.22 | 7.54E-01 | 8.55E-01 |
| D-Mannose | -0.42 | 2.95E-01 | 8.71E-01 | | -0.58 | 1.97E-01 | 8.42E-01 |
| Dl-Ornithine | 0.34 | 4.79E-01 | 8.71E-01 | | 0.04 | 8.98E-01 | 9.15E-01 |
| Glyceric Acid | -0.05 | 7.86E-01 | 9.47E-01 | | 0.36 | 8.63E-02 | 8.26E-01 |
| Guanosine | -0.55 | 3.18E-02 | 8.71E-01 | | -0.10 | 7.69E-01 | 8.55E-01 |
| L-Leucine | -0.51 | 6.02E-01 | 8.95E-01 | | 0.50 | 6.46E-01 | 8.55E-01 |
| Oleic Acid | 0.45 | 3.24E-01 | 8.71E-01 | | 0.25 | 6.26E-01 | 8.55E-01 |
| Phosphorylethanolamine | -0.84 | 4.70E-01 | 8.71E-01 | | -0.65 | 5.45E-01 | 8.50E-01 |
| 1,3-Propanediol | -0.01 | 9.88E-01 | 9.88E-01 | | -1.03 | 3.02E-01 | 8.43E-01 |
| Adenosine | 0.01 | 9.56E-01 | 9.88E-01 | | -1.02 | 4.93E-03 | 1.31E-01 |
| Dl-Phenylalanine | -0.13 | 3.33E-01 | 8.71E-01 | | -0.14 | 1.11E-01 | 8.26E-01 |
| L-Glutamic acid | -0.44 | 6.86E-01 | 9.05E-01 | | -1.48 | 2.89E-01 | 8.43E-01 |
| L-Isoleucine | 0.34 | 5.01E-01 | 8.71E-01 | | 0.09 | 8.72E-01 | 9.06E-01 |
| Myo-Inositol | 0.26 | 3.74E-01 | 8.71E-01 | | 0.18 | 4.73E-01 | 8.43E-01 |
| Myristic Acid | -0.59 | 3.60E-01 | 8.71E-01 | | -0.76 | 2.86E-01 | 8.43E-01 |
| Oxalic Acid | 0.81 | 3.60E-01 | 8.71E-01 | | 0.37 | 6.41E-01 | 8.55E-01 |
| Pyroglutamic Acid | -0.14 | 4.10E-01 | 8.71E-01 | | 0.07 | 7.67E-01 | 8.55E-01 |
| Serine | -0.51 | 3.56E-01 | 8.71E-01 | | -0.90 | 2.04E-01 | 8.42E-01 |
| Spermidine | 0.11 | 7.35E-01 | 9.05E-01 | | 0.13 | 7.39E-01 | 8.55E-01 |
| 1-Monopalmitin | -0.48 | 5.05E-01 | 8.71E-01 | | -4.58 | 4.52E-06 | 2.40E-04 |
| Arachidonic acid | -0.56 | 6.42E-01 | 8.95E-01 | | -0.22 | 7.90E-01 | 8.55E-01 |
| Cholesterol | 0.56 | 6.23E-01 | 8.95E-01 | | 0.67 | 3.96E-01 | 8.43E-01 |
| Diacetone Alcohol | -1.11 | 3.20E-01 | 8.71E-01 | | -0.31 | 6.98E-01 | 8.55E-01 |
| L-Methionine | -0.52 | 6.80E-01 | 9.05E-01 | | -0.26 | 7.80E-01 | 8.55E-01 |
| L-Valine | 0.01 | 9.73E-01 | 9.88E-01 | | -0.19 | 7.09E-01 | 8.55E-01 |
| Scyllo-Inositol | 0.03 | 9.25E-01 | 9.88E-01 | | -0.13 | 5.33E-01 | 8.50E-01 |
| Tyrosine | -0.97 | 3.18E-01 | 8.71E-01 | | -1.48 | 1.20E-01 | 8.26E-01 |
| 11-Eicosenoic acid | -1.12 | 3.06E-01 | 8.71E-01 | | -0.74 | 2.76E-01 | 8.43E-01 |
| Citric acid | 0.08 | 9.27E-01 | 9.88E-01 | | -0.21 | 8.12E-01 | 8.61E-01 |
| Cycloserine | -0.47 | 5.08E-01 | 8.71E-01 | | -1.71 | 1.22E-01 | 8.26E-01 |
| L-Cysteine | -0.46 | 5.21E-01 | 8.71E-01 | | -1.51 | 1.40E-01 | 8.26E-01 |
| Palmitelaidic Acid | -0.90 | 3.25E-01 | 8.71E-01 | | -0.66 | 2.65E-01 | 8.43E-01 |
| Trimethylamine | -0.71 | 3.51E-01 | 8.71E-01 | | -0.53 | 2.22E-01 | 8.42E-01 |

FIG. 19

DESIGN, SYNTHESIS AND MECHANISMS OF ANTICANCER ACTIVITY OF NEW ACETYLATED 5-AMINOSALICYLATE-THIAZOLINONE HYBRID DERIVATIVES

TECHNICAL FIELD

The present invention relates to novel 5-aminosalicylate-4-thiazolinone derivatives as selective anti-cancer agents with pleiotropic anti-cancer effects for therapeutic formulations and methods for treating cancer.

BACKGROUND

Cancer is a major health problem and is a leading cause of death worldwide [1]. 18.1 million new cases and 9.5 million cancer-related deaths were reported in 2018 worldwide. The number of new cancer cases is estimated to increase to 29.5 million new cases per year and the number of cancer-related deaths is estimated to increase to 16.4 million per year in 2040.

One of the major factors contributing to the failure of cancer therapy is the intrinsic or acquired resistance of cancer cells to cancer therapeutics. The risk of resistance of cancer cells increases upon using a single anti-cancer agent or a combination of anti-cancer drugs that have one cellular target. To enhance cancer cell death and to delay or prevent the development of resistance, oncologists are using combination of drugs acting by different mechanisms given to the patient in the form of repeated cycles. This strategy, despite being successful in some instances, encounters some drawbacks such as the high cost of multiple drugs, the increased risk of side effects, and the high possibility of drug-drug interactions.

A useful and effective alternative to the use of drug combination is to chemically combine multiple effective moieties in one compound. The use of hybrid compounds for cancer treatment can be safer and cheaper than the standard cancer combination therapy. Therefore, there is a need for these hybrid drugs for more effective treatment of cancer.

SUMMARY

In accordance with the present invention, novel compounds have been developed as new anti-cancer agents with multiple cellular targets and with high selectivity to cancer cells to improve the outcome of cancer therapy.

In a first aspect, disclosed is herein the general structure of compounds of the present invention:

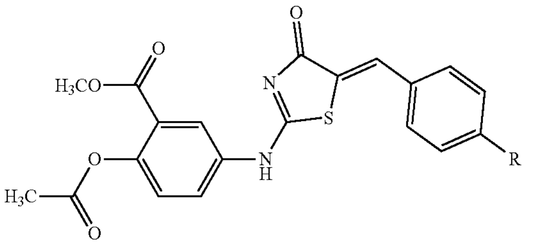

In another aspect, disclosed is herein the compound I.A, (Methyl 2-acetoxy-5-[(5-(4-methylbenzylidene)-4 (H)-oxo-1,3-thiazol-2-yl)-amino]benzoate) ("HH32"), or pharmaceutically acceptable salt thereof:

(I.A)

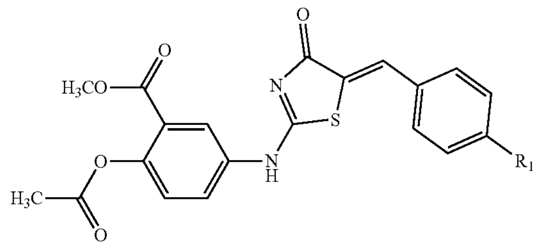

where $R_1$ is a methyl group of formula I.A:

$R_1=CH_3$.

In another aspect, disclosed is herein the compound I.B (Methyl 2-acetoxy-5-[(5-(4-dimethylaminobenzylidene)-4 (H)-oxo-1,3-thiazol-2-yl)-amino]benzoate) ("HH33"), or pharmaceutically acceptable salt thereof:

(I.B)

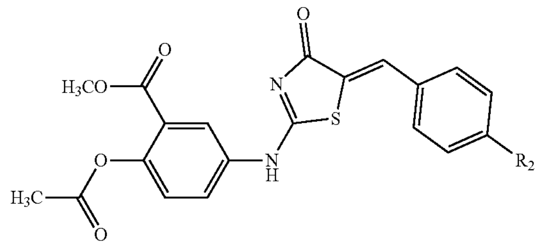

where $R_2$ is a dimethylamine group of formula I.B:

$R2=N(CH_3)_2$.

In a preferred aspect, there is provided a method of synthesizing the compound I.A including the steps of 1. acetylating compound 1 with acetic anhydride in presence of catalytic $H_2SO_4$ to obtain compound 2;
2. heterocyclying compound 2 with ammonium thiocyanate to obtain methyl 2-acetoxy-5-[(4,5-dihydro-4-oxo-1,3-thiazol-2-yl)-amino]benzoate;
3. condensing methyl 2-acetoxy-5-[(4,5-dihydro-4-oxo-1,3-thiazol-2-yl)-amino]benzoate with 4-methylbenzaldehyde to obtain compound I.A;

as shown in the following diagram:

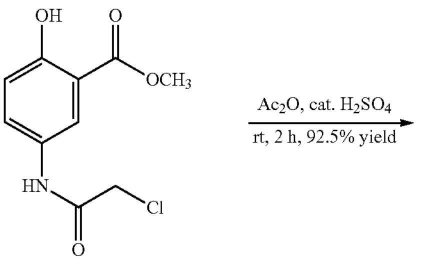

1

-continued

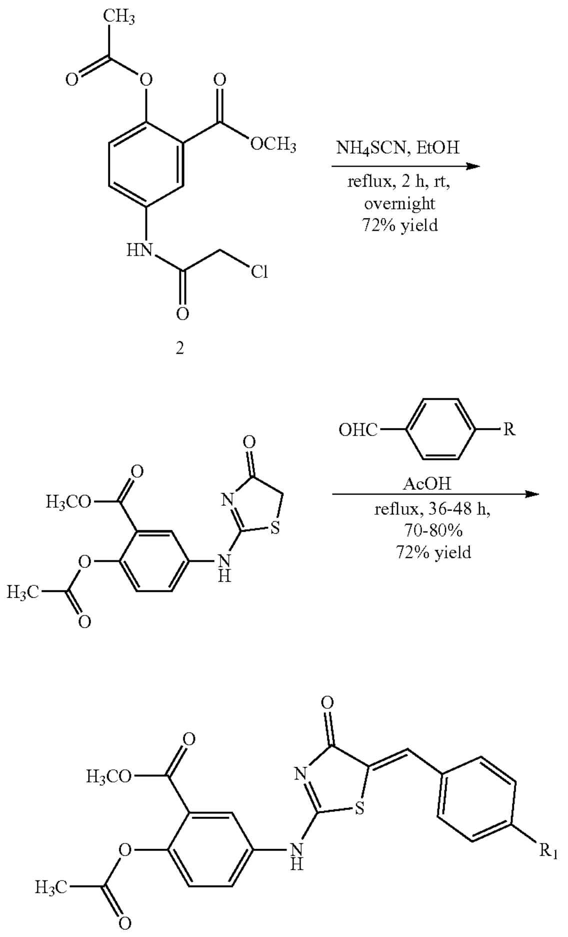

2

-continued

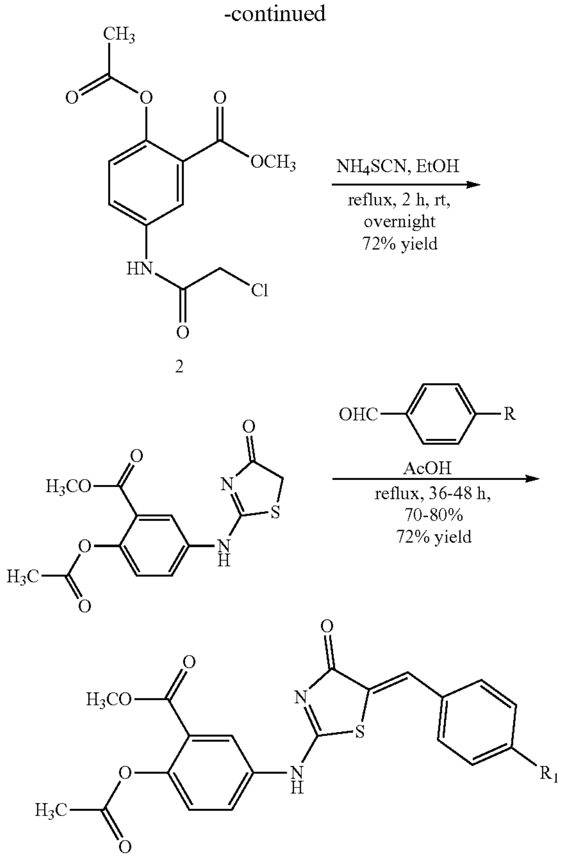

2

In a preferred aspect, there is provided a method of synthesizing the compound I.B including: the steps of 1. acetylating compound 1 with acetic anhydride in presence of catalytic $H_2SO_4$ to obtain compound 2;
2. heterocyclying compound 2 with ammonium thiocyanate to obtain methyl 2-acetoxy-5-[(4,5-dihydro-4-oxo-1,3-thiazol-2-yl)-amino]benzoate;
3. condensing methyl 2-acetoxy-5-[(4,5-dihydro-4-oxo-1,3-thiazol-2-yl)-amino]benzoate with 4-dimethylaminobenzaldehyde to obtain compound I.B:

as shown in the following diagram:

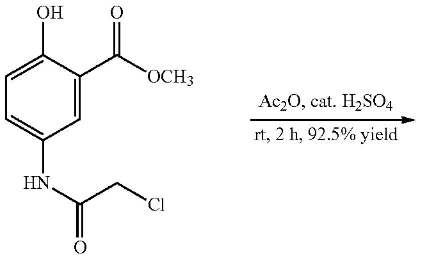

1

In a preferred aspect, there is provided a pharmaceutical composition, including a therapeutically effective amount of compound I.A, or a pharmaceutically acceptable salt thereof, and one or more pharmaceutical excipients.

In a preferred aspect, there is provided a pharmaceutical composition, including a therapeutically effective amount of compound I.B, or a pharmaceutically acceptable salt thereof, and one or more pharmaceutical excipients.

In a most preferred aspect, there is provided a method of treating a subject afflicted by a cancer by administering to the subject a therapeutically effective amount of compound I.A, or a pharmaceutically acceptable salt thereof, and one or more pharmaceutical excipients.

In a most preferred aspect, disclosed is a method of treating a subject by administering to the subject a therapeutically effective amount of compound I.A, where the subject is a mammal.

In a most preferred aspect, disclosed is a method of treating a subject by administering to the subject a therapeutically effective amount of compound I.A, where the mammal is a human.

In a most preferred aspect, there is provided a method of treating a subject afflicted by a cancer by administering to the subject a therapeutically effective amount of compound I.B, or a pharmaceutically acceptable salt thereof, and one or more pharmaceutical excipients.

In a most preferred aspect, disclosed is a method of treating a subject by administering to the subject a therapeutically effective amount of compound I.B, where the subject is a mammal.

In a most preferred aspect, disclosed is a method of treating a subject by administering to the subject a therapeutically effective amount of compound I.B, where the mammal is a human.

In a further aspect, disclosed is a kit for treating a subject with a cancer, comprising compound I.A, or a pharmaceutically acceptable salt thereof, and one or more pharmaceutical excipients.

In a further aspect, disclosed is a kit for treating a subject with a cancer, comprising compound I.B, or a pharmaceutically acceptable salt thereof, and one or more pharmaceutical excipients.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 provides the chemical structure of HH compounds. (a) Structure of non-acetylated compounds (HH3 and HH13). (b) Structure of acetylated compounds (HH32 and HH33).

FIG. 2 provides a conversion table where human equivalent dose (HED) dosage factors based on body surface area of other species are reported.

(FIGS. 6A-6J) Dose-response curves of HH32, HH33 and doxorubicin against FIGS. 6A-6H cancer cell lines (MCF7, HCT-116, HeLa, A549, HepG2, MDA-MB-231, U87 & U373) and FIGS. 6I-6J normal cells (F-180 and HME1) from SRB assay. The curves were generated by plotting the surviving fraction against each concentration (0.001-100 μM). Doxorubicin was used as positive control (n=3, Data: mean±SEM).

FIG. 7A Hypergeometric test of the differentially expressed cellular pathways showing the downregulated pathways in HH33-treated MCF-7 cells (n=3) compared to DMSO-treated cells (n=3). FIGS. 7B-7C Hypergeometric test of the differentially expressed cellular pathways showing the FIG. 7B upregulated and FIG. 7C downregulated pathways in HH33-treated A549 cells (n=3) compared to DMSO-treated cells (n=3). The analysis was done using metascape (http://metascape.org): a gene annotation and analysis online resource generating a graphical presentation, using gene onotology (GO) pathways. FIG. 7D Venn diagram showing six shared maximally downregulated genes between HH33-treated MCF7 (n=198) and A549 (n=737) cells.

FIGS. 9A-9D displays induction of DNA damage by HH32 and HH33 in cancer cell lines. FIG. 9A Representative images of the neutral comet assay on MCF7, A549 and HCT-116 cells treated with 0.5 and 1 μM of HH-32, HH-33 and Doxorubicin for 24 hours. The cell appears like a comet with a head containing the intact DNA and a tail containing a damaged DNA. FIGS. 9B-9D Graph for fold change of tail moment over control untreated cells in FIG. 9B MCF7, FIG. 9C A549 and FIG. 9D HCT-116. Each symbol represents a cell. * $p<0.05$ vs control (C). #$p<0.05$ vs 1 μM Dox.

FIGS. 10A-10L displays DNA damage response induced after HH32 and HH33 treatment. MCF7, HCT-116, HeLa and A549 were treated with 0.5 and 1 μM of HH32 or HH33 for 24 h. FIGS. 10A-10D Upper panels: Western blots detection for γ-H2AX following treatment with HH32 and HH33. Lower panels: Fold change quantification of γ-H2AX over DMSO-treated control normalized to the β-actin as a loading control. FIGS. 10E-10H Upper panels: Western blots detection for P-ATM, ATM, P-Chk2 and Chk2 after treatment with HH32 and HH33. Lower panels: P-ATM and P-Chk2 band quantification after normalization to the total protein and the β-actin as a loading control. FIGS. 10I-10L Upper panels: Western blots analysis for P-ATR, ATR, P-Chk1 and Chk1 post HH32 and HH33 treatment. Lower panels: Fold change for P-ATR and P-Chk1 after band quantification and normalization to the total protein and the β-actin as a loading control. Error bars represent SEM of three independent experiments. * $p<0.05$ vs control (C).

FIGS. 11A-11H PI staining and cell cycle analysis using flow cytometry were performed after treatment with DMSO, 0.5 or 1 μM HH32 or HH33 for the indicated time points. FIGS. 11A-11D Bar Graphs showing the percentage of G2/M phase arrest after treatment. FIGS. 11E-11H Graphs showing the percentage of sub-G1 accumulation after treatment. FIGS. 11I-11L Western blots analysis for p53, p21, Cyclin A, Cyclin B1, CDC2, CDC25c, p-Rb (Ser249), p-Rb (Ser807/811) and Rb proteins in the tested cells after treatment with 0.5 and 1 μM of HH32 or HH33 for 24 h. FIGS. 11M-11P Graphs showing quantification of band intensities after normalization to β-actin and DMSO-treated control. Error bars represent SEM of three independent experiments. * $p<0.05$ vs control (C).

FIGS. 12A-12D Histogram plots represent cell cycle distribution after DMSO or 0.5 and 1 μM of HH32 or HH33 treatment for FIG. 12A MCF7, FIG. 12B HCT116, FIG. 12C HeLa and FIG. 12D A549. Cells were fixed with 70% ethanol at indicated time points and stained with propidium iodide (PI) and analyzed by flow cytometry.

FIG. 13A MCF7, FIG. 13B HCT-116, FIG. 13C HeLa and FIG. 13D A549 were treated with 0.5 and 1 μM of HH32 or HH33 for 24 h. Upper panels: blot images for Cyclin E, Cyclin D1 and CDK2 post HH32 and HH33 treatment. Lower panels: Fold change for Cyclin E, Cyclin D1 and CDK2 after band quantification and normalization β-actin as a loading control. Error bars represent SEM of three independent experiments. * $p<0.05$ vs control (C).

FIGS. 14A-14E shows sensitivity of CDK4 Knockout and wild type HCT-116 cells to HH33 and DOX. FIG. 14A Western blot analysis for expression level of CDK4 in wild type, negative control and CDK4 knockout (KO) HCT-116 cells. FIG. 14B Dose-response curves of HH33 and doxorubicin against wild type and CDK4 knockout HCT-116 cells from SRB assay. FIG. 14C IC50 values of HH33 and Dox in wild type and CDK4 knockout (KO) HCT-116 cells. FIG. 14D Histogram plots represent cell cycle distribution for CDK4 knockout HCT-116 cells after DMSO or 0.5 and 1 μM of HH33 treatment for indicated time points. FIG. 14E Bar graph showing the percentage of Sub G1, G1, S and G2/M cell cycle phases after treatment with HH33 in CDK4 knockout HCT-116 cells.

FIGS. 16A-16D Annexin V and Propidium iodide (PI) double staining of MCF7, HCT-116, HeLa and A549 cells after 12, 24 and 48 hours of HH32 and HH33 treatment. FIGS. 16E-16H Activation of caspase-9 intrinsic apoptotic pathway induced by HH32 and HH33 compounds in MCF7, HCT-116, HeLa and A549 cells. FIGS. 16I-16L Activation of caspase-8 and downstream protein Bid extrinsic apoptotic pathways induced by HH32 and HH33 compounds in MCF7, HCT-116, HeLa and A549 cells.

FIG. 19 provides a summary of MCF-7 metabolites identified by Gas Chromatography-Mass Spectrometry analysis. Each sheet summarizes the dataset after a stepwise data processing analysis, specifically filter of the missing values, normalization, imputation, and metabolites profile after treatment with HH32 and HH33 compounds. significance ($p<0.05$).

DEFINITIONS

Figure 3:
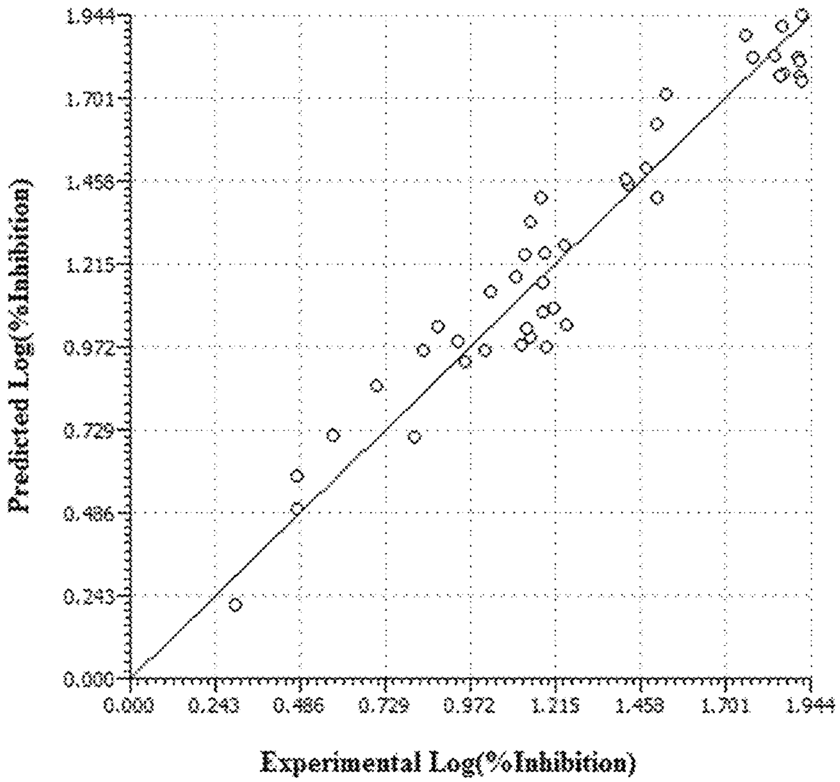
FIG. 3 provides a scatter plot of experimental versus predicted bioactivities (expressed by % inhibition against MCF7 cells) derived from the best QSAR equation.

As used in this description and the accompanying claims, the following terms shall have the meanings indicated, unless the context otherwise requires:

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

As used herein, "treatment" is understood to refer to the administration of a drug or drugs to a patient suffering from cancer.

As used herein, the term "therapeutically effective amount" indicates the amount of the compound which is effective to treat any symptom or aspect of the cancer. Effective amounts can be determined routinely. Further guidance on dosages and administration regimens is provided below. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "treatment" is used conventionally, e.g., the management or care of a subject for the purpose of combating, alleviating, reducing, relieving, improving, etc., one or more of the symptoms associated with a cancer. Administering effective amounts of the compound can treat one or more aspects of the cancer disease, including, but not limited to, causing tumor regression; causing cell death; causing apoptosis; causing necrosis; inhibiting cell proliferation; inhibiting tumor growth; inhibiting tumor metastasis; inhibiting tumor migration; inhibiting tumor invasion; reducing disease progression; stabilizing the disease; reducing or inhibiting angiogenesis; prolonging patient survival; enhancing patient's quality of life; reducing adverse symptoms associated with cancer; and reducing the frequency, severity, intensity, and/or duration of any of the aforementioned aspects.

The term "subject" in accordance with the present invention, includes, e.g., mammals, such as dogs, cats, horses, rats, mice, monkeys, and humans.

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

DETAILED DESCRIPTION

Drugs with multicellular targets may replace in part the use of combination chemotherapy and decrease the risk of development of resistance. Although salicylic acid was first prepared in 1838, it is still an attractive compound that inspires chemists to synthesize new derivatives for treatment of several diseases. Thiazolinones, on the other hand, are recognized to induce a myriad of anticancer effects [2, 3]. Using computational drug discovery algorithms, previous studies suggested a strategy of dynamic hybrid pharmacophore model (DHPM), which represents the combined interaction features of different binding pockets contrary to the conventional approaches, where pharmacophore models are generated from single binding sites [4]. Molecular dynamics simulations together with virtual compound library screening have identified biologically active compounds for several targets to develop antimicrobial as well as anticancer new therapies [5].—We have previously developed a group of compounds with promising anti-cancer activity by combining a salicylic acid derivative (5-aminosalicylic acid, 5-ASA) with 4-thiazolinone [6]. Screening and testing the activity of such compounds on cancer and normal cells identified four compounds with good anti-cancer activity and some degree of selectivity towards cancer cells. To optimize the compounds' potency and selectivity we carried-out a QSAR study to explore their main structural features responsible for the growth-inhibition effects seen against the breast cancer cell line MCF7. We conducted a QSAR study of 45 compounds [6-9] against MCF7 cancer cell line under the same condition. A multiple-linear-regression equation of eight parameters represents the best developed model capable of describing the inhibitory pattern against MCF7 cells. Calculations using this model suggested two candidate compounds (HH32 and HH33) providing up to 100% growth inhibition.

The present disclosure, in some aspects, provides methods of synthesizing pre-determined highly potent and selective acetylsalicylate-4-thiazolinone hybrid derivatives developed via in silico detection and possessing anti-proliferative effects, selectivity, and potential mechanisms of anti-cancer activity.

The main structural differences between the two new derivatives of the present invention (HH32 and HH33) and the formerly developed ones, HH3 and HH13, is the acetylation of the phenolic OH of the 5-aminosalicylate in the new compounds (FIG. 1). Acetylation of salicylic acid to produce acetyl salicylic acid (Aspirin) have long been shown to improve the therapeutic potential of the former [9]. Aspirin exhibits pharmacokinetics and pharmacodynamics superior to salicylic acid [11]. The O-acetyl group in aspirin has long been recognized as an important contributor to its diverse effects [12]. In-vitro and in-vivo evidences are available that aspirin, but not salicylic acid, acetylates macromolecules such as hemoglobin, serum albumin, various proteins (enzymes and hormones) and membrane of platelet and of red blood cells [13]. On the cellular level, aspirin can acetylate several proteins and biomolecules, such as, DNA, RNA, histones, and transglutaminase [14, 15].

Recently, it has been shown that aspirin, at micromolar concentration, acetylates the tumor suppressor protein p53, a known regulator of apoptosis, in human breast cancer cells. This effect was associated with the induction of $p21^{Cip1}$, a protein involved in cell cycle arrest, and Bax, a proapoptotic protein [16, 17]. Furthermore, aspirin directly interacts with p300 in the nucleus, promotes H3K9 histone acetylation, activates FasL expression, and induces apoptosis in colorectal cancer stem cells (CSCs) [18]. Acetylation of glucose-6-phosphate dehydrogenase (G6PD) at several sites may mediate inhibition of G6PD activity, which may contribute to the ability of aspirin to exert anticancer effects through decreased synthesis of ribose sugars and NADPH [19]. Without being bound to any particular theory, the present invention proposes that these acetylation events may be the mediators of aspirin's anti-cancer activity. Another evidence that acetylation of compounds enhances their pharmacological activity is deduced from the narcotic analgesic heroin—a di-acetylated derivative of morphine-which is more active than morphine [20]. Also, the acetylated resveratrol analogues demonstrate improved anticancer potencies [21]. These findings inspired us to check the effects of acetylating our previously developed 5-ASA-4-thiazolinone compounds on their molecular effects on cancer cells and their anticancer activity.

The aim of the present invention is to synthesize pre-determined highly potent and selective acetylsalicylate-4-thiazolinone hybrid derivatives developed via in silico detection and to investigate their anti-proliferative effects, selectivity, and potential mechanisms of anti-cancer activity.

A study was conducted where promising anticancer compounds were synthesized through a novel approach based on accommodating two chemical entities acetylated salicylic acid derivative (5-aminosalicylic acid, 5-ASA) and 4-thiazolinone into a single pharmacophore structure. These two chemical entities were extensively used as building blocks for the synthesis of medicinally important drugs and were previously reported to possess anticancer activities through multiple mechanisms. Combining the two entities along with acetylation of the 5-aminosalicylic acid moiety resulted in two novel hybrid compounds with multicellular targets that have an excellent anticancer activity with good safety profile.

The disclosed hybrid compounds exhibited a promising anticancer effect on different cancer types which was superior to the most widely used anticancer drug Doxorubicin. These hybrid compounds were proven to have a safe profile on the normal cells. The pleiotropic features of these hybrid compounds suggest using them as a monotherapy which might be more safe and cheaper than the standard cancer combination therapies. So far, no disadvantages appeared.

In a first aspect, disclosed is herein the general structure of compounds of the present invention ("methyl 2-acetoxy-5-[(5-benzylidene-4-oxo-4,5-dihydro-1,3-thiazol-2-yl)-amino]benzoate"),

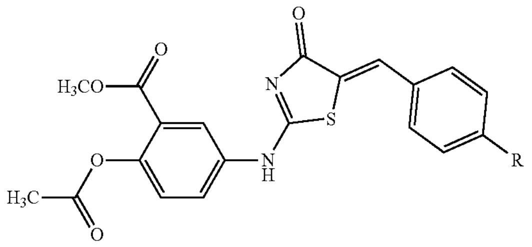

where R is independently selected from a group consisting of: $R_1$=$CH_3$ and R2=$N(CH_3)_2$.

In another aspect, disclosed is herein the compound I.A, ("Methyl 2-acetoxy-5-[(5-(4-methylbenzylidene)-4 (H)-oxo-1,3-thiazol-2-yl)-amino]benzoate") or ("HH32"), or pharmaceutically acceptable salt thereof:

(I.A)

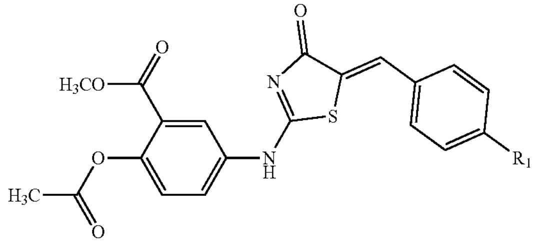

where $R_1$ is a methyl group of formula II.A: $R_1$=$CH_3$.

In another aspect, disclosed is herein the compound I.B ("Methyl 2-acetoxy-5-[(5-(4-dimethylaminobenzylidene)-4 (H)-oxo-1,3-thiazol-2-yl")-amino]benzoate) or ("HH33"), or pharmaceutically acceptable salt thereof:

(I.B)

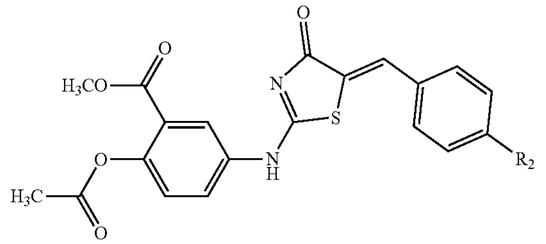

where $R_2$ is a dimethylamine group of formula II.B: $R2{=}N(CH_3)_2$.

In a preferred aspect, there is provided a method of synthesizing the compound I.A, including: (1) acetylating compound 1 with acetic anhydride in presence of catalytic $H_2SO_4$ to obtain compound 2 ("Methyl 2-acetoxy-5-(chloroacetamido)benzoate); (2) heterocyclying compound 2 with ammonium thiocyanate to obtain methyl 2-acetoxy-5-[(4,5-dihydro-4-oxo-1,3-thiazol-2-yl)-amino]benzoate ("HH31"); (3) condensing methyl 2-acetoxy-5-[(4,5-dihydro-4-oxo-1,3-thiazol-2-yl)-amino]benzoate with 4-methylbenzaldehyde to obtain compound I.A;

as shown in the following diagram:

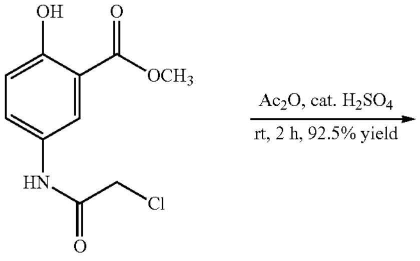

1

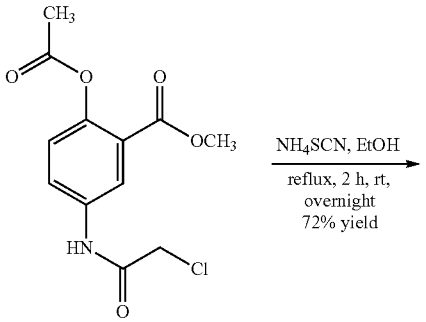

2

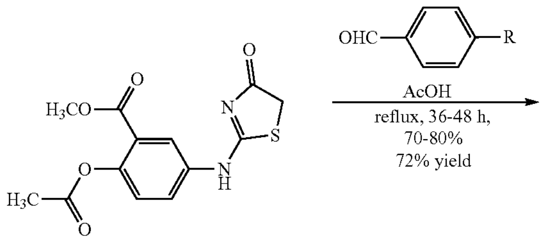

-continued

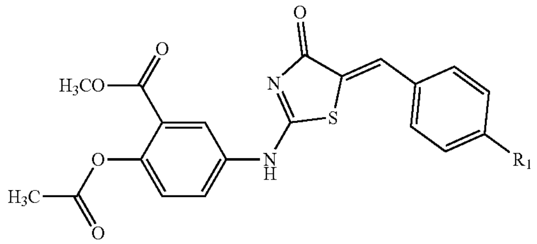

In a preferred aspect, there is provided a method of synthesizing the compound I.B including: (1) acetylating compound 1 with acetic anhydride in presence of catalytic $H_2SO_4$ to obtain compound 2 ("Methyl 2-acetoxy-5-(chloroacetamido)benzoate); (2) heterocyclying compound 2 with ammonium thiocyanate to obtain methyl 2-acetoxy-5-[(4,5-dihydro-4-oxo-1,3-thiazol-2-yl)-amino]benzoate ("HH31"); (3) condensing methyl 2-acetoxy-5-[(4,5-dihydro-4-oxo-1,3-thiazol-2-yl)-amino]benzoate with 4-methylbenzaldehyde to obtain compound I.B:

as shown in the following diagram:

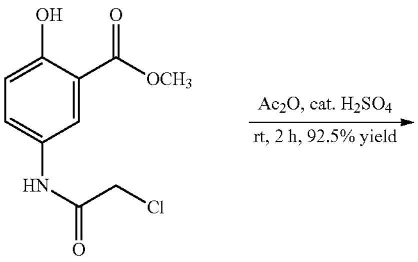

1

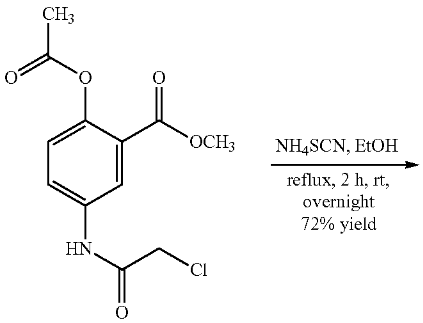

2

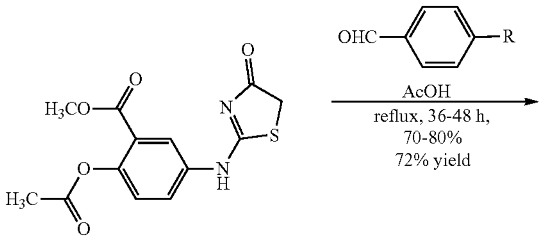

-continued

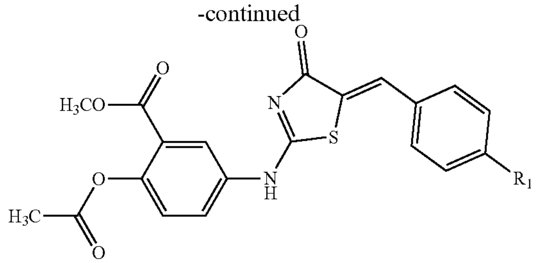

In a preferred aspect, there is provided a pharmaceutical composition, including a therapeutically effective amount of compound I.A, or a pharmaceutically acceptable salt thereof, and one or more pharmaceutical excipients.

In a preferred aspect, there is provided a pharmaceutical composition, including a therapeutically effective amount of compound I.B, or a pharmaceutically acceptable salt thereof, and one or more pharmaceutical excipients.

In a most preferred aspect, there is provided a method of treating a subject afflicted by a cancer by administering to the subject a therapeutically effective amount of compound I.A, or a pharmaceutically acceptable salt thereof, and one or more pharmaceutical excipients.

In a most preferred aspect, disclosed is a method of treating a subject by administering to the subject a therapeutically effective amount of compound I.A, where the subject is a mammal.

In a most preferred aspect, disclosed is a method of treating a subject by administering to the subject a therapeutically effective amount of compound I.A, where the mammal is a human.

In a most preferred aspect, there is provided a method of treating a subject afflicted by a cancer by administering to the subject a therapeutically effective amount of compound I.B, or a pharmaceutically acceptable salt thereof, and one or more pharmaceutical excipients.

In a most preferred aspect, disclosed is a method of treating a subject by administering to the subject a therapeutically effective amount of compound I.B, where the subject is a mammal.

In a most preferred aspect, disclosed is a method of treating a subject by administering to the subject a therapeutically effective amount of compound I.B, where the mammal is a human.

In some aspects, the present invention provides kits for novel therapeutic methods in cancer patients. For example, a kit may include one or more pharmaceutical compositions of the compound as described above. The compositions may be pharmaceutical compositions comprising a pharmaceutically acceptable excipient. In other embodiments involving kits, this invention provides a kit including the compound, optionally a chemotherapeutic agent, and optionally instructions for their use in the treatment of cancer. In still other embodiments, the invention provides a kit comprising one more pharmaceutical compositions and one or more devices for accomplishing administration of such compositions. For example, a subject kit may comprise a pharmaceutical composition and catheter for accomplishing direct intraarterial injection of the composition into a cancer. In an embodiment, the device is an intraarterial catheter. Such kits may have a variety of uses, including, for example, therapy, diagnosis, and other applications.

In a further aspect, disclosed is a kit for treating a subject with a cancer, comprising compound I.A, or a pharmaceutically acceptable salt thereof, and one or more pharmaceutical excipients.

In a further aspect, disclosed is a kit for treating a subject with a cancer, comprising compound I.B, or a pharmaceutically acceptable salt thereof, and one or more pharmaceutical excipients.

Compositions featuring the above mentioned compounds may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin. propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations may conveniently be presented in unit dosage form and may be prepared by any methods well known in the art of pharmacy. The amount of compound which can be combined with a carrier material to produce a single dosage form will vary depending upon the subject being treated, the particular mode of administration. The amount of an active ingredient which can be combined with a carrier material to produce a single dosage form will usually be that amount of the compound which produces a therapeutic effect. Usually, out of one hundred percent, this amount will range from about 1 wt % to about 99 wt % of active ingredient, preferably from about 5 wt % to about 70 wt %, most preferably from about 10 wt % to about 30 wt %.

In certain embodiments, a formulation of the compounds includes an excipient selected from the group consisting of cyclodextrins, liposomes, micelle forming agents, e.g., bile acids, and polymeric carriers, e.g., polyesters and polyanhydrides; and an active ingredient that may be the compound and/or one of its pharmaceutically acceptable derivatives. In certain embodiments, an aforementioned formulation renders orally bioavailable a compound or its derivative.

Methods of preparing these formulations or compositions include the step of bringing into association the compound with the carrier and, optionally, one or more accessory ingredients. Usually, the formulations are prepared by uniformly and intimately bringing into association a compound of the present invention with liquid carriers, or finely divided solid carriers, or both, and then, if necessary, shaping the product.

Liquid dosage forms for oral administration of the compounds include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A formulation of the compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also include buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

The tablets, and other solid dosage forms of the formulation of the compound, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the compound for rectal or vaginal administration may be presented as a suppository, which may be prepared by the compound with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of the compound include powders, sprays, ointments, pastes, creams, lotions, gels, solutions, patches and inhalants. The compound may be mixed under sterile conditions with a pharmaceutically-acceptable carrier, and with any preservatives, buffers, or propellants which may be required. The ointments, pastes, creams and gels may contain, in addition to the compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compound to the body. Such dosage forms can be made by dissolving or dispersing an extract in the proper medium. Absorption enhancers can also be used to increase the flux of the extract or dispersing the extract in a polymer matrix or gel.

Pharmaceutical compositions suitable for parenteral administration include one or more components of the compound in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compound may be formulated into pharmaceutically-acceptable dosage forms by conventional methods known to those of skill in the art. The compound may be formulated for administration in any convenient way for use in human or veterinary medicine, by analogy with other pharmaceuticals.

In certain embodiments, the above-described pharmaceutical compositions include the compound, a chemotherapeutic agent, and optionally a pharmaceutically acceptable carrier. Alternatively, the terms "chemotherapeutic agent" or "therapeutic agent" include, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and *vinca* alkaloid natural antineoplastics, such as vinblastine and vincristine.

The above compound compositions may be used in novel therapeutic methods of treatment in cancer patients. The methods include administering to a subject an effective amount of a pharmaceutical compound composition. The above invention can be used to treat any cancer irrespective of the type or cause of the cancer, and irrespective of the genetic lesions associated with it, including, but not limited to cancer, pre-cancerous cells, tumors, neoplasms, and non-malignant tumors can also be treated. Cancers that can be treated include, e.g., cancers which are primary; which arise from a primary tumor at a secondary metastatic site; which have been treated by surgery (e.g., entirely removed, surgical resection, etc); which have been treated by chemotherapy, radiation, radiofrequency ablation, and/or any other adjunct to drug therapy; which have acquired drug-resistance; which are refractory to a chemotherapeutic agent.

In other embodiments, types of cancer which can be treated in accordance with present invention include, but are not limited to: Cell Adult Acute Lymphoblastic Leukemia; Blastic Phase Chronic Myelogenous Leukemia; Bone Metastases; Brain Tumor; Breast Cancer; Cancer; Central Nervous System Cancer; Childhood Acute Lymphoblastic Leukemia; Childhood Acute Lymphoblastic Leukemia in Remission; Childhood Central Nervous System Germ Cell Tumor; Childhood Chronic Myelogenous Leukemia; Childhood Soft Tissue Sarcoma; Chordoma; Chronic Eosinophilic Leukemia (CEL); Chronic Idiopathic Myelofibrosis; Chronic Myelogenous Leukemia; Chronic Myeloid Leukemia; Chronic Myelomonocytic Leukemia; Chronic Phase Chronic Myelogenous Leukemia; Colon Cancer; Colorectal Cancer; Dermatofibrosarcoma; Dermatofibrosarcoma Protuberans (DFSP); Desmoid Tumor; Eosinophilia; Epidemic Kaposi's Sarcoma; Essential Thrombocythemia; Ewing's Family of Tumors; Extensive Stage Small Cell Lung Cancer; Fallopian Tube Cancer, Familiar Hypereosinophilia; Fibrosarcoma; Gastric Adenocarcinoma; Gastrointestinal Neoplasm, Gastrointestinal Stromal Tumor; Glioblastoma; Glioma; Gliosarcoma; Grade I Meningioma; Grade II Meningioma; Grade III Meningioma; Hematopoietic and Lymphoid Cancer, High-Grade Childhood Cerebral Astrocytoma; Hypereosinophilic Syndrome; Idiopathic Pulmonary Fibrosis; L1 Adult Acute Lymphoblastic Leukemia; L2 Adult Acute Lymphoblastic Leukemia; Leukemia, Lymphocytic, Acute L2; Leukemia, Myeloid, Chronic; Leukemia, Myeloid, Chronic Phase; Liver Dysfunction and Neoplasm; Lung Disease; Lymphoid Blastic Phase of Chronic Myeloid Leukemia; Male Breast Cancer; Malignant Fibrous Histiocytoma; Mastocytosis; Meningeal Hemangiopericytoma; Meningioma; Meningioma; Meningioma; Metastatic Cancer; Metastatic Solid Turnors; Myelofibrosis; Myeloid Leukemia, Chronic; Myeloid Leukemia, Chronic Accelerated-Phase; Myeloid Leukemia, Chronic, Chronic-Phase; Myeloid Metaplasia; Myeloproliferative Disorder (MPD) with Eosinophilia; Neuroblastoma; Noπ-T, Non-B Childhood Acute Lymphoblastic Leukemia; Oligodendroglioma; Osteosarcoma; Ovarian Germ Cell Tumor; Ovarian Low Malignant Potential Tumor; Ovarian Neoplasms; Pancreatic Cancer; Pelvic Neoplasms; Peritoneal Cavity Cancer; Peritoneal Neoplasms; Philadelphia Chromosome Positive Chronic Myelogenous Leukemia; Philadelphia Positive Acute Lymphoblastic Leukemia; Philadelphia Positive Chronic Myeloid Leukemia in Myeloid Blast Crisis; Polycythemia Vera; Pulmonary Fibrosis; Recurrent Adult Brain Tumor; Recurrent Adult Soft Tissue Sarcoma; Recurrent Breast Cancer; Recurrent Colon Cancer; Recurrent Esophageal Cancer; Recurrent Gastric Cancer; Recurrent Glioblastoma Multiforme (GBM); Recurrent Kaposi's Sarcoma; Recurrent Melanoma; Recurrent Merkel Cell Carcinoma; Recurrent Ovarian Epithelial Cancer; Recurrent Pancreatic Cancer; Recurrent Prostate Cancer; Recurrent Rectal Cancer; Recurrent Salivary Gland Cancer; Recurrent Small Cell Lung Cancer; Recurrent Tumors of the Ewing's Family; Recurrent Uterine Sarcoma; Relapsing Chronic Myelogenous Leukemia; Rheumatoid Arthritis; Salivary Gland Adenoid Cystic Carcinoma; Sarcoma; Small Cell Lung Cancer; Stage U Melanoma; Stage Ii Merkel Cell Carcinoma; Stage III Adult Soft Tissue Sarcoma; Stage III Esophageal Cancer; Stage 111 Merkel Cell Carcinoma;

Stage ill Ovarian Epithelial Cancer; Stage III Pancreatic Cancer; Stage III Salivary Gland Cancer; Stage IUB Breast Cancer; Stage UIC Breast Cancer; Stage IV Adult Soft Tissue Sarcoma; Stage IV Breast Cancer; Stage IV Colon Cancer; Stage IV Esophageal Cancer; Stage IV Gastric Cancer; Stage IV Melanoma; Stage IV Ovarian Epithelial Cancer; Stage IV Prostate Cancer; Stage IV Rectal Cancer; Stage IV Salivary Gland Cancer; Stage IVA Pancreatic Cancer; Stage IVB Pancreatic Cancer; Systemic Mastocytosis; T-CeII Childhood Acute Lymphoblastic Leukemia; Testicular Cancer; Thyroid Cancer; Unresectable or Metastatic Malignant Gastrointestinal Stromal Tumor (GIST); Unspecified Adult Solid Tumor; Untreated Childhood Brain Stem Glioma; Uterine Carcinosarcoma, and Uterine Sarcoma.

Diseases which can be treated in accordance with present invention include, e.g., diseases which are treated with gefitinib, such as, but not limited to: Adenocarcinoma of the Colon; Adenocarcinoma of the Esophagus; Adenocarcinoma of the Lung; Adenocarcinoma of the Prostate; Adenocarcinoma of the Rectum; Advanced Adult Primary Liver Cancer; Advanced Non-Nasopharyngeal Head and Neck Carcinoma; Anaplastic Astrocytoima; Anaplastic Oligodendroglima; Anaplastic Thyroid Cancer; Bladder Cancer; Brain Tumor; Breast Cancer; Breast Cancer in Situ; Breast Neoplasms; Bronchoalveolar Cell Lung Cancer; Cancer of the Fallopian Tube; Carcinoma, Squamous Cell; Cervix Neoplasms; Colon Cancer; Colorectal Cancer; Epithelial Mesothelioma; Esophageal Cancer; Esophagogastric Cancer; Follicular Thyroid Cancer; Gastric Cancer; Gastrinoma; Gastrointestinal Carcinoid; Giant Cell Glioblastoma; Glioblastoma; Glioblastoma Multiforme; Head and Neck Cancer; Hepatocellular Carcinoma; Hypopharyngeal Cancer; Inoperable Locally Advanced Squamous Cell Carcinoma of Head and Neck; Insulinoma; Intraductal Breast Carcinoma; Islet Cell Carcinoma; Large Cell Lung Cancer; Laryngeal Cancer; Lip and Oral Cavity Cancer; Lip Cancer; Liver Cancer; Lung Adenocarcinoma With Bronchiole-Alveolar Feature; Lung Cancer; Male Breast Cancer; Medullary Thyrod Cancer; Meningeal Tumors; Metastatic Colorectal Cancer; Metastatic Gastrointestinal Carcinoid Tumor; Metastatic Pancreatic Carcinoma; Mixed Gliomas; Myelogenous Leukemia, Acute; Nasopharyngeal Carcinoma; Neuroblastoma; Non-Metastatic (T2-T4, N0-N3, MO; Stages II and III) and Histologically-Confirmed Intestinal GC; Non-Metastatic Prostate Cancer; Nonresectable Adrenocortical Carcinoma; Non-Small Cell Lung Cancer; Nose Cancer; Oligodendroglial Tumors; Oral Cancer; Oropharyngeal Cancer; Osteosarcoma; Ovarian Cancer; Ovarian Neoplasms; Pancreatic Cancer; Papillary Thyroid Cancer; Peritoneal Carcinoma; Pharynx Cancer; Pneumonic-Type Adenocarcinoma (P-ADC); Primary Hepatocellular Carcinoma; Prostate Cancer; Rectal Cancer; Recurrent Adult Primary Liver Cancer; Recurrent Breast Cancer; Recurrent Colon Cancer; Recurrent Endometrial Cancer, Recurrent Esophageal Cancer; Recurrent Glioblastoma; Recurrent Rectal Cancer; Recurrent Skin Cancer; Refractory Germ Cell Tumors Expressing EGRF; Renal Cell Cancer; Rhabdomyosarcomas; Sarcomatous Mesothelioma; Skin Cancer; Soft Tissue Sarcoma; Squamous Cell Carcinoma of the Esophagus; Squamous Cell Carcinoma of the Head and Neck; Squamous Cell Carcinoma of the Skin; Squamous Cell Lung Cancer; Stage II Esophageal Cancer; Stage III Esophageal Cancer, Synovial Sarcoma; Thorax and Respiratory Cancer; Throat Cancer; Thyroid Cancer; Transitional Cell Cancer of the Renal Pelvis and Ureter; Transitional Cell Carcinoma of the Bladder; Tubal Carcinoma; Unspecified Childhood Solid Tumor; Untreated Childhood Brain Stem Glioma; Urethral Cancer.

As anticipated above, the compounds may be administered by any appropriate route, for example orally, parenterally, topically, or rectally. It will be appreciated that the preferred route may vary with, for example, the condition of the recipient of the compound and the cancer to be treated. In certain embodiments, the compound may be especially suitable for the preparation of pharmaceuticals for intravenous administration, such as intravenous injection or infusion, provided that it does not contain components with serum-precipitating and/or haemagglutinating properties which disturb such an application. The compound may therefore be provided in the form of ampoule preparations which are directed to intravenous administration. In still other embodiments, the method comprises systemic administration of a subject composition to a subject.

Also provided are methods of treating cancer, which include administering the compounds in conjunction with a chemotherapeutic agent to a subject. Conjunctive therapy includes sequential, simultaneous and separate, or co-administration of the compound and the chemotherapeutic agent in a way that the therapeutic effect of the chemotherapeutic agent does not entirely disappear when the compound is administered. In certain embodiments, compound and the chemotherapeutic agent may be combined together in the same unitary pharmaceutical composition including both entities. Alternatively, the combination of compound and chemotherapeutic agent may be administered separately in separate pharmaceutical compositions, each including one of the compound and chemotherapeutic agent in a sequential manner wherein, for example, either the compound or the chemotherapeutic agent is administered first followed by the other one.

Exemplary doses of the compounds in the range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of the compound will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg/day to about 250 mg/day per kg. In a further embodiment, the dose in the range of about 100 mg/day to about 200 mg/day per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

The combined use of the compound and other chemotherapeutic agents may reduce the required dosage for any individual component because the onset and duration of effect of the different components may be complementary. In such combination therapies, the different active agents may be delivered together or separately, and simultaneously or at different times within the day.

The data obtained from cell culture assays and animal studies may be used in formulating a range of dosage for use in humans. For example, effective dosages achieved in one animal species may be extrapolated for use in another animal, including humans, as illustrated in the conversion table of FIG. 2 where human equivalent dose (HED) dosage factors based on body surface area of other species are reported. [22]. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For the compound or combinations of the compound and other chemotherapeutic agents, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

Experimental Examples

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

As evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Materials and Methods

Design of New 5-ASA-thiazolinone Derivatives

The strategy we followed for this discovery is the synthesis of pre-determined highly potent candidates calculated via in silico detection. Based on our previous effort [6-9], we carried out a QSAR study to explore the main structural features of our 5-Aminosalicylate-4-thiazolinone derivatives responsible for the proliferation inhibition pattern seen against MCF7 cancer cells. A database of a total 45 compounds with their corresponding percent inhibition data was established covering our previously reported compounds as well as the compounds presented herein. A multiple-linear-regression equation of eight parameters representing the best-developed model capable of describing the inhibitory pattern against MCF7 cancer cell line is illustrated by the following equation:

$$\mathrm{Log}(\%\ inh0ibition) = -11.1958 - 0.0004 \times ATSC6v + 0.6379 \times AATSC6s + 45.2642 \times BCUTc_{1h} - 0.1102 \times maxHBint8 - 0.1040 \times WTPT_5 - 0.1676 \times RDF105m + 0.1258 \times RDF95e - 0.0328 \times RDF145i$$

where n=44, F-Statistic=59.45, $R^2$=0.931, $Q^2_{LOO}$=0.893, $Q^2_{LMO}$=0.837, $R^2_{Y\text{-}scr}$=0.185, s=0.129. Where in this equation, ATSC6v is centered Broto-Moreau autocorrelation of lag 6 weighted by van der Waals volumes; AATSC6s is average centered Broto-Moreau autocorrelation of lag 6 weighted by I-state; BCUTc-1h is n low highest partial charge weighted BCUTS; maxHBint8 is maximum E-state descriptors of strength for potential hydrogen bonds of path length 8; WTPT-5 is sum of path lengths starting from nitrogens; RDF105m is radial distribution function-105 weighted by relative mass; RDF95e is radial distribution function-095 weighted by relative Sanderson electronegativities; RDF145i is radial distribution function-145 weighted by relative first ionization.

The model was found to fit the experimental percent inhibition of MCF7 (FIG. 3) with considerable level of significance as indicated by its high Fischer's value (F), squared correlation coefficients ($R^2$) and the minor standard errors of estimate. The presented model is specific to our compound's chemo-type, thus their internal predictive power was judged based on leave-one-out (LOO) and leave-many-out (LMO) procedures. The probability of chance correlation was examined by Y-scrambling procedure, in which, lower ($R^2_{Y\text{-}Scr}$) value indicates lesser probability of chance correlation. The internal validation parameters achieved by the model demonstrates its reliability and robustness in predicting new derivatives within our series and could be utilized for future development.

The most influential variables that are in direct relation with the bioactivities were identified by the model as AATSC6s, BCUTc-1h and RDF95e. Those variables have favorable contribution to the overall activity as indicated by their positive coefficients and demonstrate the importance of structural electronic properties (ionization states, partial charges and electronegativities). These conclusions are in agreement with our previous findings regarding the influence of electron-donating and electron-withdrawing substituents [9].

Quantitative Structure-Activity Relationship (QSAR)

The compounds were drawn using ChemDraw Ultra 8.0 software [23] and for each compound, the lowest energy conformation was generated using MOPAC2012 [24] within VEGA-ZZ software [25, 26]. Austin Model-1 (AM1) semi-empirical force-field was employed for this purpose. PaDEL-software [27] was used for molecular descriptors calculations. The software calculates a large set of 1D-3D molecular descriptors (ca. 1875) of different classes including constitutional, topological, information indices, eigenvalue-based indices, radial distribution function (RDF), 2D/3D autocorrelation. The calculated descriptors were served as independent variables during QSAR model development. The logarithmic values of experimentally observed percent inhibition against MCF7 cancer cell line were served as the dependent variable. The QSAR models were developed and validated employing the QSARINS software [28, 29]. Model development process was initiated by reducing co-linearity (corr.>0.98) and excluding the descriptor showing higher pair-wise correlation with others. All subsets procedure was adapted for the first two variables. Next, the optimal combinations of variables (>2) relevant to the dependent variable under study were selected using a genetic algorithm (GA). During the GA variables selection phase, the population size, maximum number of generations, and mutation rate were set to 800, 2000, and 0.2 respectively. Multiple linear regression method was used for the final model building. The final model's robustness was validated employing internal predictive measures based on $Q^2_{LOO}$ (leave one-out), $Q^2_{LMO}$ (leave many-out), and $R^2_{Y\text{-}Scr}$ (Y-scrambling). Calculations suggested candidates HH32 and HH33 providing up to 100% growth inhibition. The candidates were then synthesized and subjected to pharmacological investigation.

Synthesis of Acetylated 5-ASA-thiazolinone Derivatives HH32 and HH33

Figure 4:
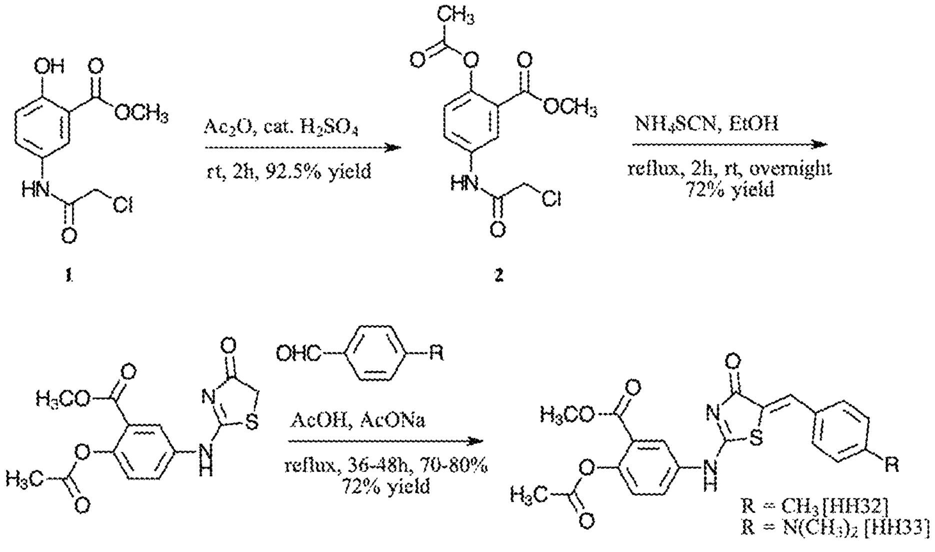
FIG. 4 provides a schematic of the synthesis of the compounds of the present invention.

The synthesis of the target compounds is described in FIG. 4. Different approaches were tried for acetylation. The one described herein was found to be the most convenient. Starting compound (1) was synthesized as reported [9], then acetylated with acetic anhydride in presence of catalytic $H_2SO_4$ to give compound (2). Heterocyclization of 2 with ammonium thiocyanate gave HH31. Knovenagel condensation of HH31 with 4-methylbenzaldehyde or 4-dimethylaminobenzaldehyde provided the target compounds HH32 and HH33, respectively. All compounds were fully characterized by spectral data.

All reagents and solvents were obtained from commercial suppliers and used without further purification. Melting points are uncorrected and were determined on an electrothermal melting point apparatus (Stuart Scientific, model SM.P.3, England, UK). Precoated silica gel plates (kieselgel 0.25 mm, 60G F254, Merck, Germany) were used for TLC monitoring of reactions. UV light was used for detection. NMR spectra were recorded on Bruker AMX400 MHz instruments. Chemical shifts were reported in ppm and are referenced to the chemical shift of residual solvent.

Synthesis of Methyl 2-acetoxy-5-(chloroacetamido)benzoate (2)

One drop of conc $H_2SO_4$was added with stirring at room temperature for 3 h to compound 1 (2.00 g, 8.20 mmol) in 5 mL of $Ac_2O$. To the reaction mixture, ice water was added, rapidly filtered and dried to give pure product. (2.13 g, 92.5% yield); $^1$H NMR (400 MHz, $CDCl_3$) δ=8.43 (br. s., 1H, NH), 8.03 (d, 1H, J=4 Hz, Ar-H), 8.03 (d, 1H, J=4 Hz, Ar-H), 7.83 (d, 1H, J=4 Hz, Ar-H), 7.06 (d, 1H, J=4 Hz, Ar-H), 4.16 (s, 2H, $CH_2$), 3.86 (s, 3H, $OCH_3$); 2.35 (s, 3H, $CH_3$); $^{13}$C NMR (100 MHz, $CDCl_3$) δ=170.07, 164.30, 164.26, 147.24, 134.75, 125.45, 124.47, 123.43, 123.06, 77.34, 77.09, 76.83, 52.42, 42.82, 20.97.

Synthesis of Methyl 2-acetoxy-5-[(4,5-dihydro-4-oxo-1,3-thiazol-2-yl)-amino]benzoate (HH31)

A solution of 2 (12.57 g, 44 mmol) and ammonium thiocyanate (7.00 g, 91.2 mmol) in 150 ml ethanol was refluxed for 2 h and allowed to stand overnight. The mixture was concentrated and filtered. The collected solid was washed with water, recrystallized from ethanol/water and dried to give (9.72 g, 72%); m.p.=185-187° C. $^1$H NMR (400 MHz, DMSO-$d_6$) δ=11.90, 11.40 (2*s, 1H; NH), 8.27, 7.99 (2*d, J=4 Hz, 1H, ArH-6), 7.48 (br. s., ½H, ArH-4), 7.30-7.22 (m, 1.5H, ArH-4, ArH-3), 4.05, 4.02 (2*s, 2H, $CH_2$), 3.83, 3.81 (2*s, 3H; $OCH_3$), 2.28 (s, 3H, $CH_3$); $^{13}$C NMR (100 MHz, DMSO-$d_6$) δ=188.58, 179.15, 169.81, 164.58, 146.84, 146.62, 137.09, 127.58, 126.08, 125.52, 125.20, 123.95, 123.71, 122.89, 52.96, 52.86, 34.88, 21.14.

General Procedure for Synthesis of Methyl 2-acetoxy-5-[(5-benzylidene-4-oxo-4,5-dihydro-1,3-thiazol-2-yl)-amino]benzoate (HH32, HH33)

To a well-stirred solution of compound 1 (0.43 g, 1.4 mmol) in acetic acid (10 mL) buffered with sodium acetate (0.18 g, 2.2 mmol), the appropriate arylaldehyde (1.6 mmol) was added. The solution was refluxed overnight till the completion of the reaction as monitored by TLC, and then poured into ice-cold water. The precipitate was filtered, and the resulting crude product was purified by recrystallization from dioxane.

Methyl 2-acetoxy-5-[(5-(4-methylbenzylidene)-4(H)-oxo-1,3-thiazol-2-yl)-amino]benzoate (HH32)

(0.43 g, 75% yield); m.p.=218-220° C.; $R_f$=0.4 (hexane/ethyl acetate; 2/1); $^1$H NMR (400 MHz, DMSO-$d_6$) δ=12.49, 11.80 (2*s, 1H; NH), 8.36, 8.08 (2*d, J=4 Hz, 1H, ArH-6), 7.73, 7.69 (2*d, J=4 Hz, 1H, ArH-4), 7.54-7.51 (m, 2H, CH═C, ArH-3), 7.42-7.28 (m, 4H, 4-MePh), 3.91, 3.83 (2*s, 3H; $OCH_3$), 2.37, 2.31 (2*s, 6H; $CH_3$); $^{13}$C NMR (100 MHz, DMSO-$d_6$) δ=179.74, 170.59, 168.81, 168.72, 163.54, 146,09, 145.88, 139.54, 135.72, 130.53, 130.43, 129.86, 129.42, 129.29, 129.17, 129.05, 126.30, 125.29, 125.21, 124.65, 124.31, 123.19, 122.89, 122.77, 122.11, 120.93, 51.96, 51.84, 20.47, 20.12.

Methyl 2-acetoxy-5-[(5-(4-dimethylaminobenzylidene)-4 (H)-oxo-1,3-thiazol-2-yl)-amino]benzoate (HH33)

(0.43 g, 70% yield); m.p.=234-235° C.; $R_f$=0.2 (hexane/ethyl acetate; 2/1); $^1$H NMR (400 MHz, DMSO-d6) δ=10.41 (br. S, 1H, NH), 7.86, 7.04 (2*d, J(H,H)=4.8 Hz, 1H; ArH-4), 7.60 (s, 1H; CH═C), 7.577.24 (m, 5H, Ph, ArH-6), 6.83-6.57 (m, 1H; ArH-3), 3.92, 3.88 (2*s, 3H; $OCH_3$), 3.00, 2.95 (2*s, 6H, $NMe_2$), 2.30 (s, 3H, Me). $^{13}$C NMR (100 MHz, DMSO-d6) δ=180.20, 169.87, 169.13, 164.67, 151.53, 132.05, 131.76, 125.61, 124.00, 121.87, 114.01, 112.55, 53.11, 53.05, 52.99, 21.17.

HH32 and HH33 Compounds Preparation

Stock solutions of HH32 and HH33 compounds were prepared in 100% Dimethyl sulfoxide (DMSO) (Sigma Aldrich, Missouri, USA) and the working solutions of compounds didn't exceed 0.1% DMSO.

Cell Lines and Culture Conditions

Eight different cancer cell lines were acquired from the Radiobiology and Experimental Radio Oncology lab, University Medical Center, Hamburg University, Hamburg, Germany. MCF7, MDA-MB-231 (breast cancer), and A549 (lung cancer) cells were maintained in RPMI medium while HCT116 (colon cancer), HepG2 (liver cancer), U87, U373 (glioblastoma), and HeLa (cervical cancer) were maintained in DMEM supplemented with 10% FBS and 1% penicillin/streptomycin (Sigma Aldrich, Missouri, USA). Normal human fibroblast (F180) cells were maintained in DMEM supplemented with 15% FBS. Normal human mammary epithelial cell line (HME1) were maintained in DMEM/F-12 medium supplemented with 10% FBS. All incubations were done at 37° C. in a humidified atmosphere of 5% CO2. All cell lines were authenticated by short tandem repeat (STR)

profiling. The CDK4 knockout cells (provided by Dr. Samrein Ahmed, University of Sharjah, United Arab Emirates) were generated by CRISPR-CAS9 technology and were maintained in DMEM supplemented with 10% FBS.

CRISPR-CAS9 for Knocking Out CDK4 in HCT116 Colon Cancer Cells

CRISPR-Cas9 was employed to stablish HCT116 CDK4 KO cells. Ribonucleotide protein (RNP) delivery system for CRISPR technique was utilized. All the reagents were purchased for Thermoscientific company, USA. gRNA was used to target CDK4 genes. Lipofectamine™ CRISPR-MAX™ Cas9 Transfection Reagent was used to transfect the cells with the gRNA and Cas9. The genomic cleavage efficiency was assessed by immunoblotting, while a scrambled gRNA, Trueguide gRNA Negative control, was used as a negative control in all the steps to ensure the specificity of the target. The pool of cells that showed highest transfection efficiency was considered for the downstream validation. To generate isolated clones with complete knockout, the mixed pool of cells was diluted 1 cell/200 μl liquid medium and then dispersed into 96 wells plate. The individual cells were left to form clones. The clones were tested for the expression of CDK4 via immunoblotting.

Cell Lysis, Protein Quantification and Western Blot

Figure 5:
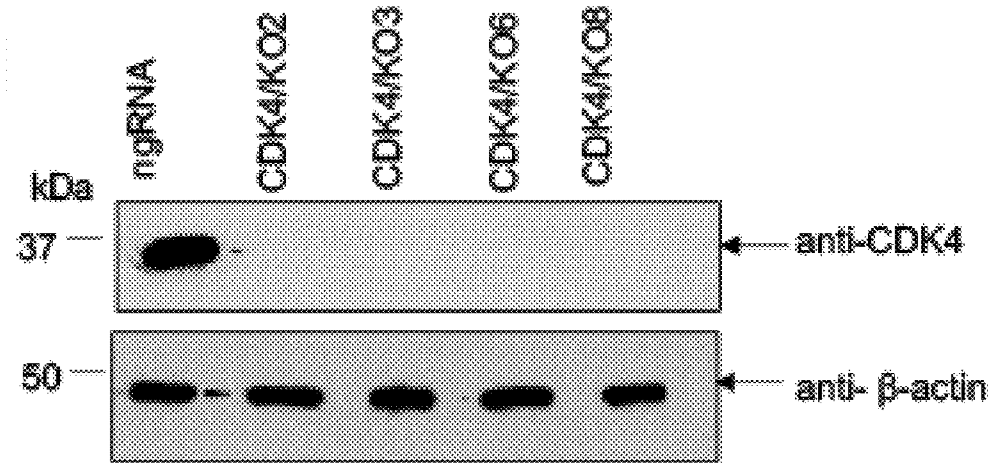
FIG. 5 provides Western blot analysis showing CDK4 knockout in HCT116 colon cancer KO cells in lanes 2-4. Lane 1 shows gRNA negative control. Housekeeping protein β-actin was used to normalize the levels of protein detected by confirming that protein loading is the same across the gel.

Cell lysates were obtained via using 1% triton Lysis buffer (TLB) cocktail supplemented with PMSF, 100 mM NaVo3, 1M NaF and Protease inhibitor cocktail. Subsequently, the lysates were centrifuged at 14000 g for 20 min at 4° C. The protein concentrations, from the attained supernatant, were determined using the ThermoScientific Pierce BCA Protein Assay Kit. The cell lysates were diluted in 2X Laemelli's buffer solution, which was followed by 5 min heating at 95° C. Total protein (10 μg/lane) were separated on 10% SDS-poly-acrylamide gels and then transferred on to nitrocellulose membranes (Amersham, Germany). The membranes were blocked for 1 hr at room temperature using 5% BSA. Followed by incubation with the primary antibody against CDK4 (Cell signaling, Rabbit) overnight at 4° C. All primary antibodies were used at a 1:1000 dilution. The following day, the membrane was washed three times with 1XTBST and then incubated with secondary antibody (Anti-Rabbit Antibody). The blots were then visualized employing the ECL™ Prime Western Blotting System GE Healthcare, and imaged using ChemiDoc™ Touch Imaging System (Bio-Rad). The housekeeping protein β-actin was used to normalize the levels of protein detected by confirming that protein loading is the same across the gel (FIG. 5).

Cytotoxicity Assay

The cytotoxic effects of HH32 and HH33 compounds were evaluated at various concentrations ranging from 0.0001 to 100 μM by sulphrhodamine-B (SRB) assay as described previously [30]. The anti-proliferative activity was expressed as growth inhibitory concentration (IC50) values, which were calculated by the sigmoidal dose-response curve fitting method using Graph pad prism 6 software (GraphPad Software, San Diego, CA, USA).

Transcriptomic Analysis

MCF7 and A549 cells were harvested after treatment with IC50 doses of HH33 compound for 24 hours (0.81 μM for MCF7 and 2.93 μM for A549). RNA extraction was carried out followed by cDNA synthesis using SuperScript VILO cDNA Synthesis kit (Invitrogen, Waltham, MA, USA) and amplification using Ion AmpliSeq gene expression core panel primers. The prepared library was purified using Agencourt AMPure XP beads (Beckman Coulter, California, USA) and quantified using Ion Library TaqMan™ Quantitation Kit (Applied Biosystems, Waltham, MA, USA). The libraries were further diluted to 100 pM and pooled equally with four individual samples per pool. The pooled libraries were amplified using emulsion PCR on Ion OneTouch™ 2 instrument (OT2) and the enrichment was performed on Ion OneTouch™ ES following the manufacturer's instruction. Thus, prepared template libraries were then sequenced with Ion S5 XL Semiconductor sequencer using the Ion 540™ Chip. RNA-seq data were analyzed using Ion Torrent Software Suite version 5.4 and the alignment was carried out using modifications of the Torrent Mapping Alignment Program (TMAP) optimizing it for aligning the raw sequencing reads against reference sequence derived from hg19 (GRCh37) assembly. The specificity and sensitivity was maintained by implementing a two-stage mapping approach by employing BWA-short, BWA-long, SSAHA [31], Super-maximal Exact Matching [32] and Smith Waterman algorithm [33] for optimal mapping. Raw read counts of the targeted genes were performed using Samtools (Samtools view -c -F 4-L bed_file bam_file) and the number of expressed transcripts was confirmed after Fragments Per Kilobase Million (FPKM) normalisation. Differentially expressed gene (DEG) analysis was performed using a script written in R programming language (version 3.6.3) with function calls to DESeq2 package from Bioconductor library sets. Raw read counts from RNASeq were normalized using quantile normalization. All counts ranked "0" were excluded. Differentially expressed genes between the two set of cell lines [HH33-treated (n=3), and untreated (n=3)] were assessed using 2 tailed t-test. Differentially expressed genes with p-value of <0.05, adjusted p-value<0.8 and 5-fold difference were included for pathway analysis using Metascape.

Western Blot

The protein expression analysis was done after treatment with 0.5 or 1 μM of HH32 and HH33 compounds for 24 hours by western blot [8]. Cell lysates were prepared using lysis buffer containing 20% SDS, glycerol, 1M Tris (pH 6.8) and supplemented with protease and phosphatase inhibitors (Sigma Aldrich, Missouri, USA). The proteins were separated by SDS-PAGE and transblotted into nitrocellulose membrane (Biorad, Hercules, CA, USA). Membrane were incubated overnight at 4° C. with the following primary antibodies: γH2AX, H2Ax, p21, CDC2, CDC25c, cyclin B, c-Myc, Bid, ATM, p-ATM, ATR, p-ATR, Chk1, p-Chk1, Chk2, p-Chk2, caspase 9, caspase 8, pRb (Ser807/811) (Cell Signaling Technology, Massachusetts, USA), p53, cyclin A, cyclin E, cyclin D1, CDK2, Rb, pRb (Ser249) (Santa Cruz Biotech, Texas, USA) and β-actin (Sigma Aldrich, Missouri, USA). Membranes were then incubated with respective mouse/rabbit secondary antibody (Cell Signaling Technology, Massachusetts, USA) for 1 hour at room temperature and detected by enhanced chemiluminescence (ECL) (Biorad, Hercules, CA, USA) method using Chemi Doc imaging system (Biorad, Hercules, CA, USA). The protein bands were quantified using Image lab™ software (Biorad, Hercules, CA, USA).

Neutral Comet Assay

MCF7, HCT-116 and A549 cells were treated with 0.5 or 1 μM of HH32 or HH33 compounds for 24 hours and control cells were treated with vehicle (DMSO). A group of cells was treated with doxorubicin as a reference drug using the same treatment conditions. Comet assay was performed in neutral condition to detect DNA double-strand breaks using comet assay kit (Trevigen Inc., Maryland, USA) according to the manufacturer's instructions. The tail moment, which reflect the amount of DNA damage in each nucleus, was calculated in at least 50 cells using OpenComet software.

Cell Cycle Analysis

The effect of the HH32 and HH33 compounds on the distribution of cell cycle at different time points (2, 4, 8, 24, 48, and 72 hours) was analyzed using flow cytometry [34]. Briefly, the cells were harvested and fixed in 70% ethanol for 24 hours at −20° C. The fixed cells were treated with RNAase (100 μg/ml) (Sigma Aldrich, Missouri, USA) and stained with propidium iodide (50 μg/ml) (Sigma Aldrich, Missouri, USA). The data were acquired using BD Accuri C6 flow cytometer (Becton Dickenson, San Jose, CA, USA) and analysis was done using Flow Jo software (Tree Star, Inc, Ashland, OR, USA).

Apoptosis Analysis

The cells were collected at 12, 24 and 48 hours after treatment with 0.5 or 1 μM of HH32 and HH33 compounds. The detection of early and late apoptotic cell death was done using FITC Annexin V Apoptosis Detection Kit (Becton Dickenson, California, USA) according to the manufacturer's protocol [35]. The data were analyzed by BD Accuri C6 flow cytometer (Becton Dickenson, New Jersey, USA).

Molecular Docking Studies

Molecular docking studies were performed employing the program Autodock vina [36]. X-ray crystal structures for the proteins under study, namely; Cdc25C, CDK1/Cyclin-B1, CDK2/Cyclin-A and retinoblastoma tumor suppressor (Rb) protein were downloaded from Protein Data Bank (http://www.rcsb.org/pdb/) under the entry codes of, 3OP3, 4Y72, 6GUE and 1O9K, respectively. Complexed inhibitors and water molecules were extracted from their initial X-ray structures. Later, Autodock Tools (MGL Tools 1.5.6rc2) were utilized for adding polar hydrogens and generating Gasteiger charges. The compounds under study were treated employing the same mentioned procedure. Additionally, grid boxes were established to cover the active site on each macromolecule, with a spacing of 1.0 Å between the grid points, centered towards their respective coordinates. The exhaustiveness and the number of poses were set to 14 and 10 respectively.

Statistical Analysis

The data were described as mean±standard error of the mean (SEM) of at least three independent experiments. Unpaired student t-test was used to compare HH32/HH33—treated samples to DMSO-treated samples. p-value<0.05 was considered statistically significant. All statistical calculations were done by GraphPad Prism 6 (GraphPad Software, San Diego, CA, USA).

Metabolic Analysis

The release of different metabolites following HH32 and HH33 treatment on MCF7 cells was detected using Gas Chromatography-Mass Spectrometry (GC-MS) (Shimadzu, Kyoto, Japan) as was described previously [37]. GC-MS analysis was performed using a QP2010 gas chromatography-mass spectrometer (GC-2010 coupled with a GC-MS QP-2010 Ultra) equipped with an auto-sampler (AOC-20i+s) from Shimadzu (Tokyo, Japan), using Rtx-5 ms column (30 m length×0.25 mm inner diameter×0.25 μm film thickness; Restek, Bellefonte, PA, USA). Helium (99.9% purity) was used as the carrier gas with the column flow rate of 1 mL/min. Data collection and analysis were performed using MSD Enhanced Chemstation software (Shimadzu, Kyoto, Japan). GC total ion chromatograms (TIC) and fragmentation patterns of the compound were identified using the NIST/EPA/NIH Mass Spectral Library (NIST 14).

Preprocessing and data analysis were performed using an in-house R script. Only compounds registered in Human Metabolome Database (HMDB 4.0) [38] were considered for further analysis. Compounds with more than 70% of missing values were considered unreliable and therefore excluded. Probabilistic Quotient Normalization [39] was used to normalize data due to dilution effects in the extraction procedure. Missing metabolite measurements were imputed using the k-nearest neighbor algorithm [40] with k=3. Student t-test was used to identify significantly (p<0.05) altered metabolites for each drug. To account for multiple testing, a false discovery rate (FDR) of <15% was applied to reduce the identification of false positives. FDRs were calculated using the q conversion algorithm [41, 42] in multiple comparisons. Principal component analysis (PCA) was used to visualize the metabolomic data. Data were mean-centered and scaled to unit variance before PCA.

RESULTS

Figure 6A:
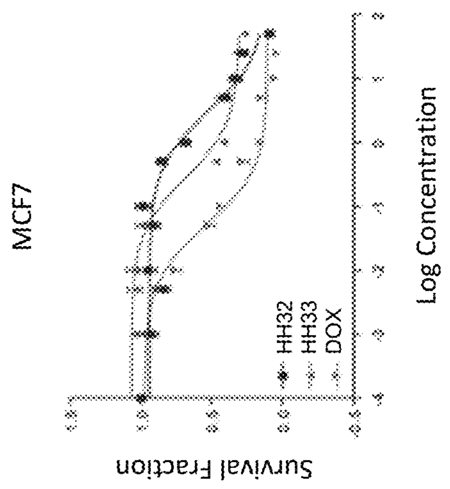
FIGS. 6A-6J provides an evaluation of anti-proliferative effect of HH32 and HH33 on a variety of cancer cell lines.
Figure 6B:
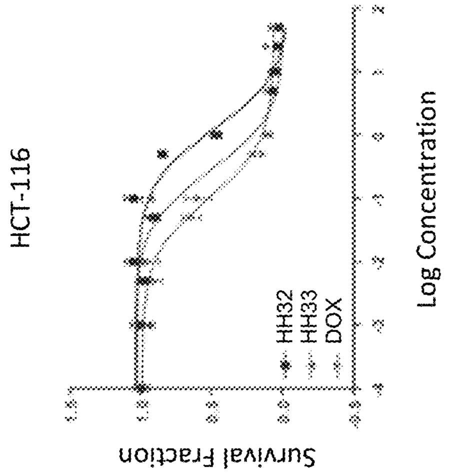
Figure 6C:
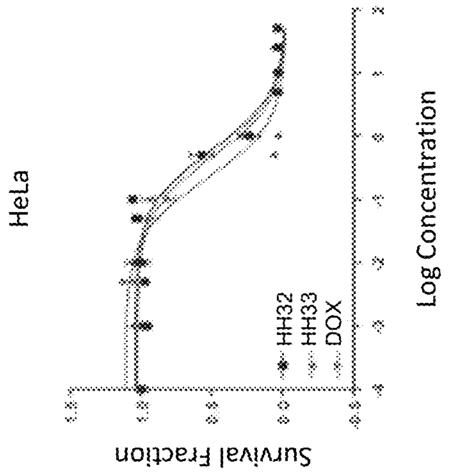
Figure 6D:
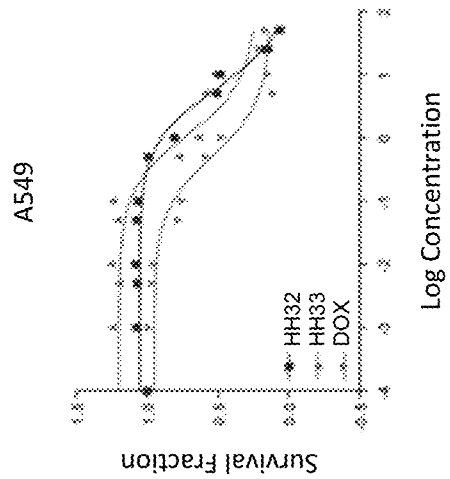
Figure 6E:
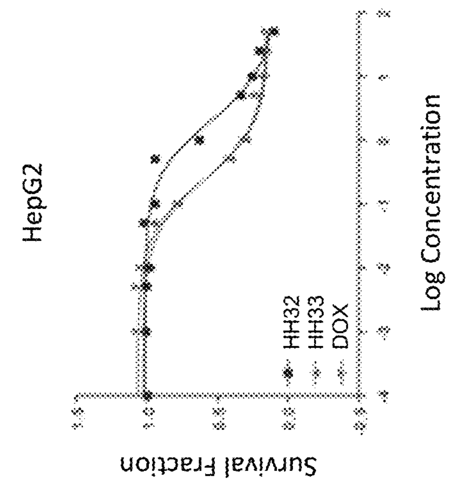
Figure 6F:
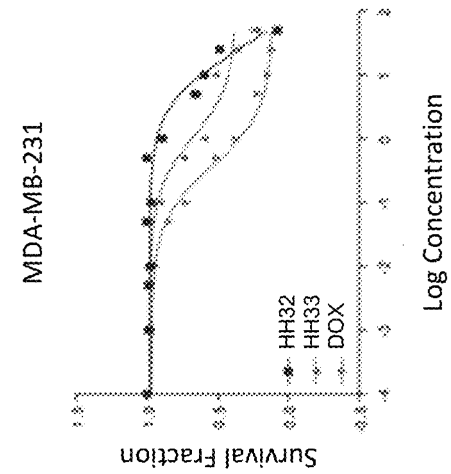
Figure 6G:
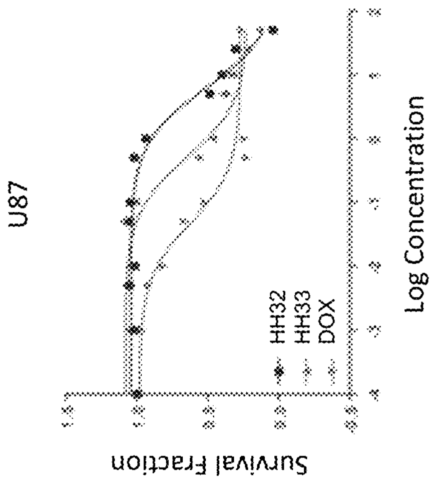
Figure 6H:
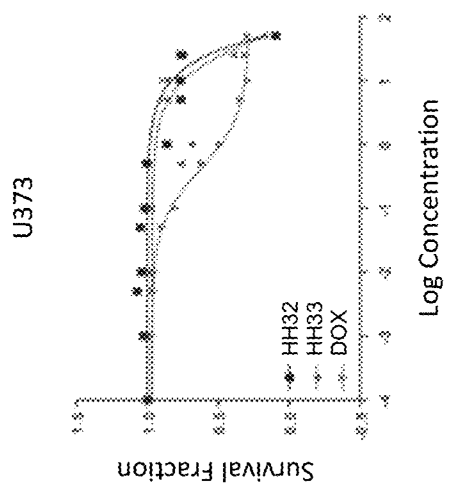
Figure 6I:
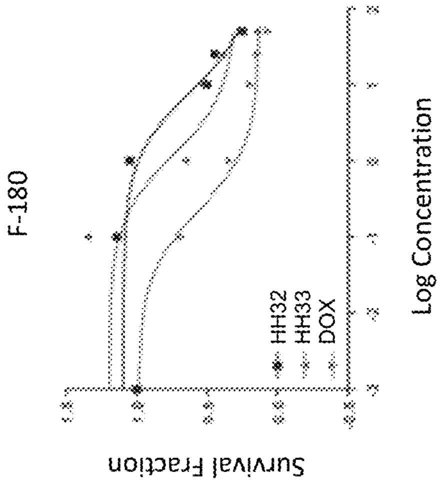
Figure 6J:
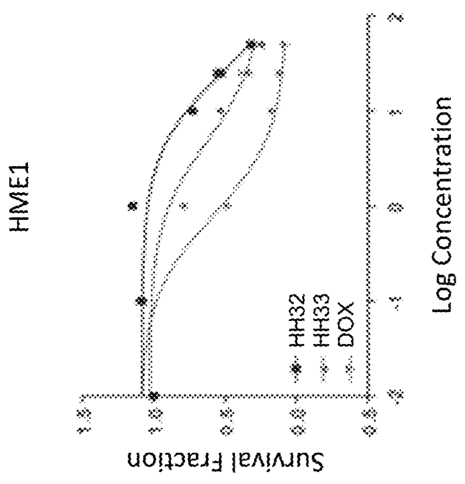

Acetylated 5-aminosalicylate-thiazolinone Hybrid Derivatives Exhibited Cytotoxicity Towards Cancer Cells Both HH32 and HH33 compounds induced a remarkable concentration-dependent decrease in the viability of the eight tested cancer cell lines (FIGS. 6A-6A, Table 1). The results in Table 1 show that HH13 derivative exhibited higher anti-proliferative effects than HH32. In particular, four cell lines (MCF7, HeLa, HCT-116 and HepG2) were highly sensitive to the HH33 with an IC50 values less than 1 μM, whereas the other four cell lines (A549, MDA-MB-231, U78 and U373) showed an IC50 greater than 1 μM. The HH33 was nearby equipotent to the reference drug doxorubicin in HCT-116 cells and displayed a superior activity than doxorubicin in HeLa cells. Furthermore, the selectivity of HH32 and HH33 towards cancer cells was tested by investigating their anti-proliferative effects on normal cells (F180 and HME1) (FIGS. 6I-6J). The two tested compounds demonstrated lower cytotoxicity against both normal fibroblast and epithelial cells indicated by higher IC50s (>13 μM for HH32 and >3.9 μM for HH33) compared to doxorubicin (<1.2 μM) (Table 1). To get more insight on the selectivity of the HH32 and the HH33 compounds, the selectivity index of both compounds was calculated and found to be superior in most of cancer cell lines than doxorubicin [43] (Table 2). Collectively, these results demonstrate that HH32 and HH33 have potent anti-proliferative activity against various types of cancer cells with low impact on normal cells.

TABLE 1

Antiproliferative activities of HH32 and HH33 in comparis onto Doxorubicin in cancer and normal cells lines by IC50

IC50 (μM)

| | MCF7 | HCT-116 | HeLa | A549 | HepG2 |
|---|---|---|---|---|---|
| HH32 | 3.44 ± 0.32 | 1.17 ± 0.46 | 0.60 ± 0.47 | 6.17 ± 0.38 | 2.49 ± 0.11 |
| HH33 | 0.81 ± 0.34 | 0.29 ± 0.47 | 0.24 ± 0.51 | 2.93 ± 0.83 | 0.38 ± 0.11 |
| DOX | 0.06 ± 0.38 | 0.11 ± 0.41 | 0.46 ± 0.46 | 0.62 ± 0.59 | 0.37 ± 0.12 |

TABLE 1-continued

Antiproliferative activities of HH32 and HH33 in comparis onto Doxorubicin in cancer and normal cells lines by IC50
IC50 (μM)

| | MDA-MB-231 | U87 | U373 | F-180 | HME1 |
|---|---|---|---|---|---|
| HH32 | 15.35 ± 0.08 | 6.53 ± 0.09 | 29.38 ± 0.08 | 13.34 ± 0.38 | 26.79 ± 0.14 |
| HH33 | 3.94 ± 0.08 | 1.03 ± 0.11 | 23.66 ± 0.08 | 3.91 ± 0.43 | 9.25 ± 0.14 |
| DOX | 0.45 ± 0.11 | 0.10 ± 0.09 | 0.88 ± 0.09 | 0.29 ± 0.37 | 1.12 ± 0.19 |

*Represented data are means ± SEM of at least 3 independent experiments.

TABLE 2

Selectivity index of HH32 and HH33 compounds compared to selectivity index of Doxorubicin

| | F180 | | | HME1 | | |
|---|---|---|---|---|---|---|
| | HH32 | HH33 | Doxoru-bicin | HH32 | HH33 | Doxoru-bicin |
| MCF7 | 3.88 | 4.89 | 4.8 | 7.8 | 11.4 | 18.7 |
| HCT116 | 11.4 | 13.48 | 2.6 | 22.9 | 31.9 | 10.2 |
| HeLa | 22.2 | 16.3 | 0.6 | 44.65 | 38.5 | 2.4 |
| A549 | 2.16 | 1.3 | 0.47 | 4.3 | 3.2 | 1.81 |
| HepG2 | 5.36 | 10.3 | 0.78 | 10.8 | 24 | 3.02 |
| MDA-MB-231 | 0.87 | 0.99 | 0.64 | 1.7 | 2.3 | 2.5 |
| U87 | 2.04 | 3.8 | 2.9 | 4.1 | 9 | 11.2 |
| U373 | 0.45 | 0.17 | 0.33 | 0.9 | 0.4 | 1.3 |

Transcriptomic Analysis of HH33-Treated Cells

Figure 7A:
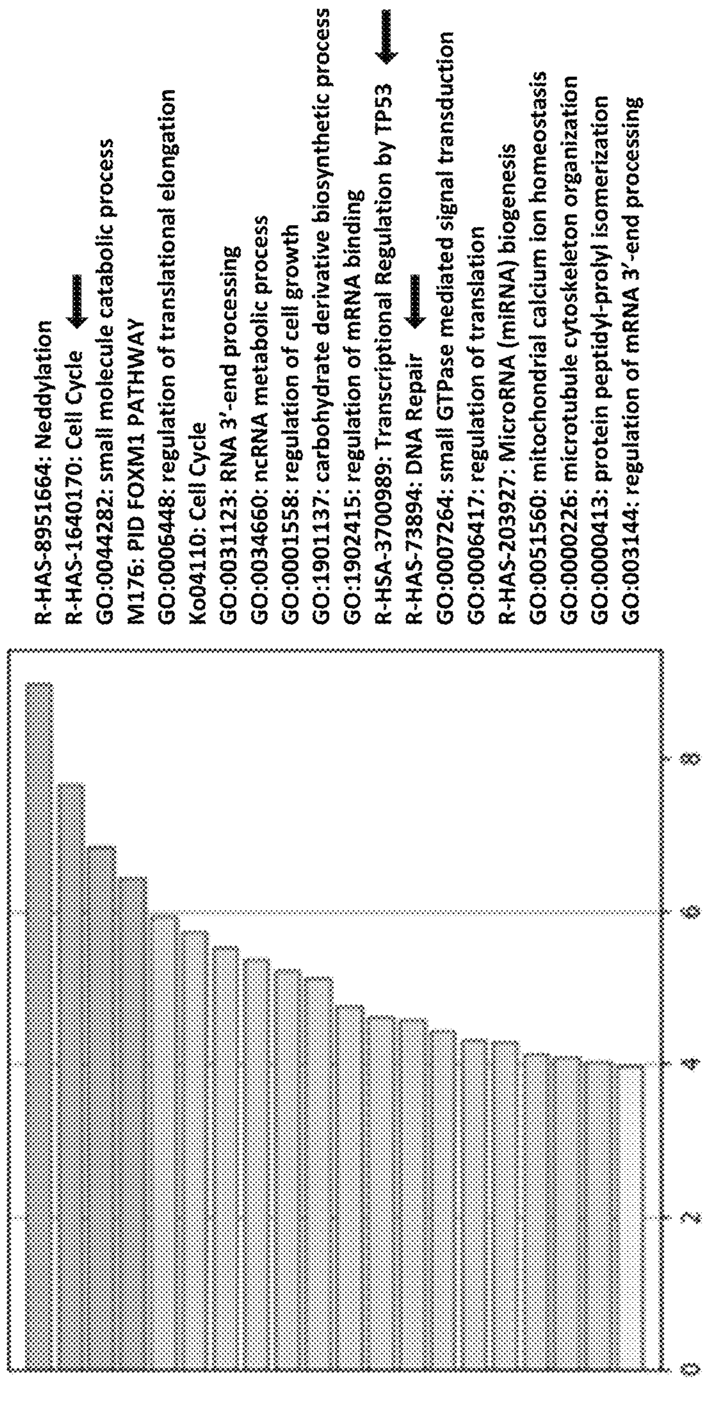
FIGS. 7A-7D provides transcriptomic analysis of HH33-treated MCF7 and A549 cells.
Figure 7B:
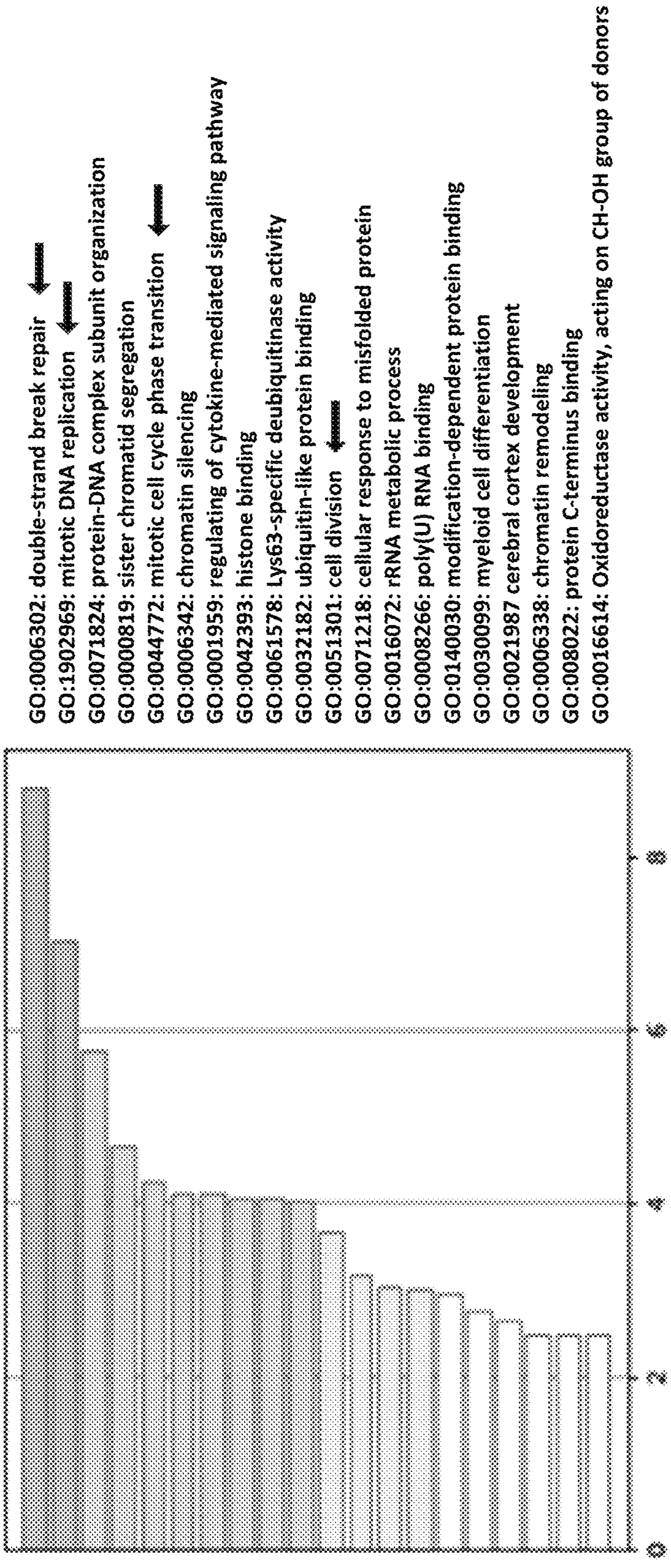
Figure 7C:
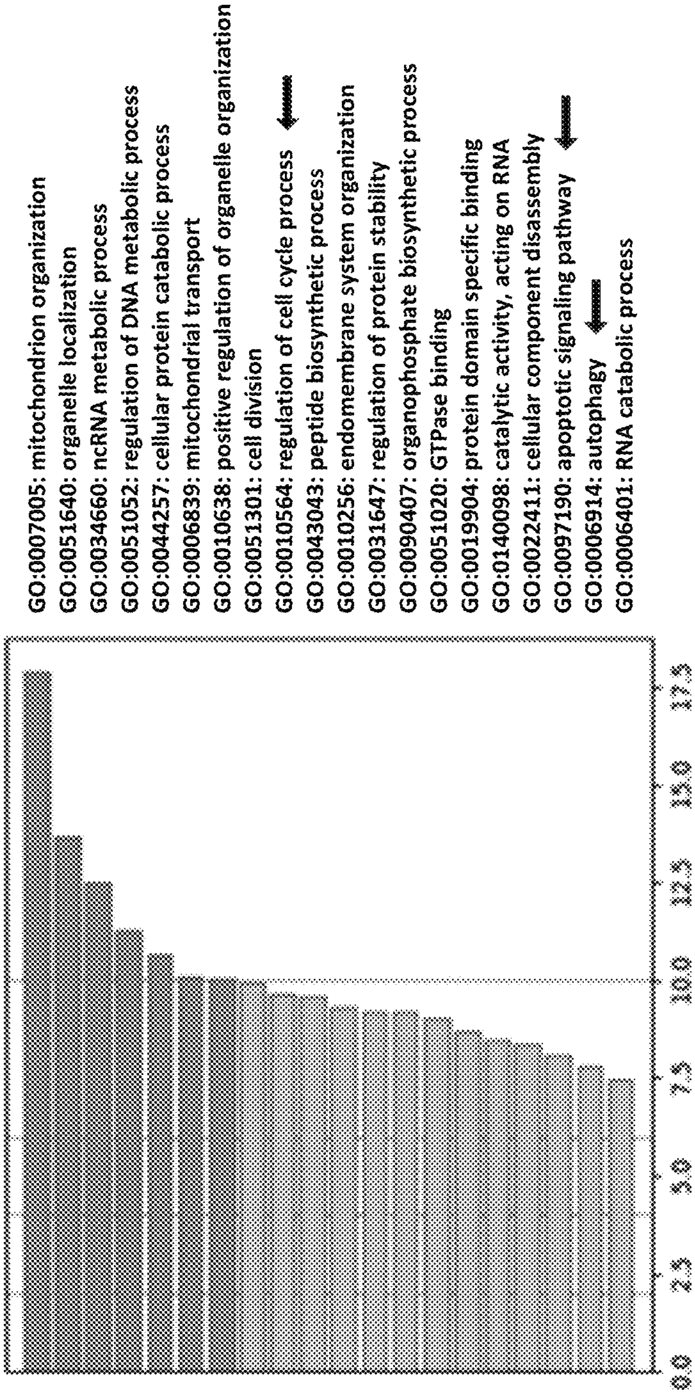
Figure 7D:
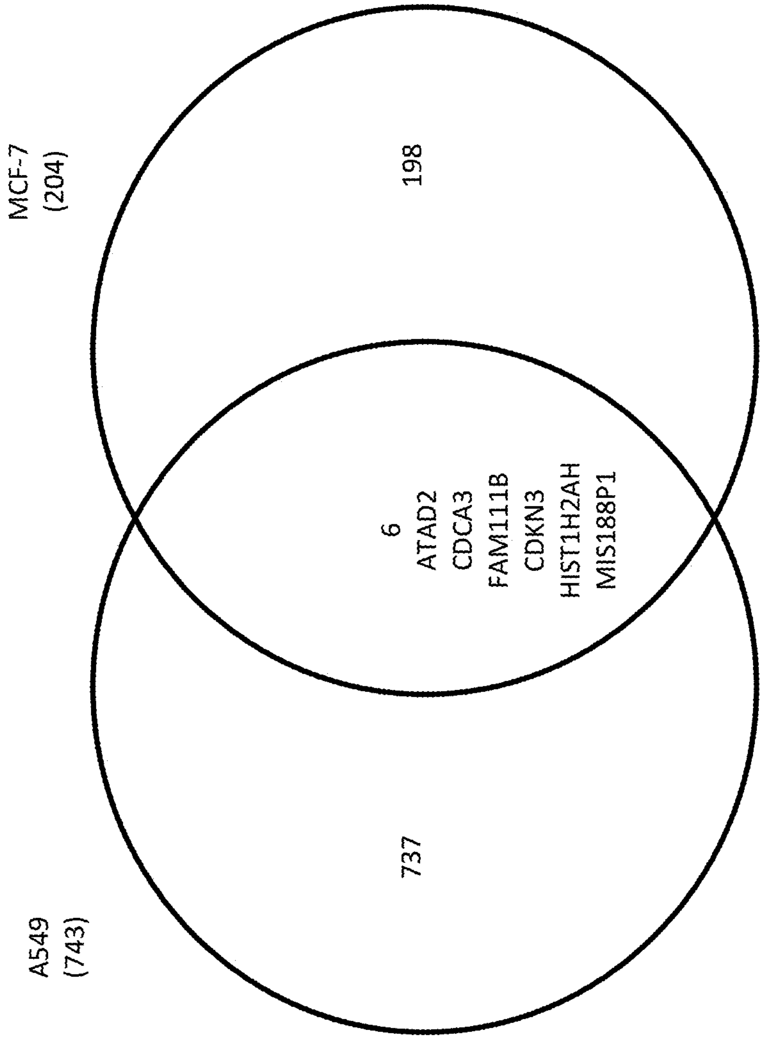
Figure 8A:
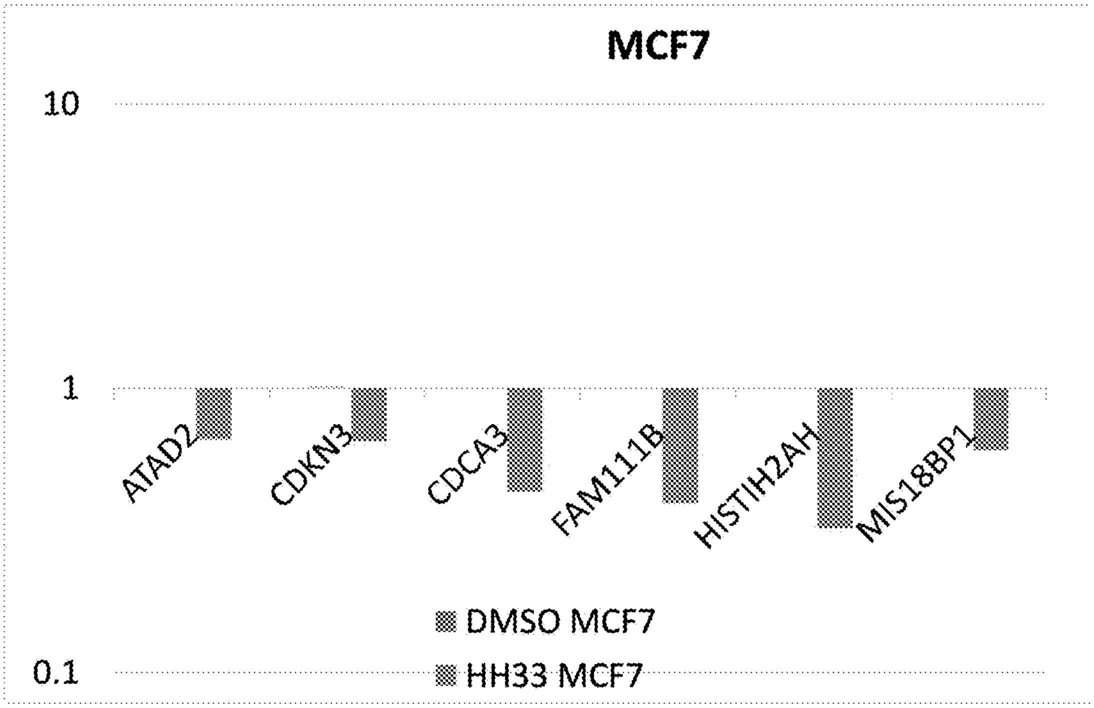
FIGS. 8A-8B provides validation of transcriptomics analysis for HH33-treated MCF7 and A549 cells. The mRNA expression of six top downregulated genes in FIG. 8A MCF7 and FIG. 8B A549 cells was analyzed by quantitative Real-time PCR after treatment with 1 μM of HH-33 compound.
Figure 8B:
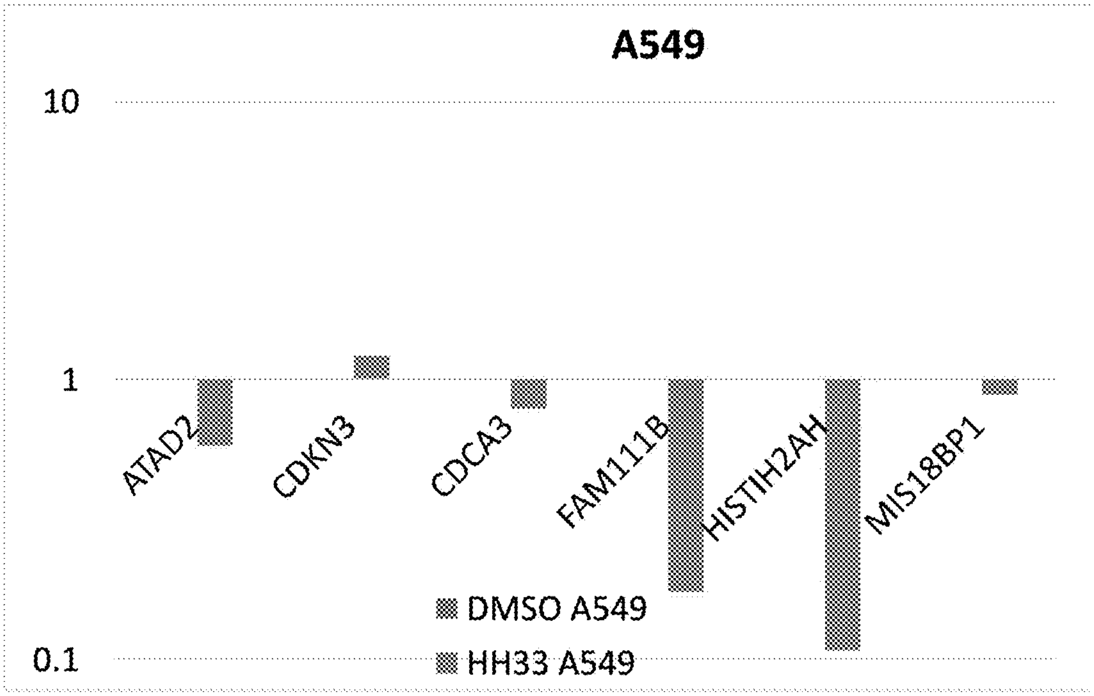
Figure 9A:
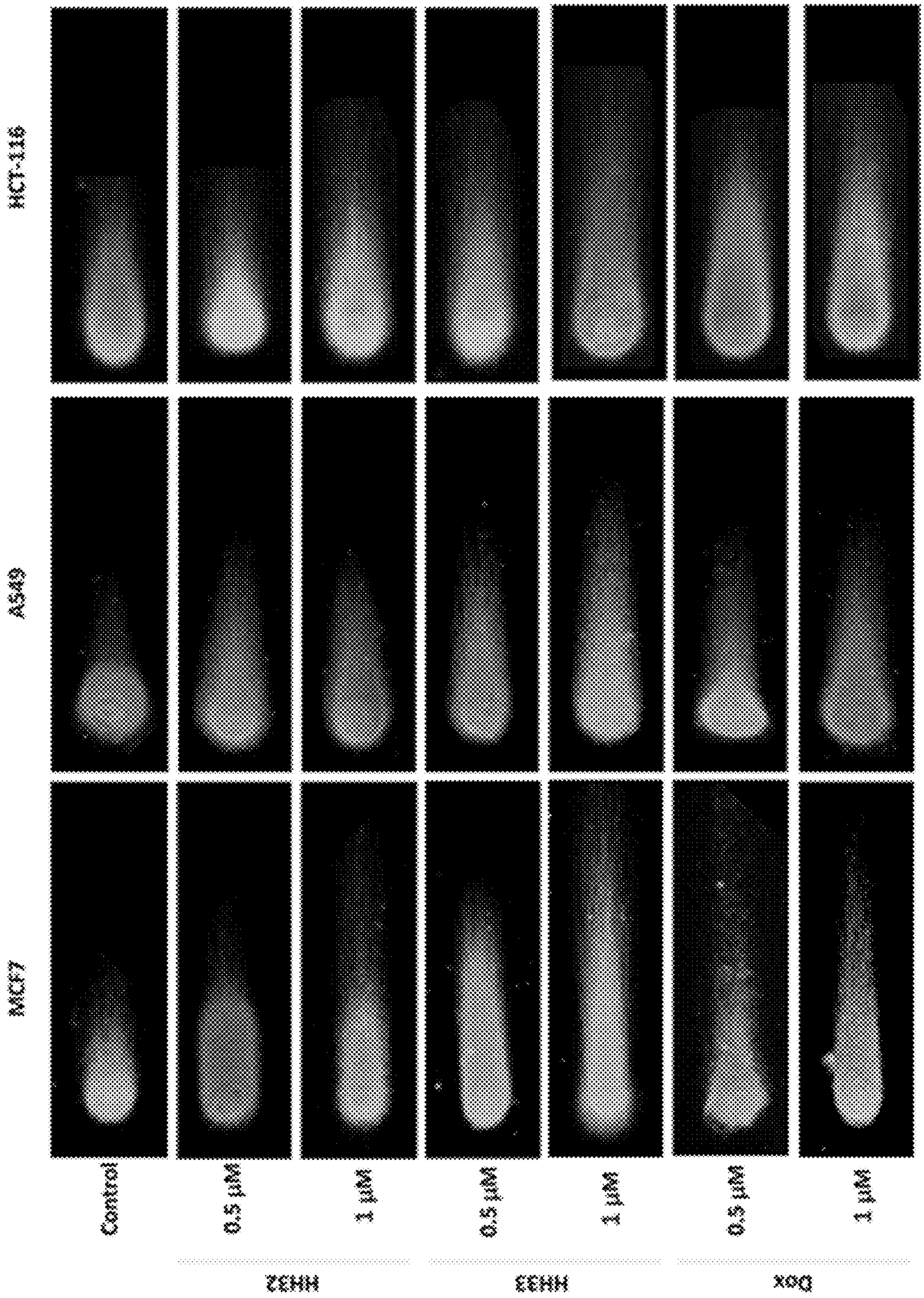

To get an insight into the mechanism of action and the possible pathways targeted by our compounds, transcriptomic analysis of the MCF7 (representing sensitive cells) and A549 (representing resistant cells) has been investigated after treatment with HH33 compound. HH33 was selected because it showed better anti-proliferative activities than the HH32. Hypergeometric test of HH33-treated MCF7 cells showed down-regulation of pathways related to DNA repair and cell cycle progression. (FIG. 7*a*, Table 3). On the other hand, treatment of A549 cells with HH33 induced an upregulation of apoptotic signaling pathway and down-regulation of cell cycle progression pathway (FIG. 7*b,c*, Table 4). Of note, transcriptomics analysis of HH33-treated MCF7 and A549 cells showed six shared genes (ATAD2, CDCA3, FAMIIIB, CDKN3, HISTIH2AH, MIS18BP1) that were maximally downregulated in both cell lines and were confirmed by quantitative RT-PCR (FIG. 7*d*, FIG. 8, Table 5). To validate the results of transcriptomic analysis, we studied the effect of HH32 and HH33 compounds on DNA damage induction, activation of DNA damage response (DDR) machinery, effects on cell cycle progression and induction of apoptosis.

TABLE 3

Maximum downregulated genes in DNA repair pathway identified from the transcriptomic analysis of H33-treated A549 and MCF7 cells compared to DMSO-treated cells:
DNA Repair pathways

| Gene | Fold change (H_Mean/D_Mean) |
|---|---|
| A549 | |
| ACTR8 | 0.011392 |
| CLSPN | 0.017984 |

TABLE 3-continued

Maximum downregulated genes in DNA repair pathway identified from the transcriptomic analysis of H33-treated A549 and MCF7 cells compared to DMSO-treated cells:
DNA Repair pathways

| Gene | Fold change (H_Mean/D_Mean) |
|---|---|
| EYA3 | 0.025961 |
| BARD1 | 0.045105 |
| CHEK2 | 0.059432 |
| MCF7 | |
| CDC45 | 0.142612 |
| POLA1 | 0.196005 |
| RECQL | 0.21203 |
| MMS22L | 0.214449 |
| UBE2W | 0.224026 |
| RAD51 | 0.250450 |
| RNF168 | 0.260475 |
| ESCO2 | 0.27193 |
| RAD51AP1 | 0.287719 |
| GTF2H2C | 0.290698 |
| RAD17 | 0.300292 |
| ZSWIM7 | 0.314371 |
| RIF1 | 0.316619 |
| UBE2N | 0.368758 |
| MCM6 | 0.419495 |
| TRIP13 | 0.443614 |
| DDX11 | 0.496124 |
| CHAF1B | 0.525108 |
| RNF111 | 0.533113 |
| PIAS4 | 0.696133 |

TABLE 4

Maximum upregulated genes in apoptosis pathway and maximum downregulated genes in Cell cycle and the related TP53 regulation pathways identified from the transcriptomic analysis of H33-treated A549 cells compared to DMSO-treated cells.

| Gene | Fold change* |
|---|---|
| Apoptosis | |
| TNFRSF10C | 802.5000 |
| CRIP1 | 199.5714 |
| BECN1 | 186.7500 |
| YWHAH | 168.8804 |
| TGFB1 | 100.8000 |
| Cell Cycle | |
| BARD1 | 0.045105 |
| ODF2 | 0.005902 |
| CDC14A | 0.014254 |
| CEP78 | 0.016145 |
| CLSPN | 0.017984 |
| Transcriptional Regulation by TP53(19) | |
| CCNE1 | 0.020935 |
| CDK9 | 0.022616 |
| BARD1 | 0.045105 |

TABLE 4-continued

Maximum upregulated genes in apoptosis pathway and maximum downregulated genes in Cell cycle and the related TP53 regulation pathways identified from the transcriptomic analysis of H33-treated A549 cells compared to DMSO-treated cells.

| Gene | Fold change* |
|---|---|
| COX16 | 0.046656 |
| CSNK2A2 | 0.058772 |

*H33-treated A549 cells/DMSO-treated A549 cells central to the DDR, which results in the phosphorylation and subsequent activation of downstream proteins such as ChK1, ChK2, p53, BRCA½ to stop cell cycling and to allow for DNA repair or for activation of cell death pathways. Treatment of MCF7, HeLa, HCT116, and A549 cells with HH32 and HH33 compounds resulted in a marked elevation of the level of p-H2Ax (γ-H2Ax), a well-reported marker for DNA damage (FIGS. 10A-10D In particular, the HH33 resulted in higher elevation of the γ-H2Ax than the HH32 compound (FIGS. 10A-10C). On the other hand, the two compounds did not induce the formation of γ-H2Ax in the A549 cell line indicating low level of DNA damage and/or

TABLE 5

Maximally downregulated genes shared by HH33-treated MCF7 and A549 cells, with annotation

| Gene | Annotation |
|---|---|
| ATAD2 | ATAD2 belongs to the AAA ATPase family. It is likely a transcriptional coactivator of the nuclear receptor ESR1 required to induce the expression of a subset of estradiol target genes, such as CCND1, MYC and E2F1. It may play a role in the recruitment or occupancy of CREBBP at some ESR1 target gene promoters. It is involved in the estrogen-induced cell proliferation and cell cycle progression of breast cancer cells. |
| CDCA3 | Cell division cycle associated 3 is a cell division cycle-associated protein 3; F-box-like protein which is required for entry into mitosis. It acts by participating in E3 ligase complexes that mediate the ubiquitination and degradation of WEE1 kinase at G2/M phase. |
| FAM111B | This gene encodes a protein with a trypsin-like cysteine/serine peptidase domain in the C-terminus. Mutations in this gene are associated with an autosomal dominant form of hereditary fibrosing poikiloderma (HFP). Affected individuals display mottled pigmentation, telangiectasia, epidermal atrophy, tendon contractures, and progressive pulmonary fibrosis. Alternative splicing results in multiple transcript variants encoding distinct isoforms. A paralog of this gene which also has a trypsin& #8208; like peptidase domain, FAM111A, is located only 16 kb from this gene on human chromosome 11q12.1. [provided by RefSeq, April 2014]. |
| CDKN3 | Cyclin-dependent kinase inhibitor 3; May play a role in cell cycle regulation. Dual specificity phosphatase active toward substrates containing either phosphotyrosine or phosphoserine residues. It dephosphorylates CDK2 at 'Thr-160' in a cyclin-dependent manner. This gene was reported to be deleted, mutated, or overexpressed in several kinds of cancers. Alternatively, spliced transcript variants encoding different isoforms have been found for this gene. [provided by RefSeq, August 2008]. |
| HIST1H2AH | Histone2A clustered histone 12 gene is intronless and encodes a replication-dependent histone that is a member of the histone H2A family. Transcripts from this gene lack polyA tails but instead contain a palindromic termination element. This gene is found in the histone microcluster on chromosome 6p21.33. [provided by RefSeq, August 2015]. |
| MIS18BP1 | MIS18-binding protein 1; Required for recruitment of CENPA to centromeres and normal chromosome segregation during mitosis; Myb/SANT domain containing |

HH32 and HH33 are Potent DNA Damage Inducers

Results of the transcriptomic analysis pointed out the ability of our compounds to target cellular DNA. To verify these results, we used neutral comet assay to detect the DNA damaging potential of our compounds in MCF7, HCT-116 and A549 cells. As shown in FIGS. 9A-9D, the level of DNA damage as indicated by the comet tail length and intensity (tail moment) was increased after treatment with HH32 and HH33 in a concentration-dependent manner in the three cell lines. Notably, comet length was markedly higher in HH33-treated cells than HH32-treated cells in both MCF7 and HCT-116 cells FIGS. 9A-9D. Interestingly, the level of DNA double strand breaks induced by treatment with 1 μM of HH33 was higher than doxorubicin treatment using the same concentration in the three tested cell lines. These results clearly demonstrated the capability of HH32 and HH33 to target the cellular DNA inducing extensive DNA damage.

HH32 and HH33 Activates DNA Damage Response Machinery

Figure 10E:
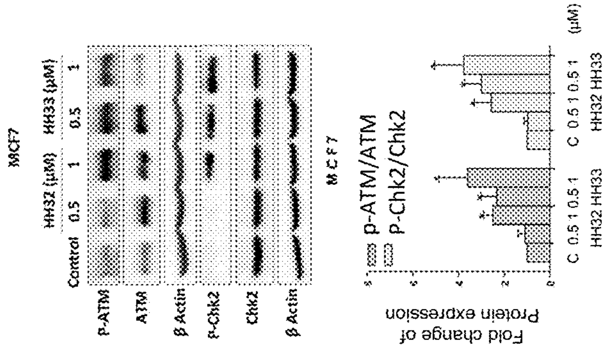
Figure 10F:
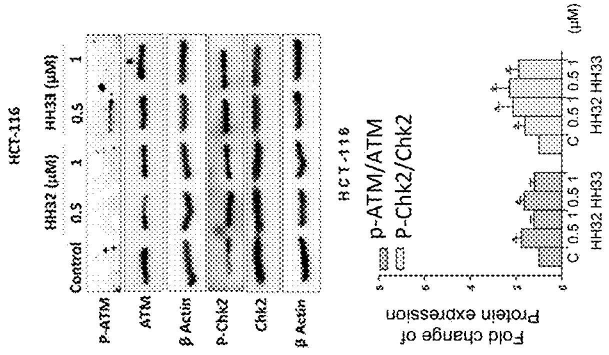
Figure 10G:
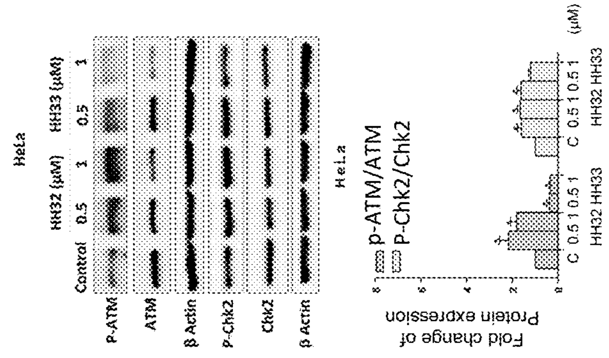
Figure 10H:
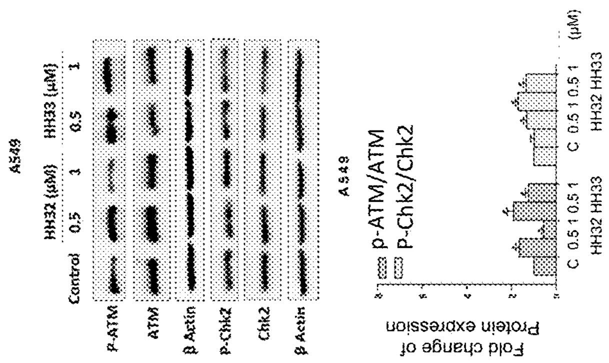
Figure 10I:
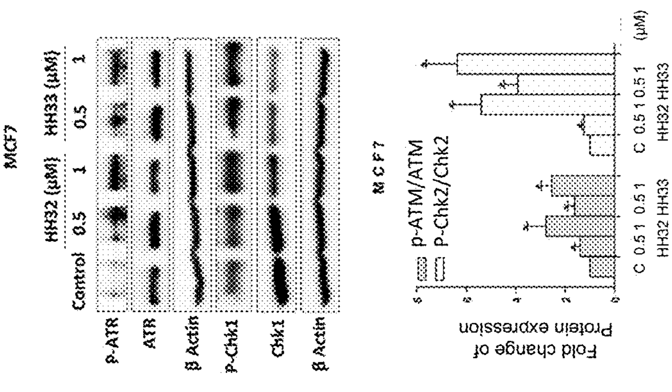
Figure 10J:
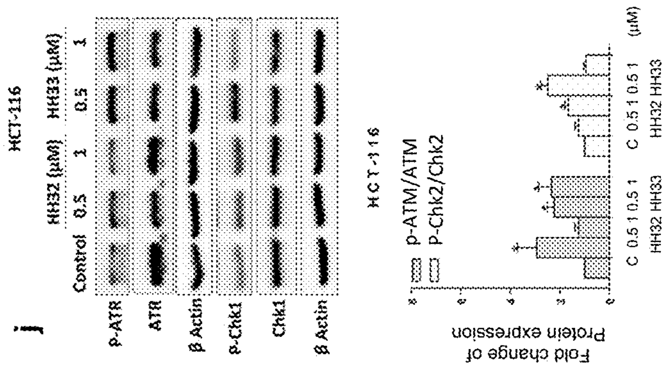
Figure 10K:
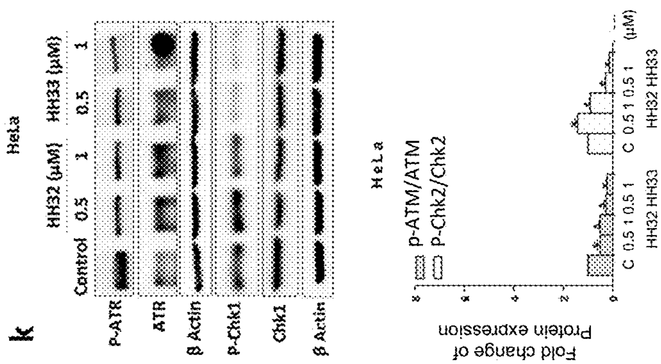
Figure 10L:
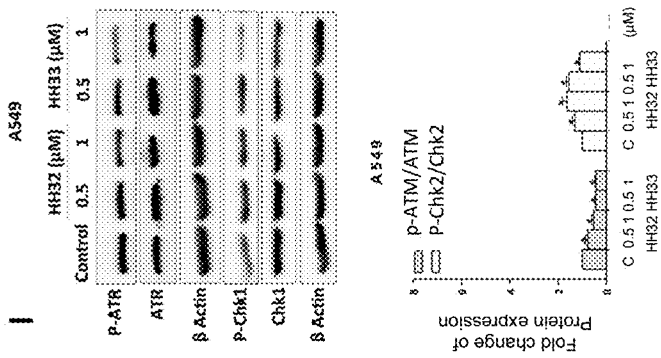

Induction of DNA damage activates a network of proteins called DNA damage response machinery (DDR). Phosphorylation of H2Ax histone in the area surrounding the damaged sites is an early event indicating DNA damage. Activation of the signal transducer kinases ATM and ATR is efficient DNA repair (FIG. 10D). As illustrated in FIG. 10E, the phosphorylation status of ATM and its downstream target Chk2 increased significantly by HH32 and HH33 in MCF7, HCT-116 and A549 cells while only by HH32 treatment in HeLa cells (FIGS. 10F-10H). Similar results were seen for the activation of ATR/Chk1 cascade under the same treatment conditions with HH32 and HH33 in the four cell lines (FIGS. 10I-10L). These data indicate that HH32 and HH33 induce DNA damage and activate ATM/Chk2 and ATR/Chk1 signaling pathways.

HH32 and HH33 Induce Cell Cycle Arrest at G2/M Phase

Figure 11A:
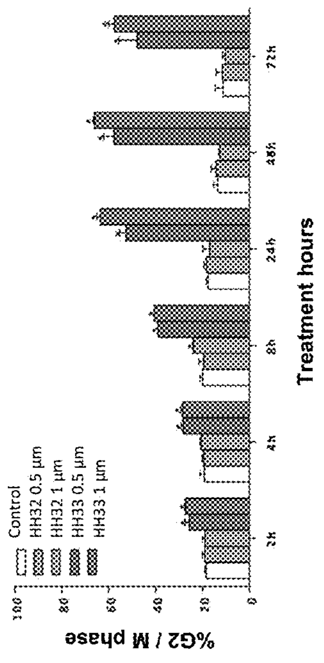
FIGS. 11A-11P provides HH32 and HH33 induction of G2/M phase arrest accompanied with accumulation in the sub-G1 phase.
Figure 11B:
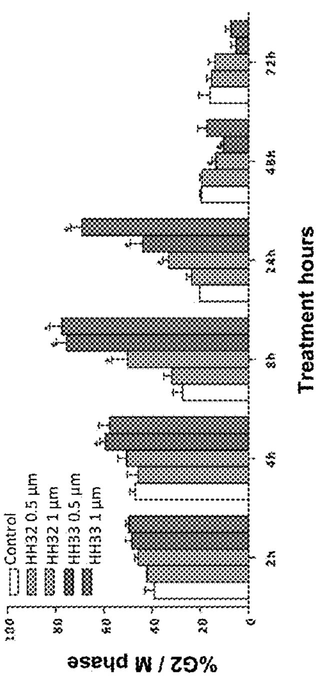
Figure 11C:
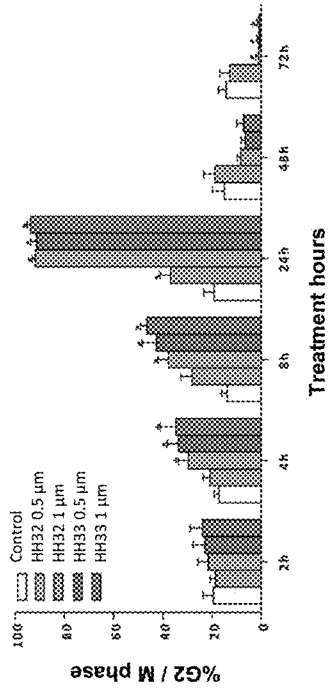
Figure 11D:
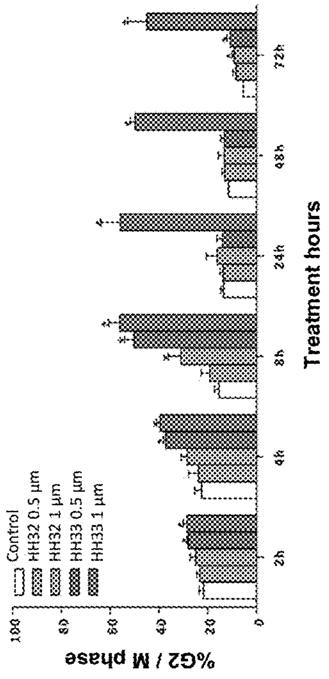
Figure 11O:
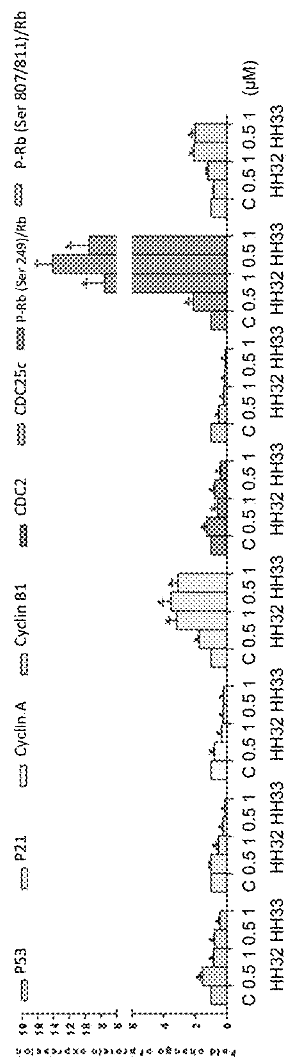
Figure 11P:
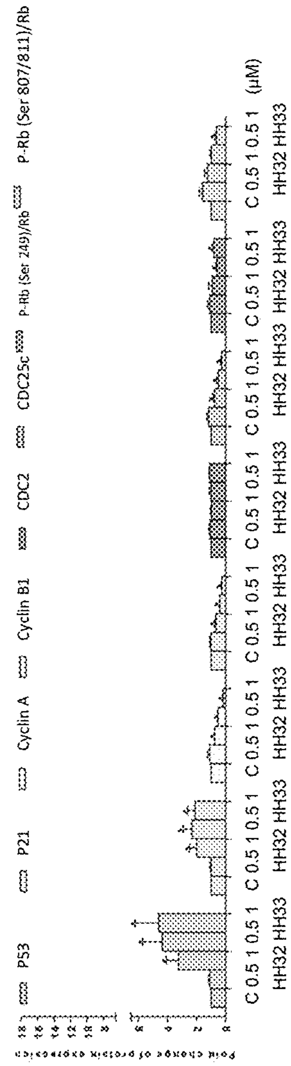
Figure 11K:
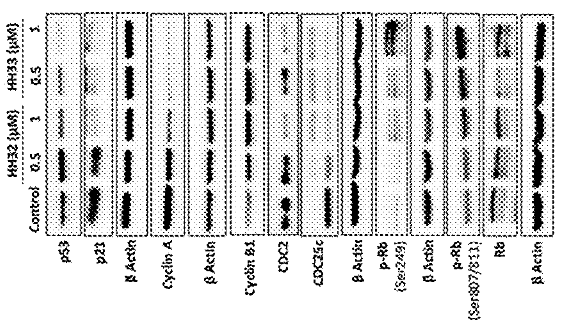
Figure 11L:
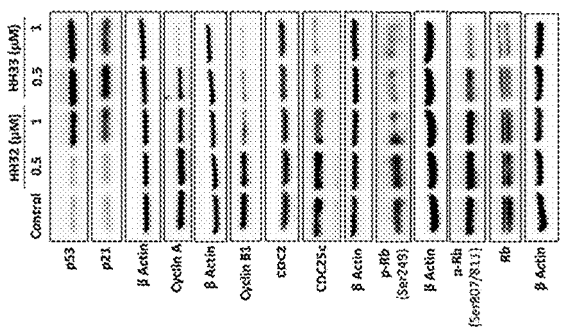
Figure 12A:
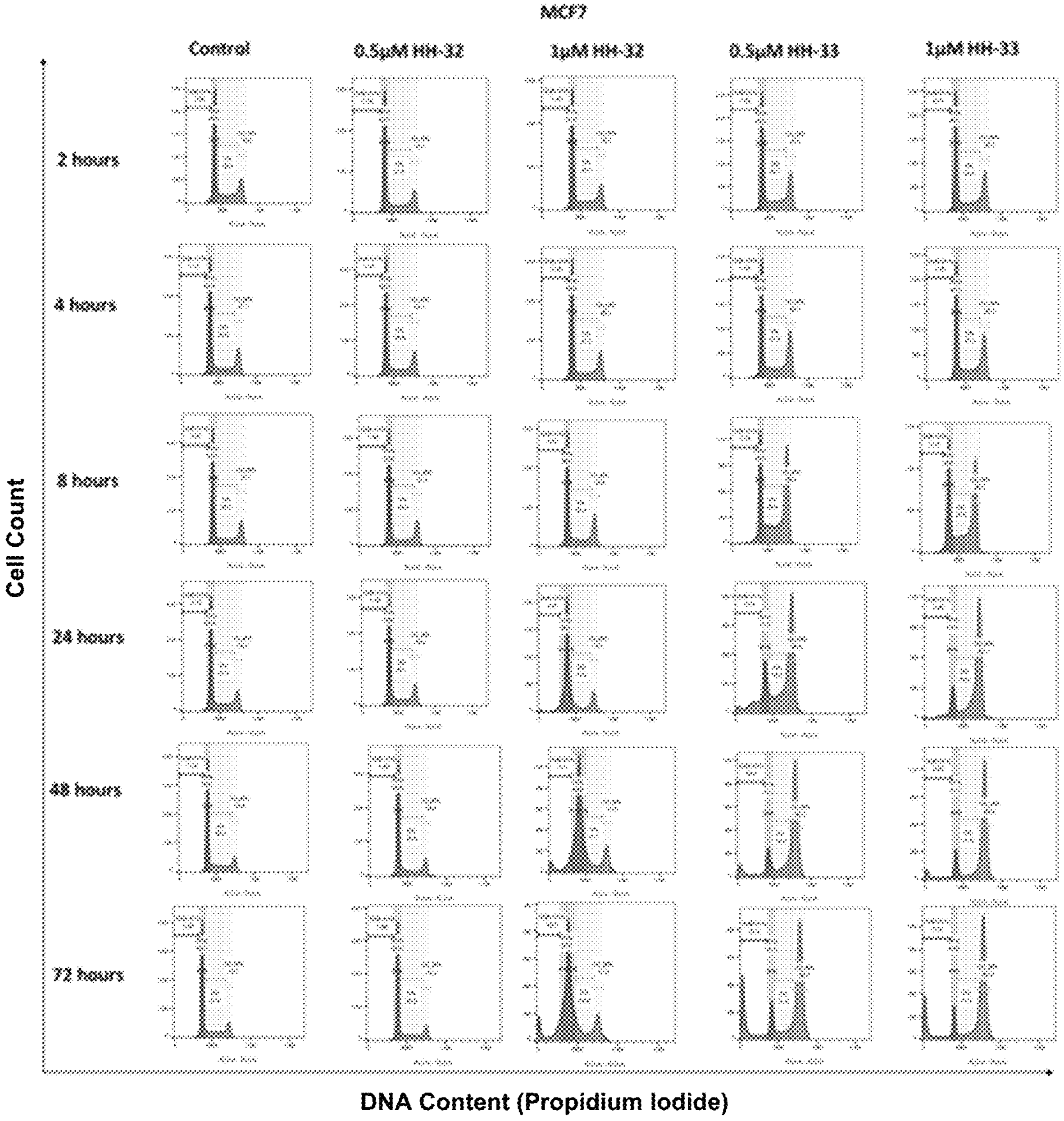
FIGS. 12A-12D provides cell cycle analysis after HH32 and HH33 treatment.
Figure 12B:
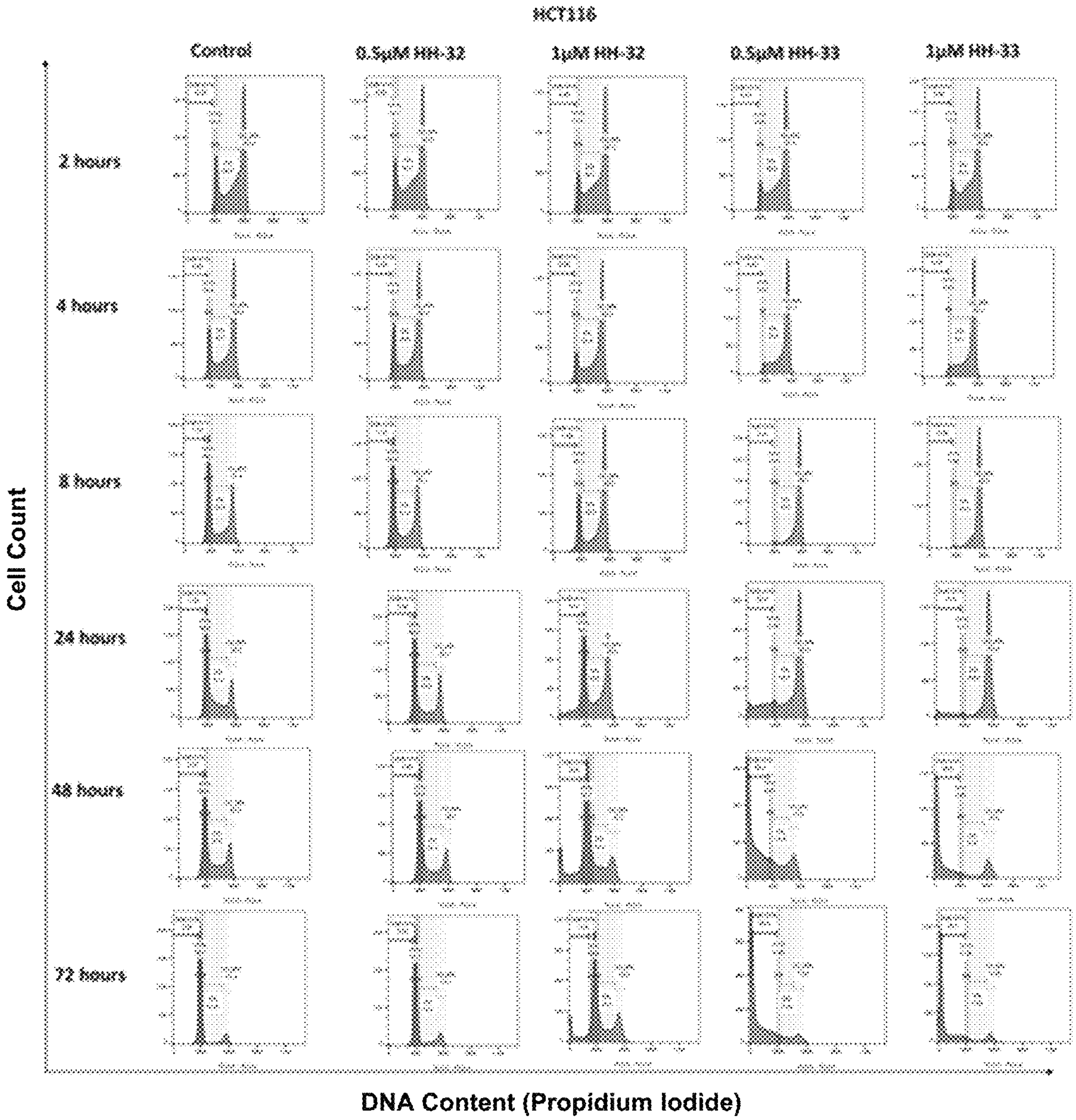
Figure 12C:
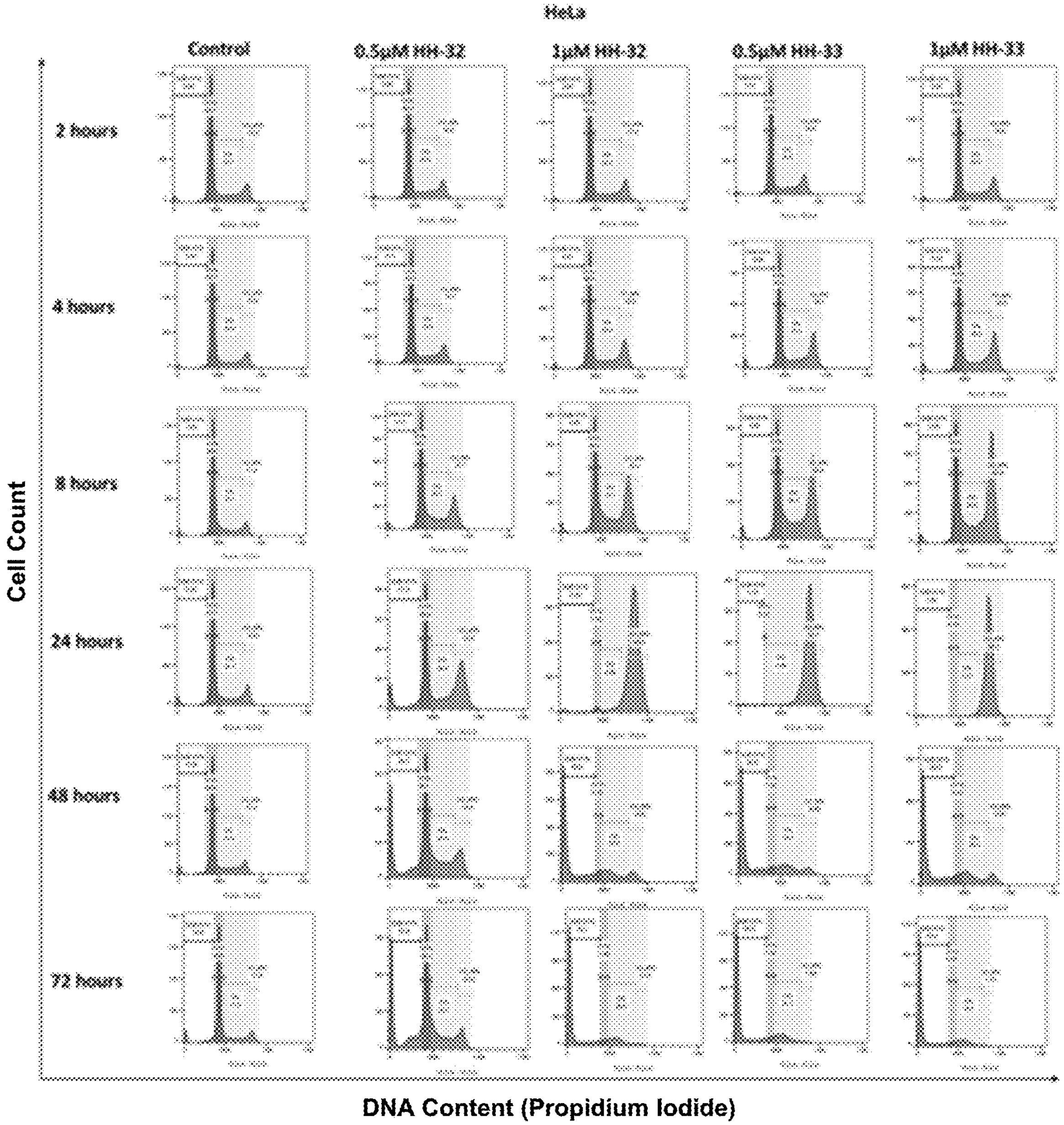
Figure 12D:
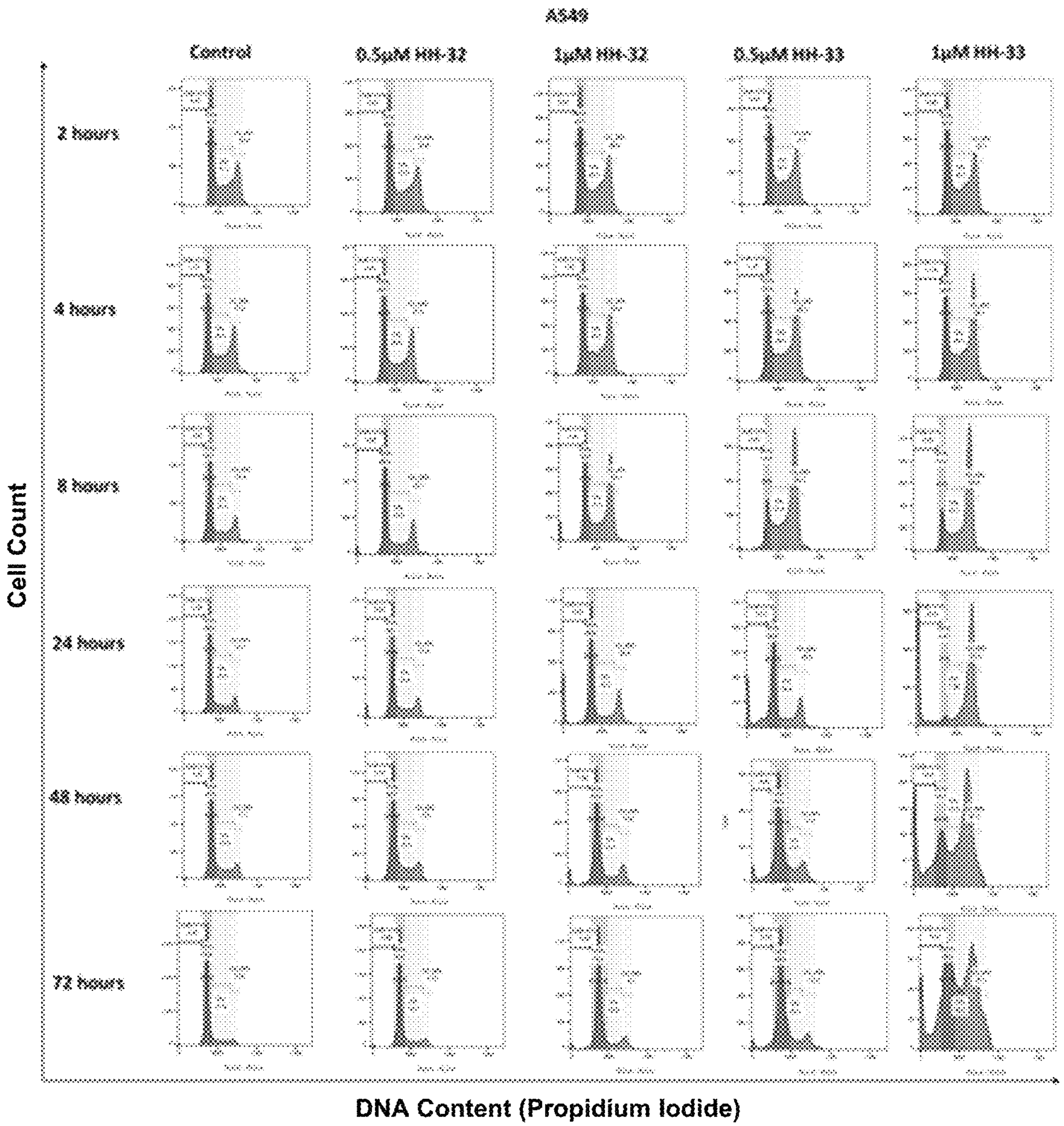
Figures 13A, 13B, 13C, 13D:
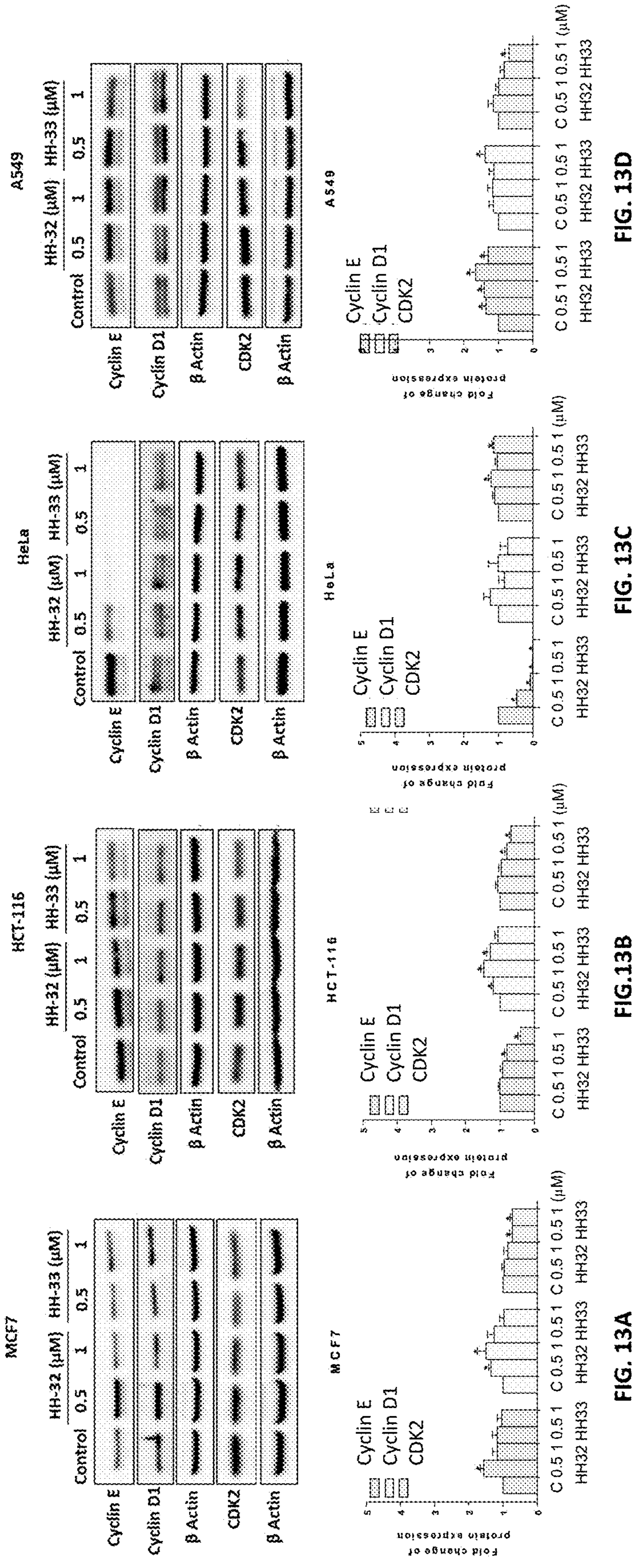
FIGS. 13A-13D provides Western blot analysis for G1/S phase regulatory proteins after HH32 and HH33 treatment.
Figure 14D:
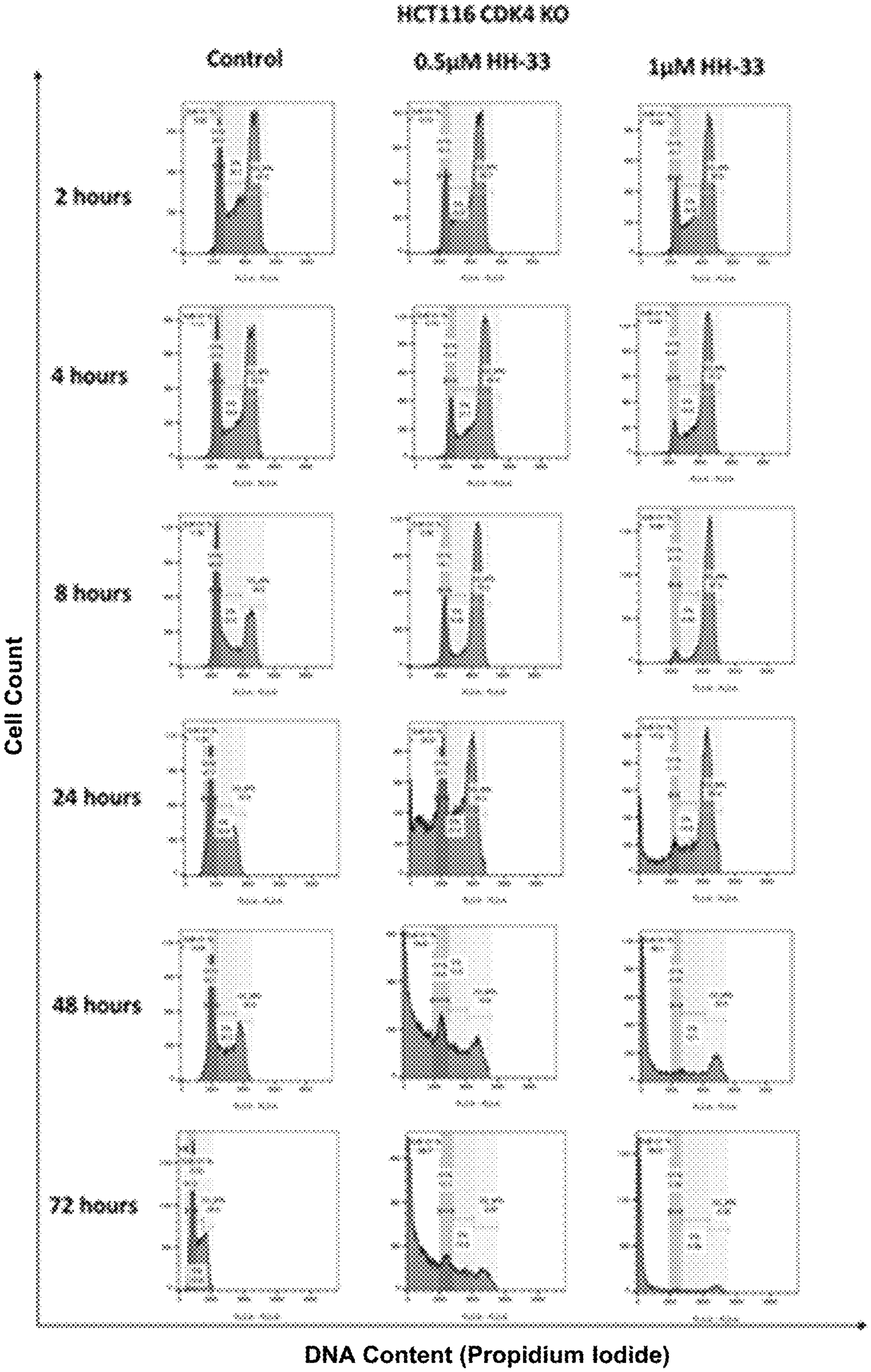
Figure 14E:
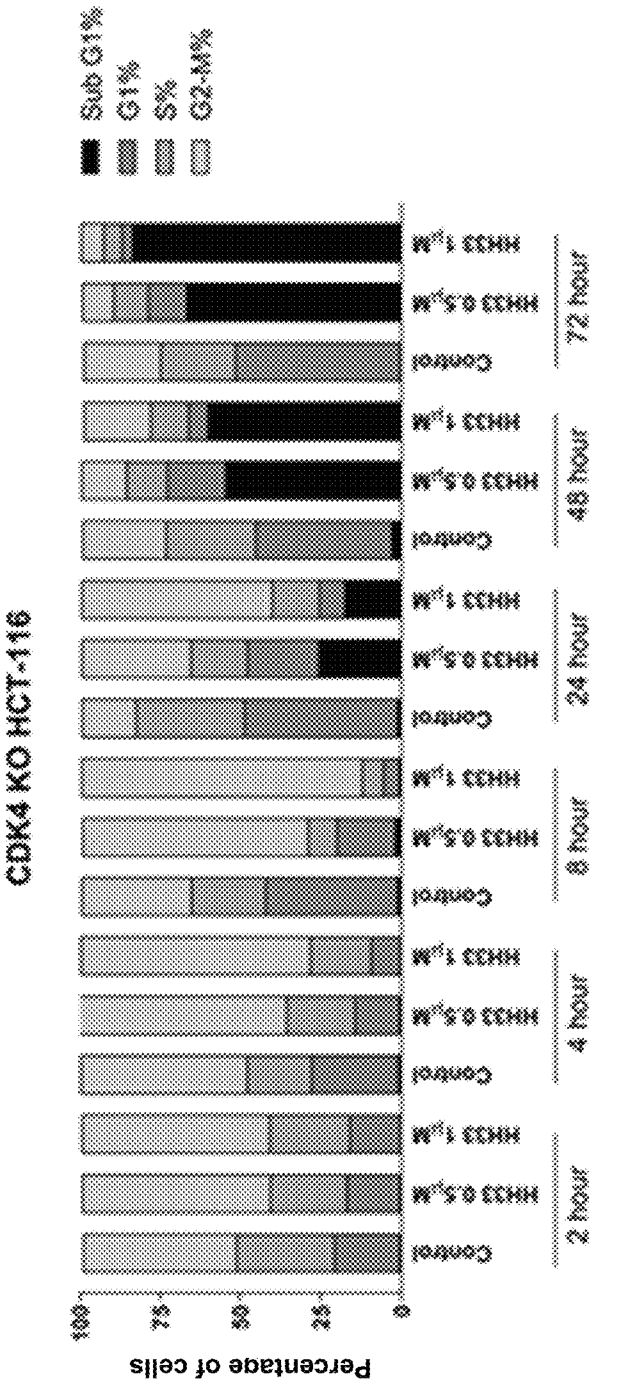

The cell growth inhibition and the induction of DNA damage are often linked to dysregulation of cell cycle machinery. In this regard, we studied the effects of HH32 and HH33 on cell cycle distribution at various time intervals (FIGS. 11A-11D, FIGS. 12A-12D). The two compounds induced a significant arrest of the cells at the G2/M phase in the four cell lines at different time points (FIGS. 11A-11D). In cells treated with 1 μM of HH33, G2/M phase accumulation peaked at 8 hours in HCT116 (Control 27.4%, HH33 77.4%) and at 24 hours in HeLa cells (Control 36.9%, HH33 93.9%). On the other hand, treatment with HH33 resulted in strong G2/M cell cycle arrest in MCF7 and A549 cells in a time-dependent manner and it was maintained up to 72 hours (MCF7: Control 11.3%, 1 μM HH33 57.7%; A549: Control 8.5%, 1 μM HH33 45.1%) (FIGS. 11A-11D). Interestingly, the arrest of all cell lines in G2/M phases was accompanied with the appearance of a substantial sub-G1 cell population particularly in HCT116 and HeLa cells, reflecting the increase in DNA fragmentation, which indicates apoptotic cells (FIGS. 11E-11H). However, no signs of G1 and S phases arrest were observed in the four cell lines following HH32 or HH33 treatment (FIGS. 13A-13D). In agreement with the flow cytometry analysis of cell cycle, HH33 was more effective than HH32 in reducing the expression of proteins involved in the G2/M phase progression (cyclin A, cyclin B, CDC25c and CDC2/CDK1) (FIGS. 11I-11L). On the other hand, the cyclins and cyclin-dependent kinases (cyclin E, cyclin D1 and CDK2), which are involved in G1-S phase transition, were slightly changed after HH32 and HH33 treatment (FIGS. 14A-14E). Moreover, we tested the anti-proliferative activity and the effects on cell cycle of the HH33 on CDK4 knockout HCT116 cells. Since CDK4 is known to be involved in regulating passage of cells through G1 and S phases but not G2/M phases [44, 45], our results showed no difference in the sensitivity nor the cell cycle distribution between wild-type and CDK4 knockout cells after treatment with HH33 (FIGS. 15A-15D) The function of cyclin/cyclin-dependent kinase (CDK) complex in cell cycle progression is negatively regulated by CDK inhibitors such as p53 and p21, which were reported to contribute to G2/M phase arrest. Both HH32 and HH33 substantially increased the expression of p53 and p21 in MCF7, HCT-116 and A549 cells while both markers were reduced in HeLa cells (FIGS. 11M-11P). Furthermore, we used two phospho-retinoblastoma (Rb) antibodies (ser-249 and ser807/811) to investigate the effects of our two compounds on the phosphorylation of Rb, which acts as cell cycle control checkpoint. The two compounds induced reduction in Rb phosphorylation (ser-249 and ser807/811) in MCF7 and A549 cells (FIGS. 11M-11P). However, the phospho-Rb (ser249) was increased in HCT116 and HeLa cells upon treatment with HH32 and HH33 compounds, while the phospho-Rb (ser807/811) was reduced in HCT-116 and increased in HeLa cells (FIGS. 11N-11O). Taken together, HH32 and HH33 upregulated CDK inhibitors, downregulated G2/M progression markers and ultimately arrest the cells at G2/M phase.

Molecular Modeling and Binding Mode Analysis of HH-32 and HH-33 to Cell Cycle Regulators The effects of HH32 and HH33 compounds on cell cycle progression and their ability to inhibit the expression of cell cycle proteins such as cyclins, CDKs and phosphatases encouraged us to perform molecular docking simulations to disclose the most probable binding modes of our compounds within such protein targets, and to provide explanations for their measured inhibitory effects. Overall, results of molecular docking study suggested a proper fit between our compounds (HH32 & HH33) and the active sites of the studied cell cycle proteins (CDK1-cyclin B1, CDK2-cyclin A, CDC25C and Rb) as indicated by their high binding affinity scores (Table 6).

Figure 15A:
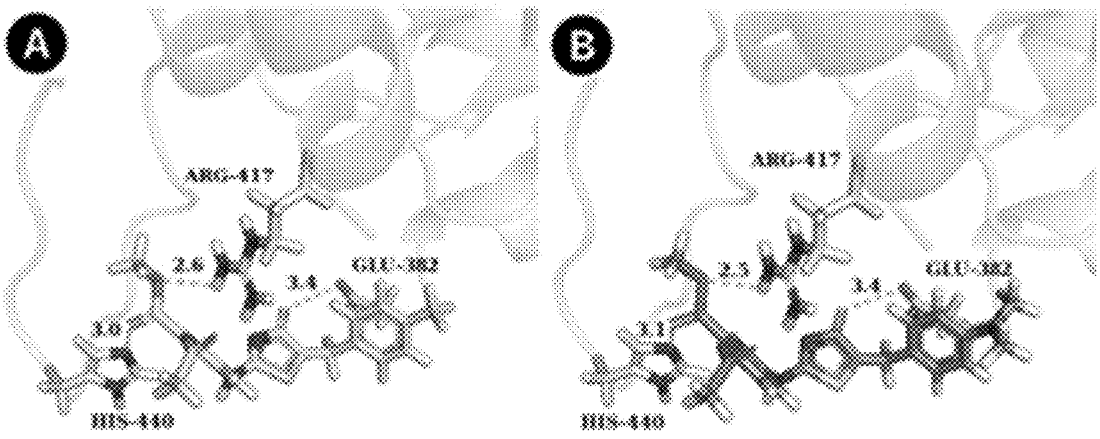
FIGS. 15A-15D provides a binding mode overview of (A) best-docked pose of compound HH32 and (B) best-docked pose of compound HH33 within FIG. 15A the cdc25C active site (PDB-ID: 3OP3), FIG. 15B CDK1 active site (PDB-ID: 4Y72), FIG. 15C CDK2 active site (PDB-ID: 6GUE) and FIG. 15D retinoblastoma tumor suppressor (Rb) protein active site (PDB-ID: 1O9K). Ligands and important amino-acid residues are presented in stick rendering, while hydrogen bond interactions are shown as green dashed lines. Hydrogen bond distances are measured in angstrom (Å).
Figure 15B:
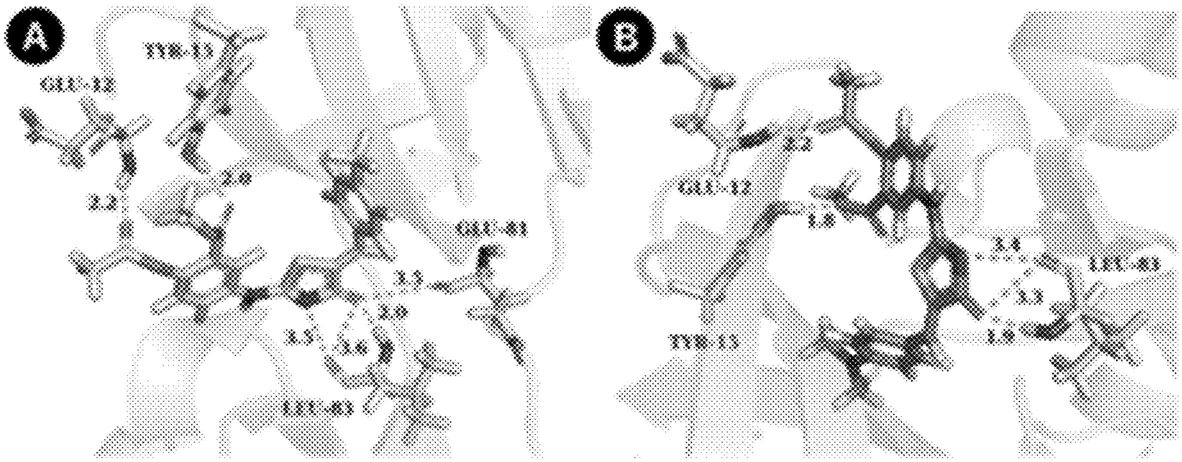

Binding mode analysis of our compounds within the active site of Cdc25C phosphatase showed significant interactions with residues of the c-terminal region containing the $HCX_5R$ motif. Both compounds (HH32 & HH33) shared a common binding pattern (FIG. 15A, Table 7) in which the thiazolinone carbonyl oxygen was able to form hydrogen bond with the residue Glu-382, while the 5-aminosalicylate arm was able to form two H-bond interactions with the respective Arg-417 and His-440 amino acid residues. The present binding mode would enable such compounds to block this small shallow active site and to prevent accessibility to the catalytic cysteine (Cys-377) residue. Furthermore, the binding pattern observed between our compounds and the CDK1-CyclinB complex (maturation promoting factor; MPF) showed high similarity in their interactions with the residues of the active site. The compound HH32 was able to establish two hydrogen bonding through the 5-aminosalicylate arm moieties and the corresponding n-terminal residues; Glu-12 and Tyr-15, while another set of H-bond interactions were observed between its thiazolinone carbonyl oxygen and nitrogen with the corresponding hinge region residues; Glu-81 and Leu-83 (Figure. S6b). On the other hand, compound HH33 showed similar network of interactions except that with the residue Glu-81 (FIG. 15B).

Figure 15C:
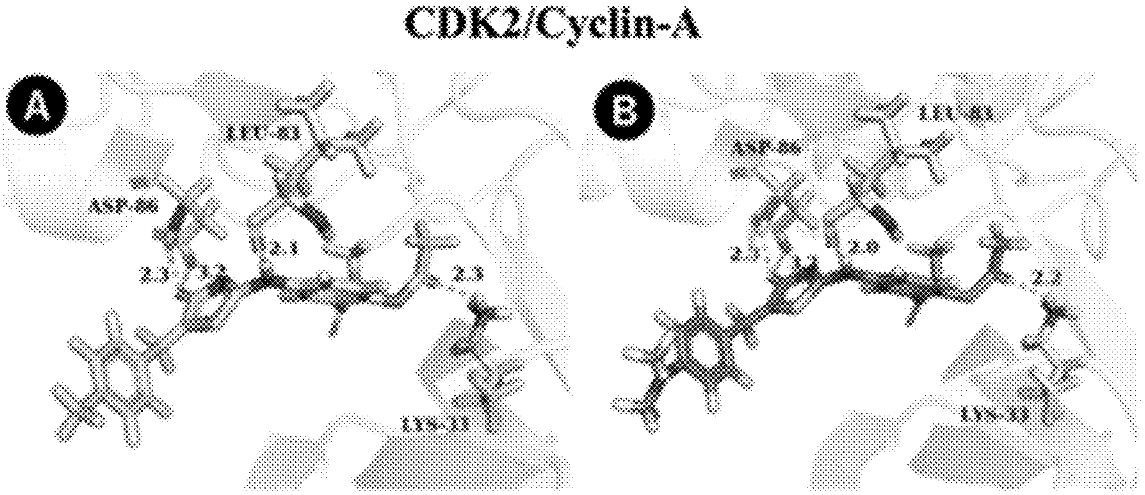

The binding mode secured by our compounds with respect to the CDK2/CyclinA complex suggested a similar binding interactions pattern, in which, the 5-aminosalicylate arm was able to establish H-bond with the n-terminal residue (Lys-33), while the 5-aminosalicylate nitrogen was able to form significant H-bond with the hinge region residue (Leu-83). Finally, the thiazolinone carbonyl oxygen was able to form multiple H-bond interactions with the residue Asp-86 of the solvent exposed region (FIG. 15C).

Figure 15D:
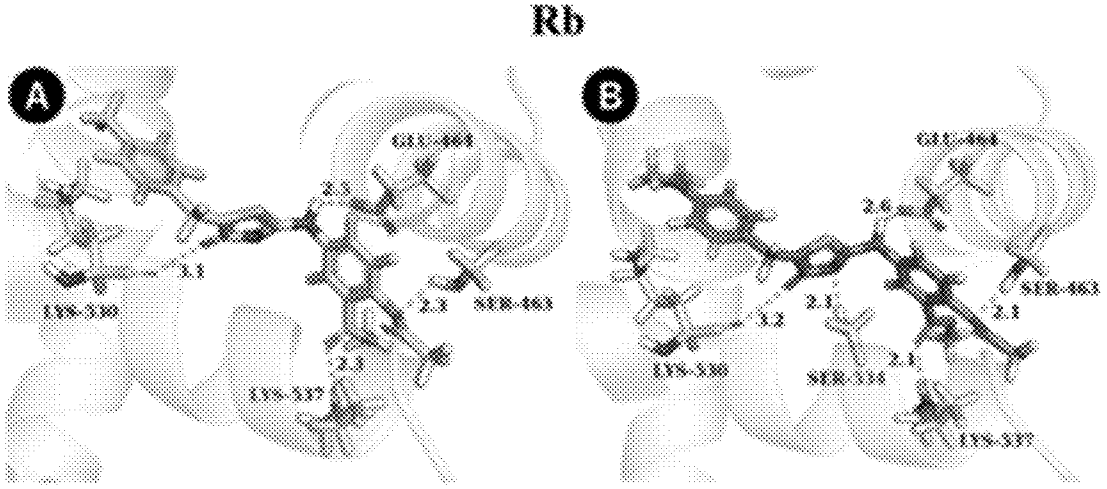

High binding affinities were observed between our compounds and the retinoblastoma tumor suppressor (pRb) protein E2F binding site. The compound HH32 was able to establish four H-bond interactions; one with the residue Lys-530 through its thiazolinone carbonyl oxygen, and another one with the helix α-4 residue Glu-464 through its 5-aminosalicylate nitrogen, while the remaining two were established between the 5-aminosalicylate arm moieties with the corresponding residues; Ser-463 and Lys-537 (FIG. 15D). The compound HH33 showed similar network of interactions with an additional one with the residue Ser-534 (FIG. 15D).

TABLE 6

Summary of the docking parameters utilized against each macromolecule

| Protein Target | PDB-Code | Coordinates Center-X | Center-Y | Center-Z | Grid-Box Size Size-X | Size-Y | Size-Z |
|---|---|---|---|---|---|---|---|
| CDC25c | 3OP3 | −16.878 | 46.646 | −18.098 | 20.0 | 20.0 | 20.0 |
| CDK1-Cyc-B | 4Y72 | 29.215 | −72.059 | 184.798 | 20.0 | 20.0 | 20.0 |
| CDK2-Cyc-A | 6GUE | −6.244 | −22.229 | 22.667 | 20.0 | 20.0 | 20.0 |
| Rb-Supressor | 1O9K | −34.765 | 164.571 | 26.634 | 20.0 | 26.0 | 20.0 |

TABLE 7

Binding affinities of our compounds against the studied molecular targets

| | Docking Score (Kcal/mole) | | | |
|---|---|---|---|---|
| Compound | Cdc25C | CDK1-CyclinB | CDK2-CyclinA | Rb-Supressor |
| HH-32 | −8.10 | −11.50 | −9.80 | −10.10 |
| HH-33 | −8.00 | −11.20 | −9.60 | −9.50 |

HH-32 and HH-33 Triggered Apoptosis Through Intrinsic and Extrinsic Pathways

Figure 16A:
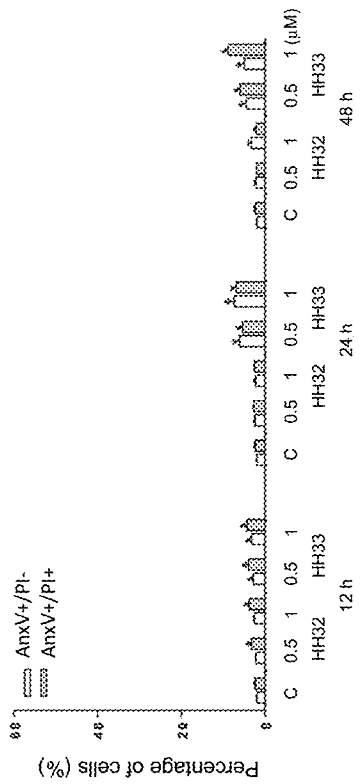
FIGS. 16A-16L shows HH-32 and HH-33 triggered apoptosis through intrinsic and extrinsic pathways.
Figure 16B:
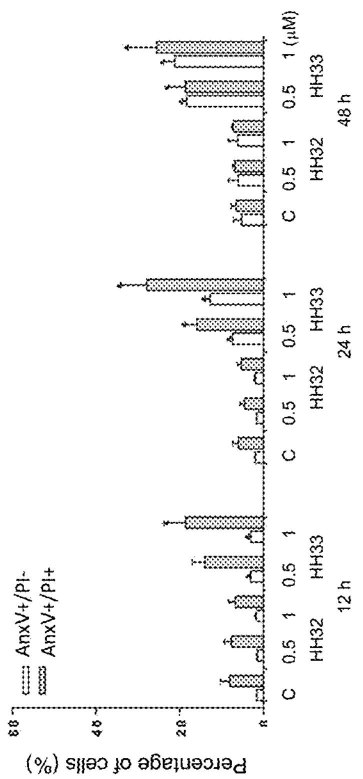
Figure 16C:
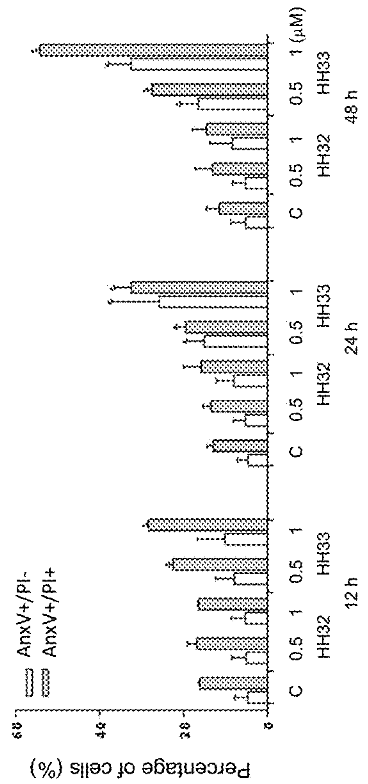
Figure 16D:
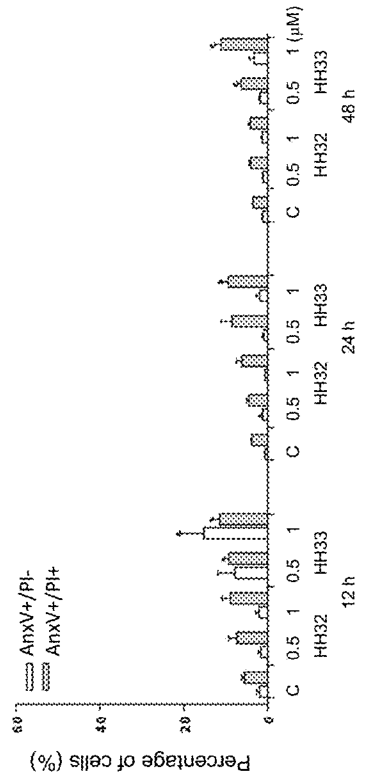
Figure 16E:
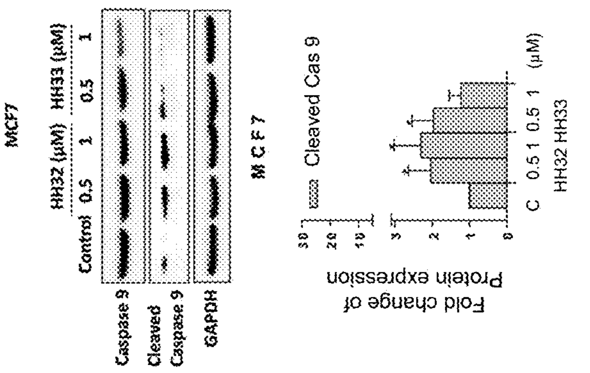
Figure 16F:
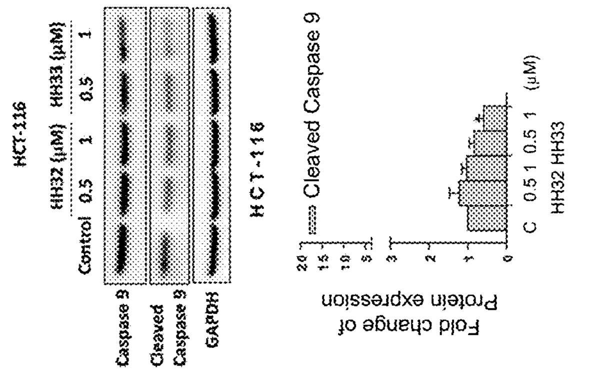
Figure 16G:
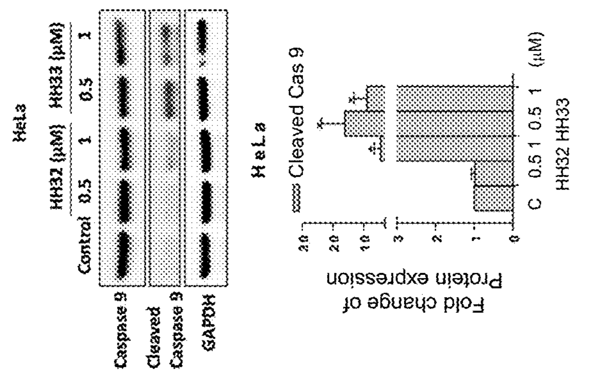
Figure 16H:
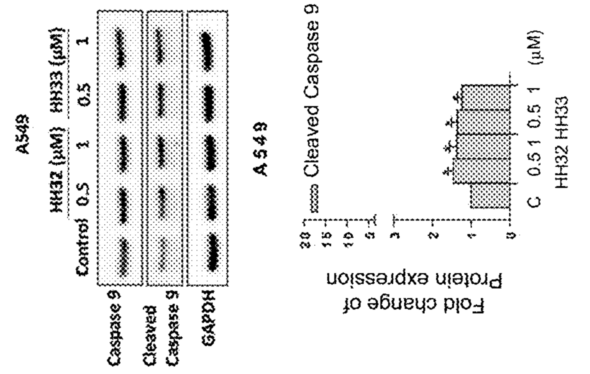
Figure 16I:
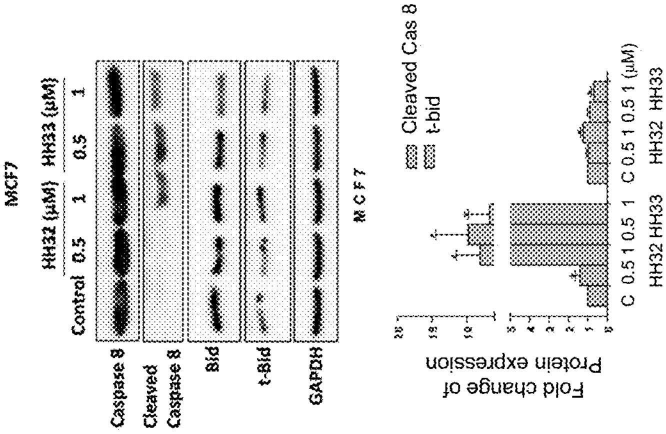
Figure 16J:
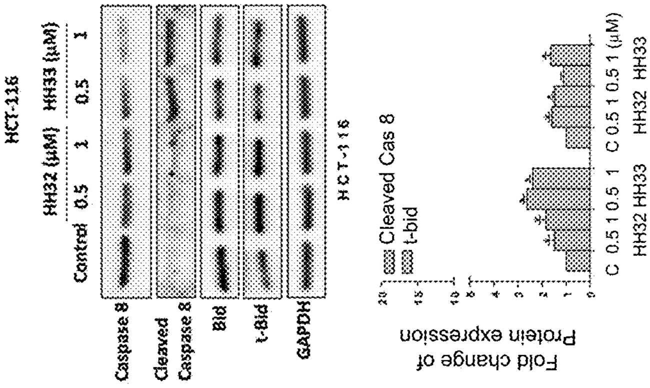
Figure 16K:
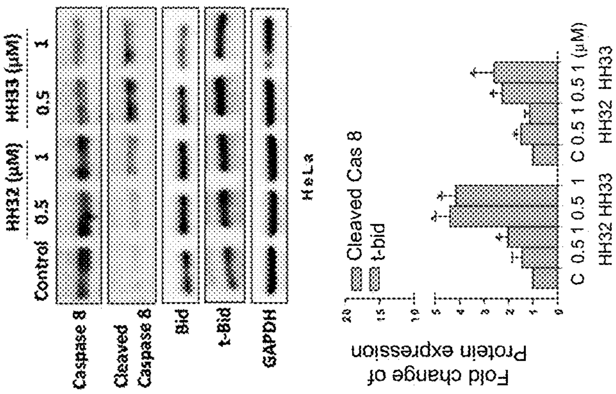
Figure 16L:
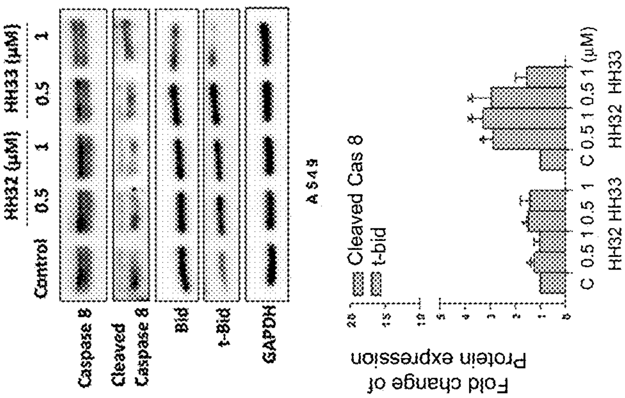
Figure 17A:
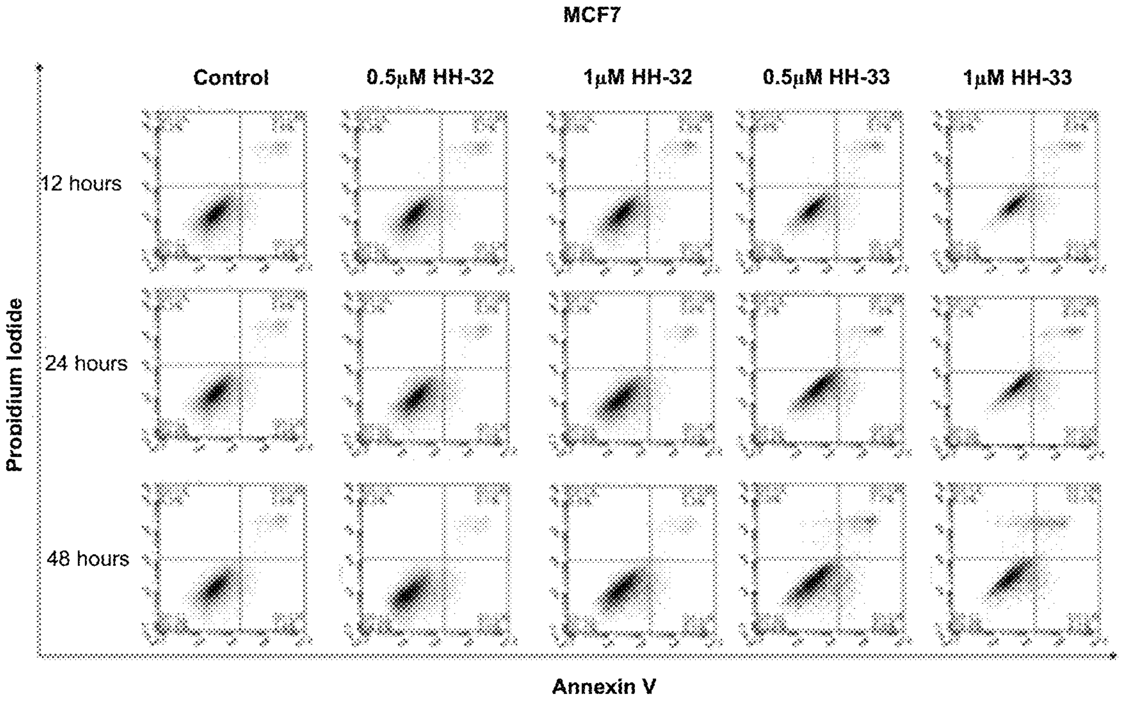
FIGS. 17A-17D provides Annexin-V/PI analysis of apoptosis by flow cytometry. Following treatment with DMSO or 0.5 and 1 μM of HH32 or HH33 for 12,24 and 48 h, FIG. 17A MCF7, FIG. 17B HCT116, FIG. 17C HeLa and FIG. 17D A549 cells were stained with fluorescein-conjugated Annexin V and propidium iodide (PI) and analyzed by flow cytometry. Q4, normal; Q3, annexin V+ (i.e., early apoptotic population); Q1, PI+; Q2, Annexin+/PI+ (i.e., late apoptotic population).
Figure 17B:
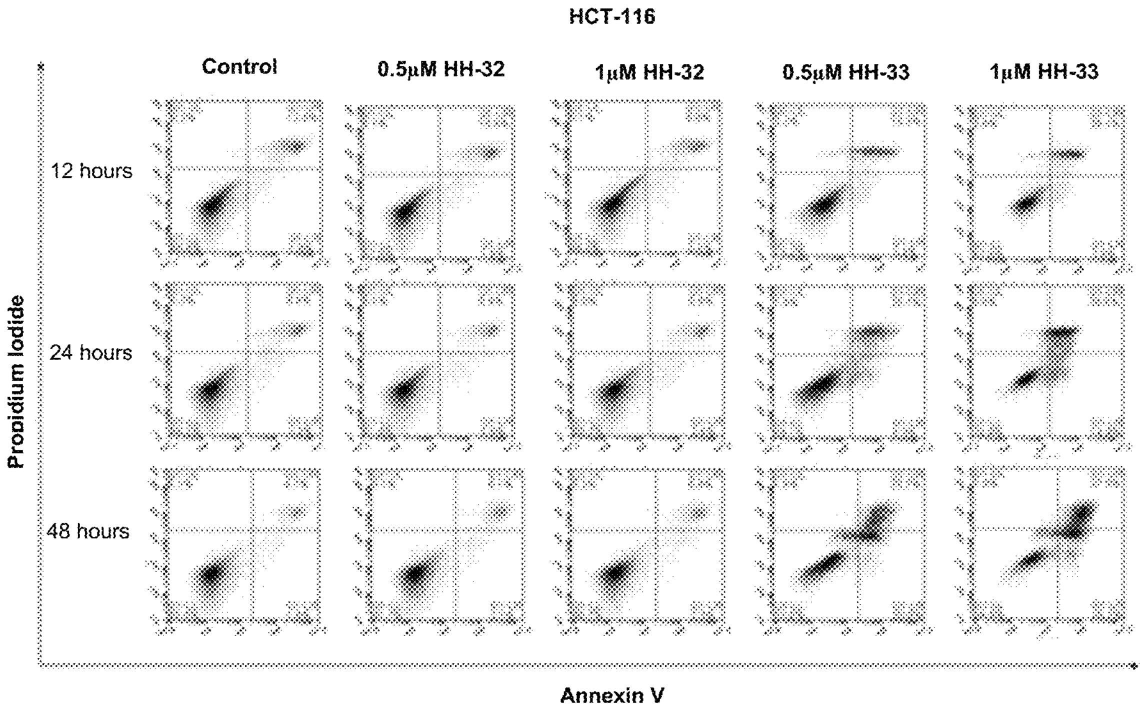
Figure 17C:
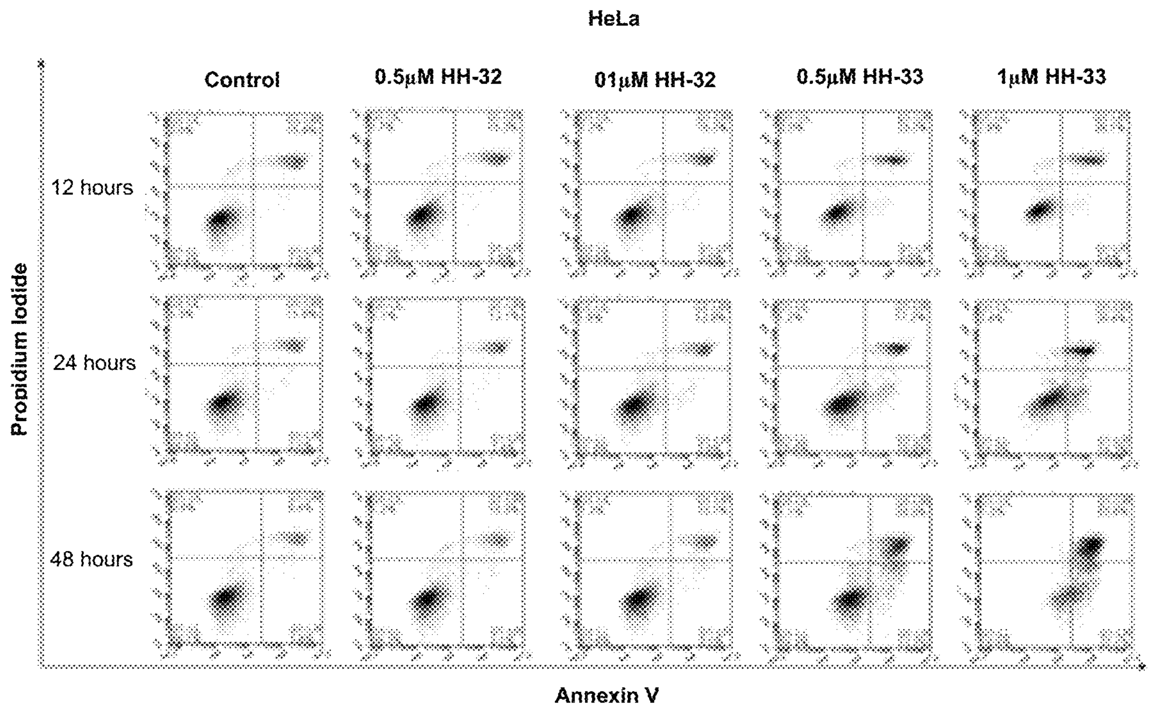
Figure 17D:
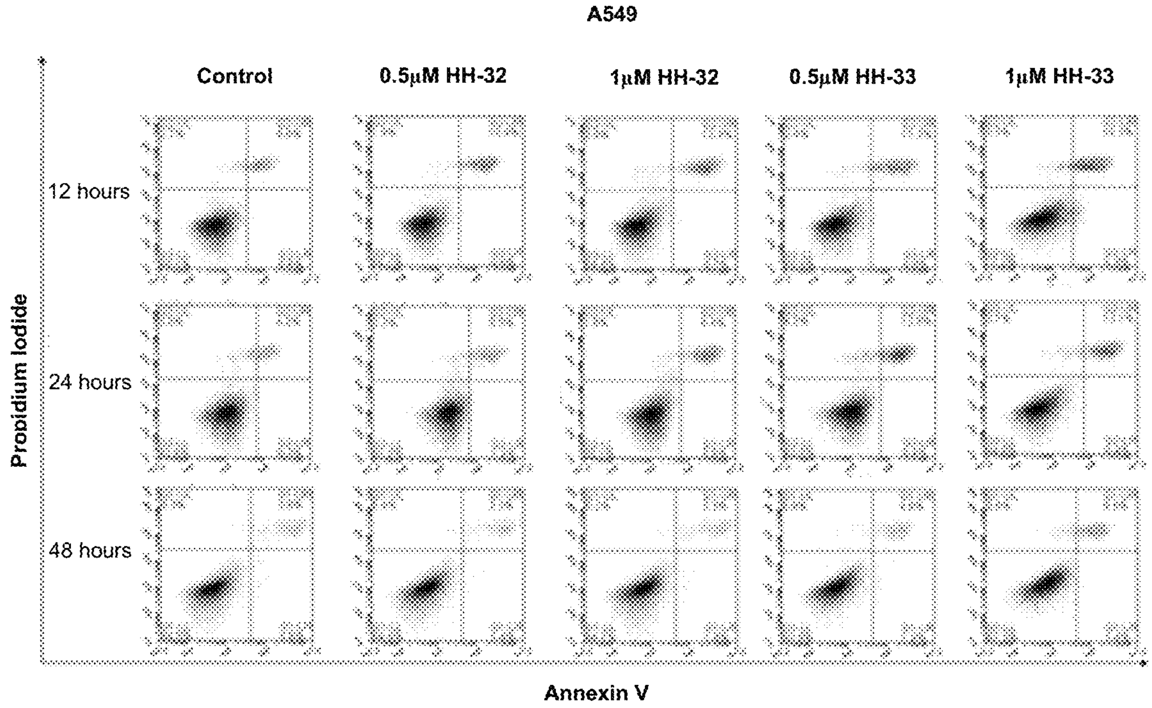

To examine the mechanism of cell death after HH32 and HH33, the detection of apoptotic and necrotic dead cells was performed by Annexin V and Propidium iodide (PI) double staining after 12, 24 and 48 hours treatment with HH32 and HH33 compounds (FIGS. 16A-16D, FIGS. 17A-17D). The early apoptotic cell population (Annexin V+/PI−) of MCF7, HCT-116, HeLa and A549 cells was increased after 24 and 48 hours of HH33 treatment (FIGS. 16A-16D). However, no sign of early apoptosis induction was detected following HH32 treatment in the four cell lines. Notably, the population of late apoptotic/dead cells (Annexin V+/PI+) was increased with increasing the concentration of HH33 in the four cell lines. This indicates that apoptosis is an important cell death mode induced particularly by HH33 in the four cancer cell lines. It is well-known that the activation of apoptosis could be through mitochondria-mediated (intrinsic) or death-receptor (extrinsic) pathways. The activation of intrinsic apoptotic pathway was first tested and found to be induced by HH33 compound which was indicated by the increase in the cleavage of caspase-9 in MCF7, HeLa and A549 cells (FIGS. 16E-16H). Although the population of late apoptotic/dead cells (Annexin V+/PI+) was elevated by HH32 and HH33 in HCT-116 cells (FIG. 16B), however, caspase-9 activation in HCT-116 cells was not induced by both compounds (FIG. 16G). This suggests that extrinsic pathway could also contribute to HH32 and HH33-induced apoptosis which was examined by measuring the cleavage level of caspase-8 (FIGS. 16I-16L). In this regard, western blot analysis showed that caspase-8 was cleaved by HH32 and HH33 in all cell lines and it was higher in cells treated with HH33. In addition, the cleavage of the downstream protein Bid was induced also by both compounds in HCT-116, HeLa and A549 cells (FIGS. 16J-16L). These results demonstrate that the observed death induced by HH32 and HH33 is through a caspase-dependent apoptotic pathway, which might involve both intrinsic and extrinsic pathways.

HH32 and HH33 Treatment Influenced the Level of c-MYC Protein

Figure 18:
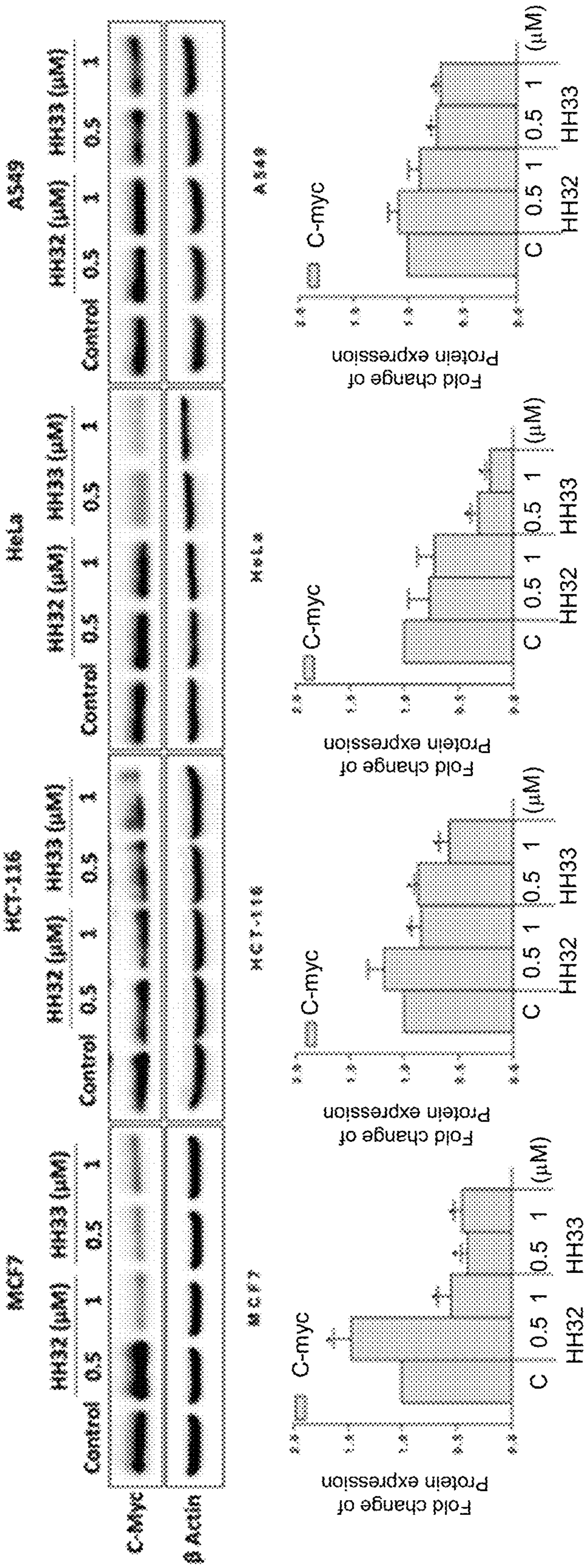
FIG. 18 shows the anticancer activity of HH32 and HH33 by measuring the expression of the oncogene c-Myc in MCF7, HCT-116, HeLa and A549 cell lines. Western blot analysis showing the effect of HH32 and HH33 treatment at 0.5 and 1 μM concentrations on total c-Myc protein level.

The anticancer activity of HH32 and HH33 was further investigated by measuring the expression of the oncogene c-Myc in the four cancer cell lines. Myc is a proto-oncogene and acting as a transcription factor that binds DNA and activates the transcription of growth-related genes [46]. Therefore, western blot analysis was done for the effect of HH32 and HH33 treatment on total c-Myc protein level (FIG. 18). HH32-mediated downregulation of c-Myc was observed at 1 μM concentration in MCF7 and HCT-116 cells. While HH33 treatment decreased c-Myc protein level in the four cancer cell lines at 0.5 and 1 μM concentrations (FIG. 18). These results indicate the downregulation of c-Myc protein by HH32 and HH33 in cancer cell lines.

Metabolomic Profile of HH32- and HH33-Treated Cells

Figure 20:
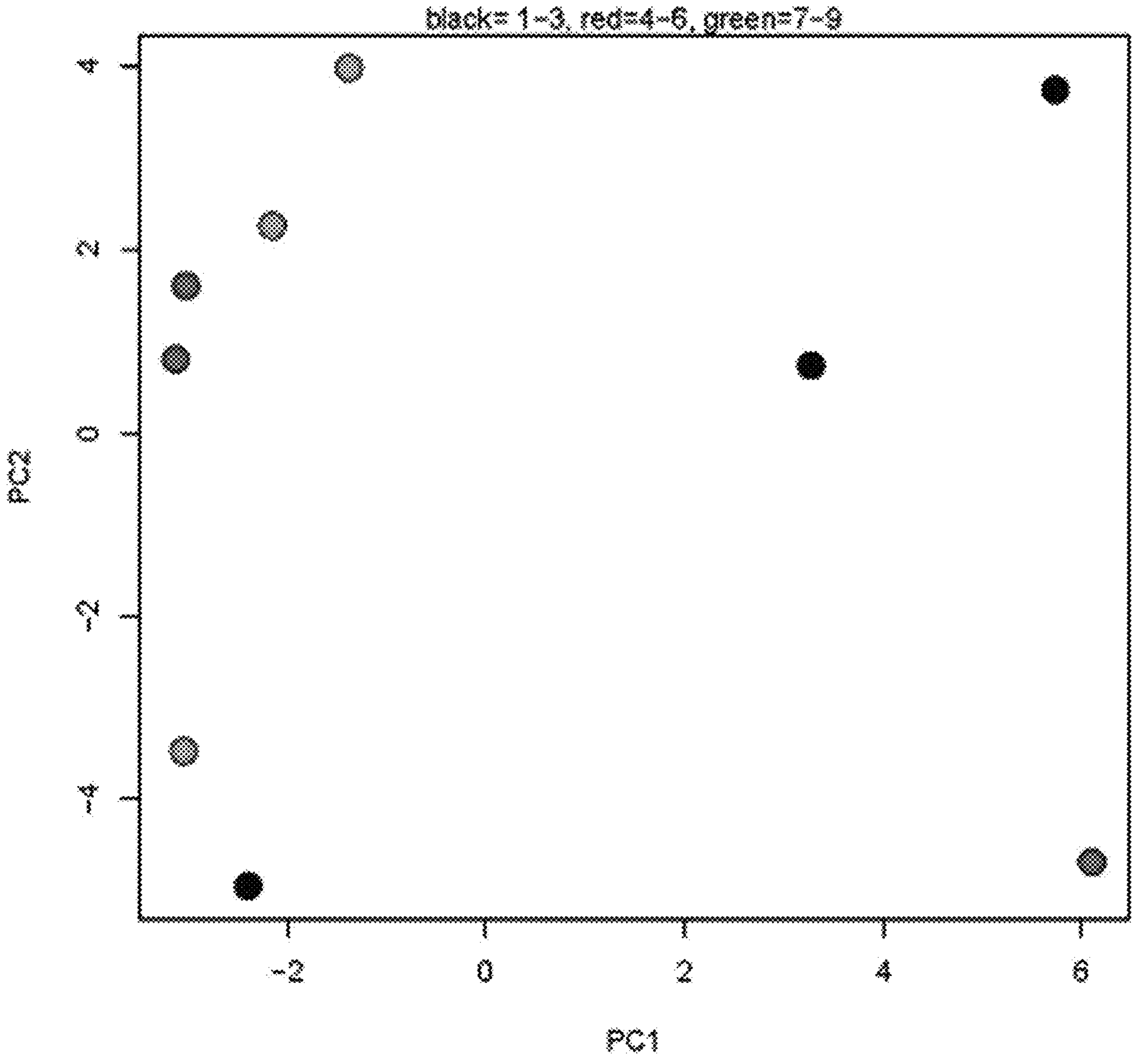
FIG. 20 provides the Principle Component Analysis of the metabolic profile of MCF7 cancer cells in triplicates after treatment with DMSO control (black dots), 1 μM HH32 (medium grey dots), and 1 μM HH33 (light grey dots).

Recent discoveries in the field of cancer cells metabolism are supporting the direction of considering cancer as a metabolic disease [47, 48]. This opened the door for new cancer therapeutics that selectively targeting metabolic pathways altered during tumorigenesis. Accordingly, we tested the effects of the two compounds on the metabolomics of the MCF7 cells. Using Human Metabolome Database (HMDB 4.0), a total of 53 metabolites was detected in MCF7 samples (FIG. 19). Next, we investigated the effect of the drug treatment on each single metabolite using a student t-test and the analysis revealed that Guanosine levels were altered after treatment with HH32. In addition, a significant decreased in the levels of Decanoic Acid, Adenosine and 1-Monopalmitin was observed in cells treated with HH33 as compared to untreated cells Interestingly, the analysis of 1-Monopalmitin level showed a 4.5-fold reduction in cells treated with HH33 compared to control cells. Metabolomic data were visualized utilizing Principal component analysis (FIG. 20).

DISCUSSION

Rapid, uncontrolled cell division is the hallmark of cancer cells that is responsible for most deleterious consequences associated with cancer. Selective reduction or inhibition of cancer cell proliferation is an important target of cancer therapeutics. One of the striking effects of our aminosalicylate-thiazolinone-based compounds, particularly the HH33, is the arrest of a very high percentage of cancer cells (up to 90%) at the G2/M border. Without being bound to any particular theory, the present invention proposes that this effect may be due to the induction of DNA damage by HH33, which modulates the expression or the activity of cell cycle regulatory proteins such as the p53, p21, cyclins, CDKs and phosphatases. A marked increase in the tail moments in the comet assay and in the level of γ-H2AX, markers of DNA damage, confirmed the induction of DNA damage by both compounds. Surprisingly, none of the two compounds induced G1/S nor intra S-phase arrest in any of the tested cell lines neither at short nor at long incubation periods. We speculate that the compounds induce replication-dependent DNA damage which activates the G2/M, but not the G1/S checkpoint [49]. Regulation of these cell cycle checkpoints (G1/S, intra-S and G2/M) is achieved by different families of proteins including the cyclins, the CDKs and the CDK inhibitors [50]. Activation of the G2/M checkpoint subsequent to DNA damage induction is mainly initiated through activating the p53 protein which in turn activates its down-stream protein p21 [51]. Active p21, by phosphorylation, inhibits the cyclin B/CDK1 complex and prevents cells from crossing the G2 border into the mitotic phase [52]. In line with the high percent of cells arrested at the G2 phase after treatment with HH32 and HH33 compounds, the levels of p53 and p21 were significantly increased, while the level of cyclin B1 and CDK1 was reduced in two out of the four tested cell lines (MCF7, and A549). The reduction of p53 and p21 levels and the increased level of cyclin B1 in HeLa cells under the same treatment conditions may be attributed to the abnormal status of p53 in these cells. Over 90% of cervical cancers and cancer-derived cell lines including HeLa contain inactivated p53, where the p53 tumor suppressor pathway is disrupted by human papillomavirus (HPV) [53]. Activation of the G2/M checkpoint after induction of DNA damage aims at preventing the cells from entry into mitosis with damaged DNA [54]. This delay in cell cycle progression allows the cellular DNA repair machinery to repair the damaged DNA before progression to the mitosis which is the most critical phase of the cell cycle. If cells are defective in repairing the DNA damage or the damage is beyond the ability of the cells to repair, cell death pathways such as apoptosis are activated [55]. The G2 arrest induced by the two compounds and particularly by the HH33 was sustainable in MCF7 and A549 cells during the whole investigation period (up to 72 h), while this G2 arrest reached peak at 24 h in the other two cell lines (HCT 116 and HeLa) and was greatly reduced at 48 and 72 h with the appearance of sub-G1 cells indicative of apoptosis. This indicates that the amount of DNA damage induced by the compounds at these concentrations was beyond the ability of the four cell lines to repair, but due to the different genetic backgrounds, two cell lines (MCF7 and A549) were not able to execute apoptosis and hence they were arrested in G2 phase for up to 72 h. On the other hand, the other two cell lines (HCT 116 and HeLa) underwent apoptosis after failure to repair the compounds-induced DNA damage, which may explain the high sensitivity of these two cell lines to the tested compounds.

Activation of the G2/M checkpoint after induction of DNA damage aims at preventing the cells from entry into mitosis with damaged DNA [54]. This delay in cell cycle progression allows the cellular DNA repair machinery to repair the damaged DNA before progression to the mitosis which is the most critical phase of the cell cycle. If cells are defective in repairing the DNA damage or the damage is beyond the ability of the cells to repair, cell death pathways such as apoptosis are activated [51]. The G2 arrest induced by the two compounds and particularly by the HH33 was sustainable in MCF7 and A549 cells during the whole investigation period (up to 72 h), while this G2 arrest reached peak at 24 h in the other two cell lines (HCT116 and HeLa) and was greatly reduced at 48 and 72 h with the appearance of sub-G1 cells indicative of apoptosis. This indicates that the amount of DNA damage induced by the compounds at these concentrations was beyond the ability of the four cell lines to repair, but due to the different genetic backgrounds, two cell lines (MCF7 and A549) were not able to execute apoptosis and hence they were arrested in G2 phase for up to 72 h. On the other hand, the other two cell lines (HCT116 and HeLa) underwent apoptosis after failure to repair the compounds-induced DNA damage, which may explain the high sensitivity of these two cell lines to the tested compounds.

Retinoblastoma (Rb) protein is one of the important player that has been previously reported to regulate progression of cell cycle [56]. Phosphorylation of Rb at different sites by CDKs results in its inactivation and the release of E2F transcription factor, which in turns activates the transcription of genes required for progression of the cell cycle such as the cyclins [57]. During the normal cell cycle progression, Rb remains phosphorylated, which allows cell progression through G1, S, G2 and M phases. We used two phospho-Rb antibodies (ser-249 and ser807/811) to investigate the effects of our two compounds on the phosphorylation of Rb. The two compounds induced reduction in Rb phosphorylation in MCF7 and A549 cells which is in line with the persistent G2/M arrest in these two cell lines. The phospho-Rb (ser249) was increased in HCT 116 and HeLa cells upon treatment with HH32 and HH33 compounds, while the phospho-Rb (ser807/811) was reduced in HCT116 and increased in HeLa cells. This also explains the reduction in G2/M arrest in these two cell lines after 24 h of treatment with HH32 and HH33. The increased phosphorylation of Rb in these two cell lines lead to the release of E2F transcription factor which activates the expression of genes such as cyclins and CDKs leading to abrogation of the G2/M arrest and progression of cells into mitosis. Because these cells enter mitosis with damaged DNA, they undergo apoptosis which was indicated by the increased fraction of sub-G1 population. In support of this result, higher fractions of cells in early and late apoptosis were observed in HCT116 and HeLa cells compared to MCF7 and A549 cells after treatment with HH32 and HH33 followed by staining with annexin V/propidium iodide. These results indicate that our compounds are more potent against cells capable of executing apoptosis. In addition to the indirect induction of G2/M arrest due to DNA damage, we do not exclude the possibility of direct inhibitory effects of our compounds on drivers of the cell cycle progression. This possibility is supported by the results of the molecular modelling which suggest a proper fit between our compounds and CDK1-cyclin B1, CDK2-cyclin A, CDC25C and Rb.

Predicting the mode of action of the new compounds was derived by the results of the transcriptomic analysis. In addition to the differentially expressed pathways, we identified six genes that were shared among the most downregulated pathways in the MCF7 and A549 cells (Table 5). Three (ATAD2, CDCA3 and FAMIIIB) out of these 6 genes are directly involved in cell division and progression of cell cycle. (1) ATAD2 is a member of the AAA domain-containing protein 2 family of ATPase. It's a transcriptional coactivator of the nuclear receptor ESR1 that is needed to express a subset of estradiol target genes including CCND1, MYC, and E2F. ATAD2 may be involved in the recruitment or occupancy of CREBBP at the promoters of several ESR1 target genes. This protein is likely to be required for histone hyperacetylation. It is involved in the estrogen-induced cell proliferation and cell cycle progression of breast cancer cells [58]. (2) CDCA3, or cell division cycle-associated protein-3, is an F-box-like protein that is involved in driving the entry of the cell into mitosis. CDCA3 mediates the ubiquitination and degradation of WEE1 kinase at G2/M phase [59]. (3) FAMIIIB induces apoptosis of alpha and beta cells in a dose- and time-dependent manner. Interestingly, FAMIIIB was identified as one of novel markers for detecting microsatellite instability in cancer and determining synthetic lethality with inhibition of the DNA excision repair pathway [60].

Upregulated machinery of lipid metabolism has been observed in cancer cells to allow formation of cell membrane required for the rapidly dividing cells, whereas mitotically arrested and apoptotic cells were shown to have high accumulation of lipid droplets following treatment with chemotherapeutic drugs [63]. This may help the cancer cells to overcome the effects of anti-cancer agents and may contribute to the development of resistance. Interestingly, increased lipid droplet number is a feature of aggressive breast cancer [61]. However, targeting fatty acid (FA) metabolism was not generally identified as a potential therapeutic approach in cancer, due to the high plasticity of the FA metabolic pathways, yet it remains an additional desirable effect of anticancer therapy [62]. Therefore, the present study involved analyzing the release of different metabolites following HH32 and HH33 treatment. We report here a 4.5-fold reduction in the level of 1-monopalmitine in HH33-treated MCF7 cells compared to control cells. 1-monopalmitin, which is a monoacylglycerol (MAG), is formed via the release of fatty acid from diacyglecerol (DAG) by DAG lipase. This may indicate the reduced hydrolysis of DAG (may be due to inhibition of DAG lipase by HH33; or due to inhibition of; Fatty acid synthase (FASN), the rate-limiting enzyme in FA synthesis, or stearoyl-CoA desaturase (SCD); the unsaturation enzyme that convers palmitate into mono-palmitin), with subsequent deprivation of the MCF7 cells of an important source of energy, which contribute to the anti-proliferative activity of HH33.

Noteworthy, especially under metabolic stress, cancer cells acquire various mechanisms to enhance exogenous FA-uptake, a fact that minimizes the importance of FASN as an anti-cancer target [63, 64]. In our metabolomic study, palmitic acid was significantly increased at 20% in HH33-treated MCF7 cells, denoting that the FASN was not suppressed. Moreover, the HH33-induced reduction in the level of decanoic acid in MCF7 cells may also indicate a lipolytic-inhibitory effect of HH33, which deprives the cancer cells of an important source of energy and structural fats needed for their proliferation. An earlier study have proposed a role for decanoic acid in stimulating de novo lipogenesis in cancer cell (e.g. U87MG cells) by a PPARγ-mediated mechanism [65]. Pharmacological inhibition of fatty acid synthesis is reported to be selectively cytotoxic to cancer cells in vivo and in vitro [66]. Moreover, a significant reduction of adenosine, an endogenous substance, in HH33-treated MCF7 cells was observed in metabolic analysis. For instance, adenosine is involved in many cellular processes including neurotransmission, regulation of cellular growth, metabolism and immune checkpoint [67, 68]. Accumulation of adenosine has been reported recently to be associated with tumour progression and ability of cancer cells to escape from the host immune [69]. These results indicate the ability of HH33 to reduce synthesis of adenosine or to enhance its degradation, which shed light on other effects of our derivatives that may support their use in combination with immunotherapy.

In summary, we described here two new 5-aminosalicylate-4-thiazolinone derivatives with comparable anti-proliferative activity and better selectivity than the anti-cancer drug doxorubicin. Without being bound to any particular theory, the present invention proposes that they work by inducing DNA damage, modulating the function of cell cycle regulators, inducing G2/M cell cycle arrest and apoptosis and modulating the metabolic profile of cancer cells. The pleiotropic biological effect of HH32 and HH33 compounds on cancer cells suggests the importance of assessing their anti-cancer activities in preclinical models, to explore a new promising area of potential drug development.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

REFERENCES

[1] Global Burden of Disease Cancer Collaboration, Fitzmaurice C, Abate D, et al. Global, Regional, and National Cancer Incidence, Mortality, Years of Life Lost, Years Lived With Disability, and Disability-Adjusted Life-Years for 29 Cancer Groups, 1990 to 2017: A Systematic Analysis for the Global Burden of Disease Study [published correction appears in *JAMA* Oncol. 2020 Mar. 1; 6(3):444] [published correction appears in *JAMA* Oncol. 2020 May 1;6(5):789] [published correction appears in *JAMA* Oncol. 2021 Mar. 1; 7(3):466]. *JAMA Oncol.* 2019; 5(12):1749-1768. doi:10.1001/jamaoncol.2019.2996.

[2] Tripathi, A. C., et al., 4-*Thiazolidinones: the advances continue* . . . . Eur J Med Chem, 2014. 72: p. 52-77.

[3] Senkiv, J., et al., 5-*Ene*-4-*thiazolidinones induce apoptosis in mammalian leukemia cells.* Eur J Med Chem, 2016. 117: p. 33-46.

[4] Choudhury C. and Bhardwaj A. Hybrid Dynamic Pharmacophore Models as Effective Tools to Identify Novel Chemotypes for Anti-TB Inhibitor Design: A Case Study With Mtb-DapB. Frontiers in Chemistry 2020(8) 596412.

[5] Lin X, Li X and Lin X. A Review on Applications of Computational Methods in Drug Screening and Design. Molecules 2020, 25, 1375; doi:10.3390/molecules25061375.

[6] S Ramadan, W., et al., *Induction of DNA damage, apoptosis and cell cycle perturbation mediate cytotoxic activity of new* 5-*aminosalicylate*-4-*thiazolinone hybrid derivatives.* Biomedicine & Pharmacotherapy, 2020. 131: p. 110571.

[7] Abdu-Allah, H. H., et al., *Design and synthesis of novel* 5-*aminosalicylate* (5-*ASA*)-4-*thiazolinone hybrid derivatives with promising antiprohferative activity.* Bioorg Med Chem Lett, 2016. 26(7): p. 1647-50.

[8] Vazhappilly, C. G., et al., *Inhibition of SHP*2 *by new compounds induces differential effects on RAS/RAF/ERK and PI*3*K/AKT pathways in different cancer cell types.* Invest New Drugs, 2019. 37(2): p. 252-261.

[9] Abdu-Allah, H. H. M., et al., *Conjugation of* 4-*aminosalicylate with thiazolinones afforded non-cytotoxic potent in vitro and in vivo anti-inflammatory hybrids.* Bioorganic Chemistry, 2020. 94: p. 103378.

[10] Mahdi, J. G., *Medicinal potential of willow: A chemical perspective of aspirin discovery.* Journal of Saudi Chemical Society, 2010. 14(3): p. 317-322.

[11] Hannah, J., et al., *Novel analgesic-antiinflammatory salicylates.* J Med Chem, 1978. 21(11): p. 1093-100.

[12] Collier, H. O. J., *A Pharmacological Analysis of Aspirin, in Advances in Pharmacology*, S. Garattini, et al., Editors. 1970, Academic Press. p. 333-405.

[13] Rainsford, K. D., A. Schweitzer, and K. Brune, *Distribution of the acetyl compared with the salicyl moiety of acetylsalicylic acid. Acetylation of macromolecules in organs wherein side-effects are manifest.* Biochem Pharmacol, 1983. 32(7): p. 1301-8.

[14] Pinckard, R. N., D. Hawkins, and R. S. Farr, *In vitro Acetylation of Plasma Proteins, Enzymes and DNA by Aspirin.* Nature, 1968. 219(5149): p. 68-69.

[15] Lai, T. S., C. Davies, and C. S. Greenberg, *Human tissue transglutaminase is inhibited by pharmacologic and chemical acetylation.* Protein Sci, 2010. 19(2): p. 229-35.

[16] Alfonso, L. F., et al., *Aspirin inhibits camptothecin-induced p*21*CIP*1 *levels and potentiates apoptosis in human breast cancer cells.* Int J Oncol, 2009. 34(3): p. 597-608.

[17] Ai, G., et al., *Aspirin acetylates wild type and mutant p*53 *in colon cancer cells: identification of aspirin acetylated sites on recombinant* p53. Tumour Biol, 2016. 37(5): p. 6007-16.

[18] Chen, Z., et al., *Aspirin cooperates with p*300 *to activate the acetylation of H*3*K*9 *and promote FasL-mediated apoptosis of cancer stem-like cells in colorectal cancer.* Theranostics, 2018. 8(16): p. 4447-4461.

[19] Ai, G., et al., *Aspirin inhibits glucose-6-phosphate dehydrogenase activity in HCT 116 cells through acetylation: Identification of aspirin-acetylated sites*. Mol Med Rep, 2016. 14(2): p. 1726-32.

[20] Comer, S. D., et al., *Abuse liability of prescription opioids compared to heroin in morphine-maintained heroin abusers*. Neuropsychopharmacology, 2008. 33(5): p. 1179-91.

[21] Sassi, N., et al., *Mitochondria-targeted resveratrol derivatives act as cytotoxic pro-oxidants*. Curr Pharm Des, 2014. 20(2): p. 172-9.

[22] http://www.cambridgesoft.com. USA.

[23] MOPAC2012, J. J. P. S., *Stewart Computational Chemistry*, Colorado Springs. CO, USA, 2012.

[24] Pedretti, A., L. Villa, and G. Vistoli, *VEGA—an open platform to develop chemo-bio-informatics applications, using plug-in architecture and script programming*. J Comput Aided Mol Des, 2004. 18(3): p. 167-73.

[25] Pedretti, A., L. Villa, and G. Vistoli, *Atom-type description language: a universal language to recognize atom types implemented in the VEGA program*. Theoretical Chemistry Accounts, 2003. 109(4): p. 229-232.

[26] Yap, C. W., *PaDEL-descriptor: An open source software to calculate molecular descriptors and fingerprints*. Journal of Computational Chemistry, 2011. 32(7): p. 1466-1474.

[27] Gramatica, P., et al., *QSARINS: A new software for the development, analysis, and validation of QSAR MLR models*. Journal of Computational Chemistry, 2013. 34(24): p. 2121-2132.

[28] Gramatica, P., S. Cassani, and N. Chirico, *QSARINS-chem: Insubria datasets and new QSAR/QSPR models for environmental pollutants in QSARINS*. Journal of Computational Chemistry, 2014. 35(13): p. 1036-1044.

[29] El-Awady, R. A., et al., *Interaction of celecoxib with different anti-cancer drugs is antagonistic in breast but not in other cancer cells*. Toxicol Appl Pharmacol, 2011. 255(3): p. 271-86.

[30] Ning, Z., A. J. Cox, and J. C. Mullikin, *SSAHA: a fast search method for large DNA databases*. Genome Res, 2001. 11(10): p. 1725-9.

[31] Li, H., *Exploring single-sample SNP and INDEL calling with whole-genome de novo assembly*. Bioinformatics, 2012. 28(14): p. 1838-44.

[32] Smith, T. F. and M. S. Waterman, *Identification of common molecular subsequences*. J Mol Biol, 1981. 147(1): p. 195-7.

[33] Ramadan, W. S., et al., *Interplay between Epigenetics, Expression of Estrogen Receptor—alpha, HER2/ERBB2 and Sensitivity of Triple Negative Breast Cancer Cells to Hormonal Therapy*. Cancers (Basel), 2018. 11(1).

[34] El-Awady, R. A., et al., *Modulation of DNA damage response and induction of apoptosis mediates synergism between doxorubicin and a new imidazopyridine derivative in breast and lung cancer cells*. DNA Repair, 2016. 37: p. 1-11.

[35] Trott, O. and A. J. Olson, *AutoDock Vina: improving the speed and accuracy of docking with a new scoring function, efficient optimization, and multithreading*. Journal of computational chemistry, 2010. 31(2): p. 455-461.

[36] Semreen, M. H., et al., *Comparative metabolomics of MCF-7 breast cancer cells using different extraction solvents assessed by mass spectroscopy*. Scientific Reports, 2019. 9(1): p. 13126.

[37] Wishart, D. S., et al., *HMDB 4.0: the human metabolome database for 2018*. Nucleic Acids Res, 2018. 46(D1): p. D608-d617.

[38] Alexandrov, L. B., et al., *Deciphering signatures of mutational processes operative in human cancer*. Cell Rep, 2013. 3(1): p. 246-59.

[39] Dieterle, F., et al., *Probabilistic quotient normalization as robust method to account for dilution of complex biological mixtures. Application in 1H NMR metabonomics*. Anal Chem, 2006. 78(13): p. 4281-90.

[40] Benjamini, Y., et al., *Controlling the false discovery rate in behavior genetics research*. Behav Brain Res, 2001. 125(1-2): p. 279-84.

[41 Storey, J. D., *A direct approach to false discovery rates*. Journal of the Royal Statistical Society: Series B (Statistical Methodology), 2002. 64(3): p. 479-498.

[42] Kuete, V., et al., *Cytotoxicity of Plumbagin, Rapanone and 12 other naturally occurring Quinones from Kenyan Flora towards human carcinoma cells*. BMC Pharmacology and Toxicology, 2016. 17(1): p. 60.

[43] Neizer-Ashun, F. and R. Bhattacharya, *Reality CHEK: Understanding the biology and clinical potential of CHK1*. Cancer Letters, 2021. 497: p. 202-211.

[44] Chohan, T. A., et al., *An insight into the emerging role of cyclin-dependent kinase inhibitors as potential therapeutic agents for the treatment of advanced cancers*. Biomedicine & Pharmacotherapy, 2018. 107: p. 1326-1341.

[45] Gabay, M., Y. Li, and D. W. Felsher, *MYC activation is a hallmark of cancer initiation and maintenance*. Cold Spring Harb Perspect Med, 2014. 4(6).

[46] Martinez-Outschoorn, U. E., et al., *Cancer metabolism: a therapeutic perspective*. Nat Rev Clin Oncol, 2017. 14(1): p. 11-31.

[47] Seyfried, T. N., et al., *Cancer as a metabolic disease: implications for novel therapeutics*. Carcinogenesis, 2014. 35(3): p. 515-527.

[48] Nair, A. B., Jacob S. (2016). A simple practical guide for dose conversion between animal and human. J Basic Clin Pharma 2016, 7:27-31.

[49] Willis, N. and N. Rhind, *Regulation of DNA replication by the S-phase DNA damage checkpoint*. Cell division, 2009. 4: p. 13-13.

[50] Barnum, K. J. and M. J. O'Connell, *Cell cycle regulation by checkpoints*. Methods in molecular biology (Clifton, N.J.), 2014. 1170: p. 29-40.

[51] Taylor, W. R. and G. R. Stark, *Regulation of the G2/M transition by p53*. Oncogene, 2001. 20(15): p. 1803-15.

[52] Dash, B. C. and W. S. El-Deiry, *Phosphorylation of p21 in G2/M promotes cyclin B-Cdc2 kinase activity*. Mol Cell Biol, 2005. 25(8): p. 3364-87.

[53] Hietanen, S., et al., *Activation of p53 in cervical carcinoma cells by small molecules*. Proc Natl Acad Sci USA, 2000. 97(15): p. 8501-6.

[54] Gatei, M., et al., *Ataxia-telangiectasia-mutated (ATM) and NBS1-dependent phosphorylation of Chk1 on Ser-317 in response to ionizing radiation*. J Biol Chem, 2003. 278(17): p. 14806-11.

[55] Norbury, C. J. and B. Zhivotovsky, *DNA damage-induced apoptosis*. Oncogene, 2004. 23(16): p. 2797-2808.

[56] Henley, S. A. and F. A. Dick, *The retinoblastoma family of proteins and their regulatory functions in the mammalian cell division cycle*. Cell division, 2012. 7(1): p. 10-10.

[57] Giacinti, C. and A. Giordano, *RB and cell cycle progression*. Oncogene, 2006. 25(38): p. 5220-7.

[58] Hussain, M., et al., *ATAD2 in cancer: a pharmacologically challenging but tractable target*. Expert Opin Ther Targets, 2018. 22(1): p. 85-96.

[59] Uchida, F., et al., *Overexpression of cell cycle regulator CDCA3 promotes oral cancer progression by enhancing cell proliferation with prevention of G1 phase arrest.* BMC Cancer, 2012. 12: p. 321.

[60] pšV, E. *Novel markers for detecting microsatellite instability in cancer and determining synthetic lethality with inhibition of the dna base excision repair pathway.* 2013.

[61] Antalis, C. J., et al., *High ACAT1 expression in estrogen receptor negative basal-like breast cancer cells is associated with LDL-induced prohferation.* Breast Cancer Res Treat, 2010. 122(3): p. 661-70.

[62] Chen, M. and J. Huang, *The expanded role of fatty acid metabolism in cancer: new aspects and targets.* Precis Clin Med, 2019. 2(3): p. 183-191.

[63] Kamphorst, J. J., et al., *Hypoxic and Ras-transformed cells support growth by scavenging unsaturated fatty acids from lysophospholipids.* Proc Natl Acad Sci USA, 2013. 110(22): p. 8882-7.

[64] Bensaad, K., et al., *Fatty acid uptake and lipid storage induced by HIF-1a contribute to cell growth and survival after hypoxia-reoxygenation.* Cell Rep, 2014. 9(1): p. 349-365.

[65] Damiano, F., et al., *Decanoic Acid and Not Octanoic Acid Stimulates Fatty Acid Synthesis in U87MG Glioblastoma Cells: A Metabolomics Study.* Front Neurosci, 2020. 14: p. 783.

[66] Li, J. N., et al., *Pharmacological inhibition of fatty acid synthase activity produces both cytostatic and cytotoxic effects modulated by p53.* Cancer Res, 2001. 61(4): p. 1493-9.

[67] Di Virgilio, F., et al., *Non-nucleotide Agonists Triggering P2X7 Receptor Activation and Pore Formation.* Frontiers in Pharmacology, 2018. 9(39).

[68] Ralevic, V. and G. Burnstock, *Receptors for purines and pyrimidines.* Pharmacol Rev, 1998. 50(3): p. 413-92.

[69] Sorrentino, C. and S. Morello, *Role of adenosine in tumor progression: focus on A<sub>2B<sub>receptor as potential therapeutic target.* Journal of Cancer Metastasis and Treatment, 2017. 3: p. 127-138.

What is claimed is:

1. A compound according to formula I, or pharmaceutically acceptable salt thereof:

(I)

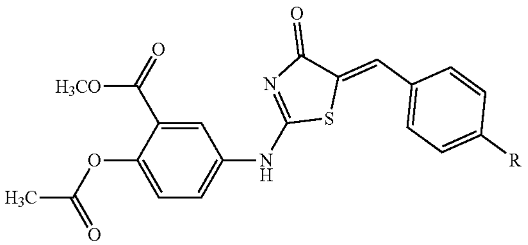

wherein R is independently selected from the group consisting of:

$R_1$=$CH_3$ and $R_2$=$N(CH_3)_2$.

2. The compound of claim 1, or pharmaceutically acceptable salt thereof, wherein the compound is of formula I.A:

(I.A)

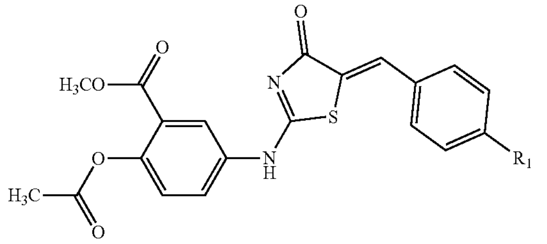

wherein $R_1$=$CH_3$.

3. The compound of claim 1, or pharmaceutically acceptable salt thereof, wherein the compound is of formula I.B:

(I.B)

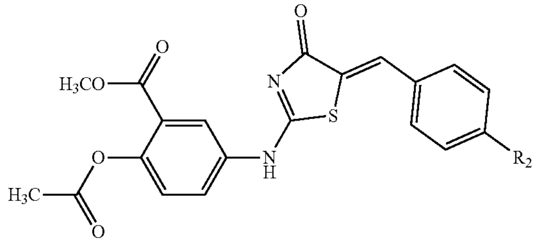

wherein $R_2$=$N(CH_3)_2$.

4. A method of synthesizing the compound of formula I.A of claim 2, comprising:

1. acetylating methyl 5-amino-2-hydroxybenzoate with acetic anhydride in presence of catalytic $H_2SO_4$ to obtain methyl 2-acetoxy-5-(chloroacetamido)benzoate;
2. heterocyclying methyl 2-acetoxy-5-(chloroacetamido)benzoate with ammonium thiocyanate to obtain methyl 2-acetoxy-5-[(4,5-dihydro-4-oxo-1,3-thiazol-2-yl)-amino]benzoate;
3. condensing methyl 2-acetoxy-5-[(4,5-dihydro-4-oxo-1,3-thiazol-2-yl)-amino]benzoate with 4-methylbenzaldehyde to obtain compound I.A.

5. A method of synthesizing the compound of formula I.B of claim 3, comprising:

1. acetylating methyl 5-amino-2-hydroxybenzoate with acetic anhydride in presence of catalytic $H_2SO_4$ to obtain methyl 2-acetoxy-5-(chloroacetamido)benzoate;
2. heterocyclying methyl 2-acetoxy-5-(chloroacetamido)benzoate with ammonium thiocyanate to obtain methyl 2-acetoxy-5-[(4,5-dihydro-4-oxo-1,3-thiazol-2-yl)-amino]benzoate;
3. condensing methyl 2-acetoxy-5-[(4,5-dihydro-4-oxo-1,3-thiazol-2-yl)-amino]benzoate with 4-dimethylaminobenzaldehyde to obtain compound I.B.

6. A pharmaceutical composition, comprising a therapeutically effective amount of one or more of the compounds, or pharmaceutically acceptable salts thereof, of claims 1, and one or more pharmaceutical excipients.

7. A method of treating a subject afflicted by a cancer, comprising administering to the subject in need thereof a therapeutically effective amount of the compound, or pharmaceutically acceptable salts thereof, of claims 1, and one or more pharmaceutical excipients.

8. The method of claim 7, wherein the compound is the compound of Formula I.A:

(I.A)

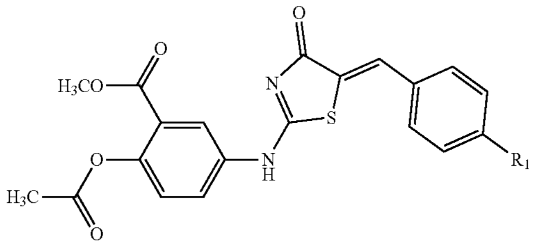

wherein:

$R1=CH_3$.

9. The method of claim 7, wherein the compound is the compound of Formula I.B:

(I.B)

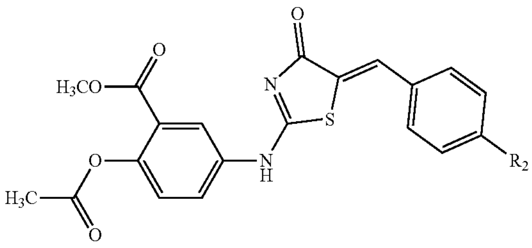

wherein:

$R2=N(CH_3)_2$.

10. The method of claims 7, wherein the subject is a mammal.

11. The method of claim 10, wherein the mammal is a human.

12. The method of claims 7, wherein the subject has cancer.

13. A kit for treating a subject with a cancer, comprising the compound of claims 1, or a pharmaceutically acceptable salt thereof and one or more pharmaceutical excipients.

* * * * *